US009005660B2

(12) United States Patent
Tygesen et al.

(10) Patent No.: US 9,005,660 B2
(45) Date of Patent: Apr. 14, 2015

(54) IMMEDIATE RELEASE COMPOSITION RESISTANT TO ABUSE BY INTAKE OF ALCOHOL

(75) Inventors: Peter Holm Tygesen, Smoerum (DK); Jan Martin Oevergaard, Frederikssund (DK); Joakim Oestman, Lomma (SE)

(73) Assignee: Egalet Ltd., London (GB)

( * ) Notice: Subject to any disclaimer, the term of this patent is extended or adjusted under 35 U.S.C. 154(b) by 473 days.

(21) Appl. No.: 12/701,248

(22) Filed: Feb. 5, 2010

(65) Prior Publication Data

US 2010/0204259 A1  Aug. 12, 2010

Related U.S. Application Data

(60) Provisional application No. 61/151,491, filed on Feb. 10, 2009, provisional application No. 61/150,577, filed on Feb. 6, 2009.

(30) Foreign Application Priority Data

Feb. 6, 2009 (DK) .................................. 2009 00190

(51) Int. Cl.
| A61K 9/46 | (2006.01) |
| A61K 9/16 | (2006.01) |
| A61K 31/44 | (2006.01) |
| A61K 31/16 | (2006.01) |
| A61K 31/485 | (2006.01) |
| A61K 31/167 | (2006.01) |
| A61K 9/28 | (2006.01) |
| A61K 9/20 | (2006.01) |

(52) U.S. Cl.
CPC ............. *A61K 9/0007* (2013.01); *A61K 31/485* (2013.01); *A61K 31/167* (2013.01); *A61K 9/2893* (2013.01); *A61K 9/2031* (2013.01); *A61K 9/2095* (2013.01); *A61K 9/2866* (2013.01)

(58) Field of Classification Search
USPC ............................ 424/466, 495; 514/282, 629
See application file for complete search history.

(56) References Cited

U.S. PATENT DOCUMENTS

| 2,685,553 | A | 8/1954 | Carroll et al. |
| 3,835,221 | A | 9/1974 | Fulberth et al. |
| 3,957,523 | A | 5/1976 | Ohno et al. |
| 4,034,758 | A | 7/1977 | Theeuwes |
| 4,330,338 | A | 5/1982 | Banker |
| 4,389,393 | A | 6/1983 | Schor et al. |
| 4,404,183 | A | 9/1983 | Kawata et al. |
| 4,449,983 | A | 5/1984 | Cortese et al. |
| 4,503,067 | A | 3/1985 | Wiedemann et al. |
| 4,686,212 | A | 8/1987 | Ducatman et al. |
| 4,824,675 | A | 4/1989 | Wong et al. |
| 4,844,984 | A | 7/1989 | Eckenhoff et al. |
| 4,873,080 | A | 10/1989 | Brickl et al. |
| 4,892,742 | A | 1/1990 | Shah |
| 4,898,733 | A | 2/1990 | DePrince et al. |
| 5,019,396 | A | 5/1991 | Ayer et al. |
| 5,068,112 | A | 11/1991 | Samejima et al. |
| 5,082,655 | A | 1/1992 | Snipes et al. |
| 5,102,668 | A | 4/1992 | Eichel et al. |
| 5,213,808 | A | 5/1993 | Bar Shalom et al. |
| 5,266,331 | A | 11/1993 | Oshlack et al. |
| 5,281,420 | A | 1/1994 | Kelm et al. |
| 5,352,455 | A | 10/1994 | Robertson |
| 5,411,745 | A | 5/1995 | Oshlack et al. |
| 5,419,917 | A | 5/1995 | Chen et al. |
| 5,422,123 | A | 6/1995 | Conte et al. |
| 5,460,826 | A | 10/1995 | Merrill et al. |
| 5,478,577 | A | 12/1995 | Sackler et al. |
| 5,508,042 | A | 4/1996 | Oshlack et al. |
| 5,520,931 | A | 5/1996 | Persson et al. |
| 5,529,787 | A | 6/1996 | Merrill et al. |
| 5,549,912 | A | 8/1996 | Oshlack et al. |
| 5,593,695 | A | 1/1997 | Merrill et al. |
| 5,609,885 | A | 3/1997 | Rivera et al. |
| 5,614,218 | A | 3/1997 | Olsson et al. |
| 5,618,560 | A | 4/1997 | Bar-Shalom et al. |
| 5,656,291 | A | 8/1997 | Olsson et al. |
| 5,656,295 | A | 8/1997 | Oshlack et al. |
| 5,667,805 | A | 9/1997 | Merrill et al. |
| 5,672,360 | A | 9/1997 | Sackler et al. |
| 5,741,524 | A | 4/1998 | Staniforth et al. |

(Continued)

FOREIGN PATENT DOCUMENTS

| DE | 202006014131 | 1/2007 |
| EP | 0435726 | 8/1991 |

(Continued)

OTHER PUBLICATIONS

Notification of Transmittal of the International Search Report and the Written Opinion of the International Searching Authority issued Jul. 8, 2008 in International Application No. PCT/DK2008/000016.
Preliminary Amendment filed Jul. 13, 2009 in co-pending U.S. Appl. No. 12/523,045.
Notification of Transmittal of the International Search Report and the Written Opinion of the International Searching Authority issued Apr. 21, 2010 in International Application No. PCT/EP2010/000728.
Notification of Transmittal of the International Search Report and the Written Opinion of the International Searching Authority issued May 28, 2010 in International Application No. PCT/DK2010/000019.
Fischer, et al., "Nonmedical Use of Prescription Opioids: Furthering a Meaningful Research Agenda," J. Pain. 9:6, 2008 490-493.

(Continued)

*Primary Examiner* — Shirley V Gembeh
(74) *Attorney, Agent, or Firm* — Foley & Lardner LLP

(57) ABSTRACT

The present invention relates to immediate release pharmaceutical compositions for oral administration that are resistant to abuse by intake of alcohol. In particular, this disclosure provides immediate release pharmaceutical compositions comprising a polyglycol having a molecular weight of from about 900 to about 17,000 daltons, a drug substance, one or more effervescent agents, and, optionally, one or more disintegrants, such that the composition is formulated to be resistant to abuse by intake of alcohol.

13 Claims, 23 Drawing Sheets

(56) References Cited

U.S. PATENT DOCUMENTS

Figure 1:
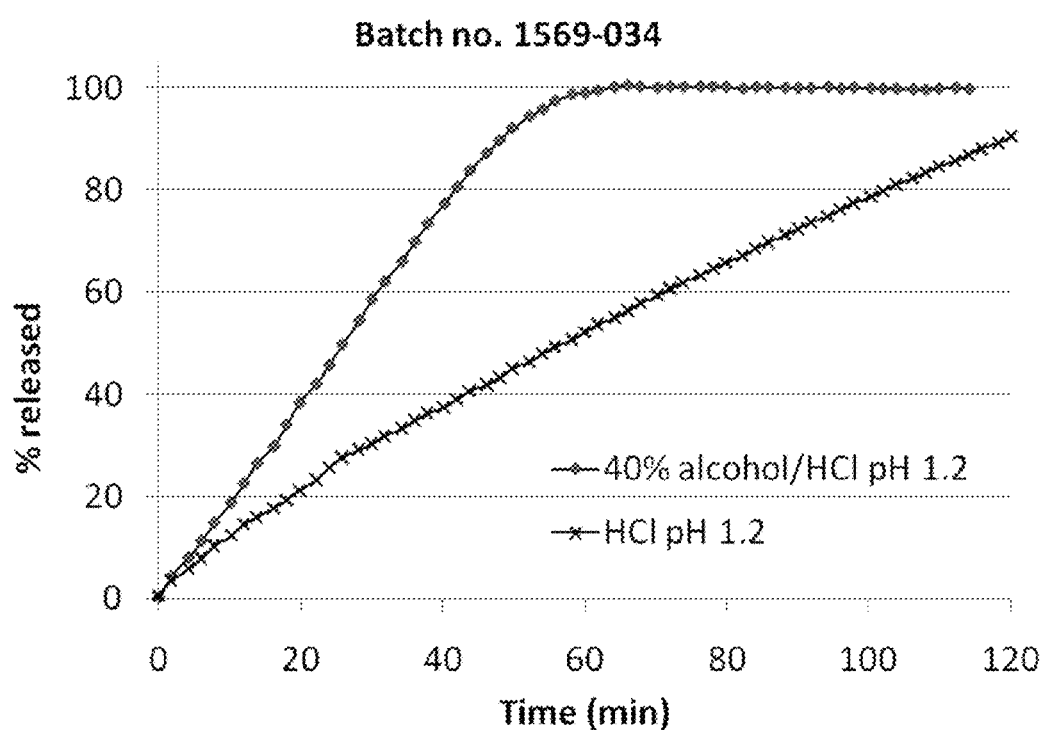

| | | |
|---|---|---|
| 5,866,161 A | 2/1999 | Childers et al. |
| 5,866,164 A | 2/1999 | Kuczynski et al. |
| 5,869,097 A | 2/1999 | Wong et al. |
| 5,879,705 A | 3/1999 | Heafield et al. |
| 5,882,682 A | 3/1999 | Rork et al. |
| 5,914,131 A | 6/1999 | Merrill et al. |
| 5,948,787 A | 9/1999 | Merrill et al. |
| 5,952,005 A | 9/1999 | Olsson et al. |
| 5,968,551 A | 10/1999 | Oshlack et al. |
| 6,046,177 A | 4/2000 | Stella et al. |
| 6,066,339 A | 5/2000 | Stark et al. |
| 6,077,533 A | 6/2000 | Oshlack et al. |
| 6,077,538 A | 6/2000 | Merrill et al. |
| 6,103,261 A | 8/2000 | Chasin et al. |
| 6,117,453 A | 9/2000 | Seth et al. |
| 6,143,328 A | 11/2000 | Heafield et al. |
| 6,183,778 B1 | 2/2001 | Conte et al. |
| 6,225,343 B1 | 5/2001 | Behl et al. |
| 6,245,351 B1 | 6/2001 | Nara et al. |
| 6,245,357 B1 | 6/2001 | Edgren et al. |
| 6,267,981 B1 | 7/2001 | Okamoto et al. |
| 6,267,985 B1 | 7/2001 | Chen et al. |
| 6,277,384 B1 | 8/2001 | Kaiko et al. |
| 6,284,274 B1 | 9/2001 | Merrill et al. |
| 6,294,195 B1 | 9/2001 | Oshlack et al. |
| 6,348,216 B1 | 2/2002 | Kushla et al. |
| 6,375,957 B1 | 4/2002 | Kaiko et al. |
| 6,383,471 B1 | 5/2002 | Chen et al. |
| 6,395,299 B1 | 5/2002 | Babich et al. |
| 6,399,096 B1 | 6/2002 | Miller et al. |
| 6,403,579 B1 | 6/2002 | Heller |
| 6,451,848 B1 | 9/2002 | Behl et al. |
| 6,458,772 B1 | 10/2002 | Zhou et al. |
| 6,458,824 B1 | 10/2002 | Iwata et al. |
| 6,475,494 B2 | 11/2002 | Kaiko et al. |
| 6,482,437 B2 | 11/2002 | Debregeas et al. |
| 6,488,962 B1 | 12/2002 | Berner et al. |
| 6,488,963 B1 | 12/2002 | McGinity et al. |
| 6,491,945 B1 | 12/2002 | Childers et al. |
| 6,517,866 B1 | 2/2003 | Am Ende et al. |
| 6,534,085 B1 | 3/2003 | Zeligs |
| 6,543,085 B2 | 4/2003 | Holsten et al. |
| 6,562,375 B1 | 5/2003 | Sako et al. |
| 6,572,885 B2 | 6/2003 | Oshlack et al. |
| 6,599,531 B2 | 7/2003 | Kushla et al. |
| 6,607,751 B1 | 8/2003 | Odidi et al. |
| 6,632,832 B1 | 10/2003 | Burman et al. |
| 6,673,816 B1 | 1/2004 | Esswein et al. |
| 6,685,964 B1 | 2/2004 | Bartholomaeus et al. |
| 6,696,066 B2 | 2/2004 | Kaiko et al. |
| 6,709,678 B2 | 3/2004 | Gruber |
| 6,730,326 B2 | 5/2004 | Beyer et al. |
| 6,733,783 B2 | 5/2004 | Oshlack et al. |
| 6,757,558 B2 | 6/2004 | Lange et al. |
| 6,787,156 B1 | 9/2004 | Bar-Shalom |
| 6,800,668 B1 | 10/2004 | Odidi et al. |
| 6,837,696 B2 | 1/2005 | Sowden et al. |
| 6,852,337 B2 | 2/2005 | Gabel et al. |
| 6,960,357 B2 | 11/2005 | Chopra |
| 7,060,293 B1 | 6/2006 | Oshlack et al. |
| 7,063,864 B1 | 6/2006 | Marechal et al. |
| 7,090,867 B2 | 8/2006 | Odidi et al. |
| 7,144,587 B2 | 12/2006 | Oshlack et al. |
| 7,172,767 B2 | 2/2007 | Kaiko et al. |
| 7,201,920 B2 | 4/2007 | Kumar et al. |
| 7,270,831 B2 | 9/2007 | Oshlack et al. |
| 7,332,182 B2 | 2/2008 | Sackler |
| 7,399,488 B2 | 7/2008 | Hirsh et al. |
| 7,419,686 B2 | 9/2008 | Kaiko et al. |
| 7,476,402 B2 | 1/2009 | Kumar et al. |
| 7,510,726 B2 | 3/2009 | Kumar et al. |
| 7,510,727 B2 | 3/2009 | Oshlack et al. |
| 7,514,100 B2 | 4/2009 | Oshlack et al. |
| 7,666,337 B2 | 2/2010 | Yang et al. |
| 7,749,542 B2 | 7/2010 | Kaiko et al. |
| 7,771,707 B2 | 8/2010 | Hirsh et al. |
| 7,776,314 B2 | 8/2010 | Bartholomaus et al. |
| 7,842,307 B2 | 11/2010 | Oshlack et al. |
| 7,846,476 B2 | 12/2010 | Oshlack et al. |
| 7,883,722 B2 | 2/2011 | Bar-Shalom |
| 7,883,772 B2 | 2/2011 | Pourdeyhimi et al. |
| 7,897,080 B2 | 3/2011 | Yang et al. |
| 7,906,143 B1 | 3/2011 | Odidi et al. |
| 7,943,174 B2 | 5/2011 | Oshlack et al. |
| 7,968,120 B2 | 6/2011 | Li et al. |
| 7,972,624 B2 | 7/2011 | Li et al. |
| 7,981,439 B2 | 7/2011 | Kumar et al. |
| 8,017,148 B2 | 9/2011 | Sackler |
| 8,017,150 B2 | 9/2011 | Yang et al. |
| 8,029,822 B2 | 10/2011 | Faour et al. |
| 8,075,872 B2 | 12/2011 | Arkenau-Maric et al. |
| 8,101,630 B2 | 1/2012 | Kumar et al. |
| 8,105,631 B2 | 1/2012 | Kaiko et al. |
| 8,114,383 B2 | 2/2012 | Bartholomaus et al. |
| 8,114,384 B2 | 2/2012 | Arkenau et al. |
| 8,133,507 B2 | 3/2012 | Yum et al. |
| 8,142,811 B2 | 3/2012 | Oshlack et al. |
| 8,147,870 B2 | 4/2012 | Yum et al. |
| 8,153,152 B2 | 4/2012 | Yum et al. |
| 8,168,217 B2 | 5/2012 | Yum et al. |
| 8,173,152 B2 | 5/2012 | Crowley et al. |
| 8,182,836 B2 | 5/2012 | Mehta |
| 8,192,722 B2 | 6/2012 | Arkenau-Maric et al. |
| 8,231,898 B2 | 7/2012 | Oshlack et al. |
| 8,246,986 B2 | 8/2012 | Cruz et al. |
| 8,309,060 B2 | 11/2012 | Bartholomaus et al. |
| 8,323,889 B2 | 12/2012 | Arkenau-Maric et al. |
| 8,329,720 B1 | 12/2012 | King et al. |
| 8,337,888 B2 | 12/2012 | Wright et al. |
| 8,338,444 B1 | 12/2012 | King et al. |
| 8,354,124 B2 | 1/2013 | Yum et al. |
| 8,361,499 B2 | 1/2013 | Oshlack et al. |
| 8,367,693 B1 | 2/2013 | King et al. |
| 8,372,432 B2 | 2/2013 | Han et al. |
| 8,377,453 B2 | 2/2013 | Han et al. |
| 8,383,152 B2 | 2/2013 | Jans et al. |
| 8,383,154 B2 | 2/2013 | Bar-Shalom |
| 8,383,155 B2 | 2/2013 | Bar-Shalom |
| 8,389,007 B2 | 3/2013 | Wright et al. |
| 8,394,407 B2 | 3/2013 | Vergnault et al. |
| 8,394,408 B2 | 3/2013 | Han et al. |
| 8,409,616 B2 | 4/2013 | Kumar et al. |
| 8,415,401 B2 | 4/2013 | Yum et al. |
| 8,420,056 B2 | 4/2013 | Arkenau-Maric et al. |
| 8,420,120 B2 | 4/2013 | Yum et al. |
| 8,425,933 B2 | 4/2013 | Mehta |
| 8,445,018 B2 | 5/2013 | Habib et al. |
| 8,449,909 B2 | 5/2013 | Hirsh et al. |
| 8,449,914 B2 | 5/2013 | Fischer et al. |
| 8,460,640 B2 | 6/2013 | Vinson et al. |
| 8,465,776 B2 | 6/2013 | Hoarau |
| 8,470,361 B2 | 6/2013 | Pettersson |
| 8,476,291 B1 | 7/2013 | King et al. |
| 8,486,423 B2 | 7/2013 | Brough et al. |
| 8,486,448 B2 | 7/2013 | Rahmouni et al. |
| 8,486,449 B2 | 7/2013 | Rahmouni et al. |
| 8,491,935 B2 | 7/2013 | Mehta et al. |
| 8,501,160 B2 | 8/2013 | Cailly-Dufestel et al. |
| 8,506,998 B2 | 8/2013 | Miller et al. |
| 8,524,275 B2 | 9/2013 | Oshlack et al. |
| 8,524,277 B2 | 9/2013 | Edgren et al. |
| 8,529,848 B2 | 9/2013 | Danehy et al. |
| 8,541,026 B2 | 9/2013 | Qiu et al. |
| 8,603,526 B2 | 12/2013 | Tygesen et al. |
| 8,609,143 B2 | 12/2013 | Fischer et al. |
| 8,609,683 B2 | 12/2013 | Wright et al. |
| 8,617,605 B2 | 12/2013 | Fischer et al. |
| 8,637,540 B2 | 1/2014 | Kumar et al. |
| 8,703,189 B2 | 4/2014 | Tomohira |
| 8,765,178 B2 | 7/2014 | Parikh et al. |
| 8,808,745 B2 | 8/2014 | Fischer et al. |
| 2001/0036959 A1 | 11/2001 | Gabel et al. |
| 2001/0036960 A1 | 11/2001 | Decker et al. |
| 2001/0053791 A1 | 12/2001 | Babcock et al. |

(56) References Cited

U.S. PATENT DOCUMENTS

| | | |
|---|---|---|
| 2002/0054911 A1 | 5/2002 | Oh |
| 2002/0119197 A1 | 8/2002 | Dyar et al. |
| 2003/0035836 A1 | 2/2003 | Shanghvi et al. |
| 2003/0068375 A1 | 4/2003 | Wright et al. |
| 2003/0077320 A1 | 4/2003 | Childers et al. |
| 2003/0091635 A1 | 5/2003 | Baichwal et al. |
| 2003/0118641 A1 | 6/2003 | Maloney et al. |
| 2003/0129231 A1 | 7/2003 | Oshlack et al. |
| 2003/0133976 A1 | 7/2003 | Pather et al. |
| 2003/0203055 A1 | 10/2003 | Rao et al. |
| 2003/0224051 A1 | 12/2003 | Fink et al. |
| 2004/0010000 A1 | 1/2004 | Ayer et al. |
| 2004/0028733 A1 | 2/2004 | Tracy et al. |
| 2004/0091529 A1 | 5/2004 | Edgren et al. |
| 2004/0102476 A1 | 5/2004 | Chan et al. |
| 2004/0115262 A1 | 6/2004 | Jao et al. |
| 2004/0151772 A1 | 8/2004 | Andersen et al. |
| 2004/0202717 A1 | 10/2004 | Mehta |
| 2004/0204474 A1 | 10/2004 | Decker et al. |
| 2004/0213849 A1 | 10/2004 | Sowden et al. |
| 2004/0220250 A1 | 11/2004 | Oh et al. |
| 2004/0224020 A1 | 11/2004 | Schoenhard |
| 2004/0234602 A1 | 11/2004 | Fischer et al. |
| 2004/0253310 A1 | 12/2004 | Fischer et al. |
| 2005/0019399 A1 | 1/2005 | Fischer et al. |
| 2005/0019405 A1 | 1/2005 | Bar-Shalom |
| 2005/0020613 A1 | 1/2005 | Boehm et al. |
| 2005/0053655 A1 | 3/2005 | Yang et al. |
| 2005/0074493 A1 | 4/2005 | Mehta et al. |
| 2005/0089569 A1 | 4/2005 | Bar-Shalom |
| 2005/0089570 A1 | 4/2005 | Cruz et al. |
| 2005/0106249 A1 | 5/2005 | Hwang et al. |
| 2005/0152843 A1 | 7/2005 | Bartholomaus et al. |
| 2005/0158382 A1 | 7/2005 | Cruz et al. |
| 2005/0163837 A1 | 7/2005 | Boehm et al. |
| 2005/0169992 A1 | 8/2005 | Jao et al. |
| 2005/0236741 A1 | 10/2005 | Arkenau et al. |
| 2006/0002860 A1 | 1/2006 | Bartholomous et al. |
| 2006/0039864 A1 | 2/2006 | Barthlomaus et al. |
| 2006/0110327 A1 | 5/2006 | Emigh et al. |
| 2006/0165790 A1 | 7/2006 | Walden et al. |
| 2006/0177380 A1 | 8/2006 | Emigh et al. |
| 2006/0177507 A1 | 8/2006 | Faour et al. |
| 2006/0188447 A1 | 8/2006 | Arkenau-Maric et al. |
| 2006/0193782 A1 | 8/2006 | Bartholomaus et al. |
| 2006/0193912 A1 | 8/2006 | Ketsela et al. |
| 2006/0193914 A1 | 8/2006 | Ashworth et al. |
| 2007/0003616 A1 | 1/2007 | Arkenau-Maric et al. |
| 2007/0003617 A1 | 1/2007 | Fischer et al. |
| 2007/0003620 A1 | 1/2007 | Marechal et al. |
| 2007/0004797 A1 | 1/2007 | Weyers et al. |
| 2007/0020331 A1 | 1/2007 | Gold et al. |
| 2007/0042044 A1 | 2/2007 | Fischer et al. |
| 2007/0048228 A1 | 3/2007 | Arkenau-Maric et al. |
| 2007/0065510 A1 | 3/2007 | Odidi et al. |
| 2007/0122455 A1 | 5/2007 | Myers et al. |
| 2007/0190142 A1 | 8/2007 | Breitenbach et al. |
| 2007/0224129 A1 | 9/2007 | Guimberteau et al. |
| 2007/0231268 A1 | 10/2007 | Emigh et al. |
| 2007/0259033 A1 | 11/2007 | Cruz et al. |
| 2007/0259045 A1 | 11/2007 | Mannion et al. |
| 2007/0264326 A1 | 11/2007 | Guimberteau et al. |
| 2007/0264346 A1 | 11/2007 | Guimberteau et al. |
| 2007/0275062 A1 | 11/2007 | Oshlack et al. |
| 2007/0281003 A1 | 12/2007 | Fuisz et al. |
| 2008/0026052 A1 | 1/2008 | Schoenhard |
| 2008/0031901 A1 | 2/2008 | Qiu et al. |
| 2008/0044454 A1 | 2/2008 | Yang et al. |
| 2008/0063725 A1 | 3/2008 | Guimberteau et al. |
| 2008/0069891 A1 | 3/2008 | Habib et al. |
| 2008/0075771 A1 | 3/2008 | Vaughn et al. |
| 2008/0102121 A1 | 5/2008 | Devane et al. |
| 2008/0113025 A1 | 5/2008 | Devane et al. |
| 2008/0152595 A1 | 6/2008 | Emigh et al. |
| 2008/0166407 A1 | 7/2008 | Shalaby et al. |
| 2008/0193540 A1 | 8/2008 | Soula et al. |
| 2008/0200493 A1 | 8/2008 | Drewes et al. |
| 2008/0234352 A1 | 9/2008 | Fischer et al. |
| 2008/0247959 A1 | 10/2008 | Barthlomaus et al. |
| 2008/0248110 A1 | 10/2008 | Pettersson et al. |
| 2008/0248113 A1 | 10/2008 | Barthlomaus et al. |
| 2008/0254122 A1 | 10/2008 | Fischer et al. |
| 2008/0254123 A1 | 10/2008 | Fischer et al. |
| 2008/0254124 A1 | 10/2008 | Bar-Shalom |
| 2008/0268057 A1 | 10/2008 | Andersen et al. |
| 2008/0299199 A1 | 12/2008 | Bar Shalom et al. |
| 2008/0311187 A1 | 12/2008 | Ashworth et al. |
| 2008/0311197 A1 | 12/2008 | Arkenau-Maric et al. |
| 2008/0311205 A1 | 12/2008 | Habib et al. |
| 2008/0317854 A1 | 12/2008 | Arkenau et al. |
| 2009/0004267 A1 | 1/2009 | Arkenau-Maric et al. |
| 2009/0005408 A1 | 1/2009 | Arkenau-Maric et al. |
| 2009/0011016 A1 | 1/2009 | Cailly-Dufestel et al. |
| 2009/0022790 A1 | 1/2009 | Flath et al. |
| 2009/0022798 A1 | 1/2009 | Rosenberg et al. |
| 2009/0041838 A1 | 2/2009 | Guimberteau et al. |
| 2009/0081290 A1 | 3/2009 | McKenna et al. |
| 2009/0099151 A1 | 4/2009 | Jain et al. |
| 2009/0155357 A1 | 6/2009 | Muhuri |
| 2009/0169631 A1 | 7/2009 | Zamloot et al. |
| 2009/0202634 A1 | 8/2009 | Jans et al. |
| 2009/0274759 A1 | 11/2009 | Bar-Shalom et al. |
| 2009/0298862 A1 | 12/2009 | Yum et al. |
| 2009/0317355 A1 | 12/2009 | Roth et al. |
| 2010/0099696 A1 | 4/2010 | Soscia et al. |
| 2010/0151028 A1 | 6/2010 | Ashworth et al. |
| 2010/0168148 A1 | 7/2010 | Wright et al. |
| 2010/0172989 A1 | 7/2010 | Roth et al. |
| 2010/0203129 A1 | 8/2010 | Andersen et al. |
| 2010/0203130 A1 | 8/2010 | Tygesen et al. |
| 2010/0204259 A1 | 8/2010 | Tygesen et al. |
| 2010/0239667 A1 | 9/2010 | Hemmingsen et al. |
| 2010/0266701 A1 | 10/2010 | Guimberteau et al. |
| 2010/0291205 A1 | 11/2010 | Downie et al. |
| 2011/0008424 A1 | 1/2011 | Chang et al. |
| 2011/0020451 A1 | 1/2011 | Bartholmaus et al. |
| 2011/0038930 A1 | 2/2011 | Barnscheid et al. |
| 2011/0077238 A1 | 3/2011 | Leech et al. |
| 2011/0104214 A1 | 5/2011 | Oshlack et al. |
| 2011/0136847 A1 | 6/2011 | Chan et al. |
| 2011/0142905 A1 | 6/2011 | Naelapaa et al. |
| 2011/0159100 A1 | 6/2011 | Andersen et al. |
| 2011/0195989 A1 | 8/2011 | Rudnic et al. |
| 2011/0200681 A1 | 8/2011 | Habib et al. |
| 2011/0200715 A1 | 8/2011 | Fuisz et al. |
| 2011/0229526 A1 | 9/2011 | Rosenberg et al. |
| 2011/0229533 A1 | 9/2011 | Edgren et al. |
| 2011/0287093 A1 | 11/2011 | Schoenhard |
| 2012/0009129 A1 | 1/2012 | Brzeczko |
| 2012/0015007 A1 | 1/2012 | Bredenberg et al. |
| 2012/0059065 A1 | 3/2012 | Barnscheid et al. |
| 2012/0065220 A1 | 3/2012 | Barnscheid et al. |
| 2012/0135075 A1 | 5/2012 | Mohammad |
| 2012/0136021 A1 | 5/2012 | Barnscheid et al. |
| 2012/0164220 A1 | 6/2012 | Huang |
| 2012/0201761 A1 | 8/2012 | Sackler |
| 2012/0202838 A1 | 8/2012 | Ghosh et al. |
| 2012/0202839 A1 | 8/2012 | Emigh et al. |
| 2012/0214777 A1 | 8/2012 | Crowley et al. |
| 2012/0225122 A1 | 9/2012 | Hamed et al. |
| 2012/0251637 A1 | 10/2012 | Bartholomaus et al. |
| 2012/0321674 A1 | 12/2012 | Vachon et al. |
| 2012/0321713 A1 | 12/2012 | Han et al. |
| 2012/0321716 A1 | 12/2012 | Vachon et al. |
| 2013/0005823 A1 | 1/2013 | Emigh et al. |
| 2013/0011479 A1 | 1/2013 | Angeli et al. |
| 2013/0012533 A1 | 1/2013 | Oshlack et al. |
| 2013/0022646 A1 | 1/2013 | Rudnic et al. |
| 2013/0028177 A1 | 1/2013 | Koskela et al. |
| 2013/0028970 A1 | 1/2013 | Schwier et al. |
| 2013/0028972 A1 | 1/2013 | Schwier et al. |
| 2013/0030561 A1 | 1/2013 | Imanari et al. |
| 2013/0084333 A1 | 4/2013 | Dick et al. |
| 2013/0090349 A1 | 4/2013 | Geibler et al. |

(56) References Cited

U.S. PATENT DOCUMENTS

| | | |
|---|---|---|
| 2013/0122087 A1 | 5/2013 | Habib et al. |
| 2013/0122101 A1 | 5/2013 | Habib et al. |
| 2013/0129825 A1 | 5/2013 | Billoet et al. |
| 2013/0129826 A1 | 5/2013 | Geibler et al. |
| 2013/0171075 A1 | 7/2013 | Arkenau-Maric et al. |
| 2013/0171257 A1 | 7/2013 | Kumar et al. |
| 2013/0195981 A1 | 8/2013 | Pettersson |
| 2013/0195982 A1 | 8/2013 | Pettersson |
| 2013/0209557 A1 | 8/2013 | Barnscheid |
| 2013/0209560 A1 | 8/2013 | Hamed et al. |
| 2013/0217716 A1 | 8/2013 | Wright et al. |
| 2013/0225697 A1 | 8/2013 | Barnscheid et al. |
| 2013/0230596 A1 | 9/2013 | Mehta |
| 2013/0245055 A1 | 9/2013 | Wright et al. |
| 2013/0251759 A1 | 9/2013 | Jans et al. |
| 2013/0251796 A1 | 9/2013 | McKenna et al. |
| 2013/0251798 A1 | 9/2013 | McKenna et al. |
| 2013/0251799 A1 | 9/2013 | McKenna et al. |
| 2013/0251801 A1 | 9/2013 | McKenna et al. |
| 2013/0251802 A1 | 9/2013 | McKenna et al. |
| 2013/0251806 A1 | 9/2013 | Andrade de Freitas et al. |
| 2013/0259939 A1 | 10/2013 | McKenna et al. |
| 2013/0259940 A1 | 10/2013 | McKenna et al. |
| 2013/0260015 A1 | 10/2013 | McKenna et al. |
| 2013/0261143 A1 | 10/2013 | Wright et al. |
| 2013/0273162 A1 | 10/2013 | Li et al. |
| 2013/0280176 A1 | 10/2013 | Diezi et al. |
| 2013/0280338 A1 | 10/2013 | Wening et al. |
| 2013/0281480 A1 | 10/2013 | Yum et al. |
| 2013/0287845 A1 | 10/2013 | Yum et al. |
| 2013/0287849 A1 | 10/2013 | Andersen et al. |
| 2013/0295168 A1 | 11/2013 | Yum et al. |
| 2013/0303494 A1 | 11/2013 | Wright et al. |
| 2013/0303623 A1 | 11/2013 | Barnscheid et al. |
| 2013/0317049 A1 | 11/2013 | Yum et al. |
| 2013/0317051 A1 | 11/2013 | Oshlack et al. |
| 2013/0320592 A1 | 12/2013 | Arkenau-Maric et al. |
| 2013/0337059 A1 | 12/2013 | Yum et al. |
| 2013/0337060 A1 | 12/2013 | Yum et al. |
| 2013/0344142 A1 | 12/2013 | Rahmouni et al. |
| 2013/0344143 A1 | 12/2013 | Rosenberg et al. |
| 2014/0004191 A1 | 1/2014 | Rahmouni et al. |
| 2014/0030327 A1 | 1/2014 | McKenna et al. |
| 2014/0120164 A1 | 5/2014 | Fischer et al. |
| 2014/0155388 A1 | 6/2014 | Brzeczko et al. |
| 2014/0193490 A1 | 7/2014 | Schoenhard |
| 2014/0220126 A1 | 8/2014 | Tygesen et al. |
| 2014/0221416 A1 | 8/2014 | Guido et al. |
| 2014/0271848 A1 | 9/2014 | Guido et al. |
| 2014/0271849 A1 | 9/2014 | Raman et al. |
| 2014/0271896 A1 | 9/2014 | Shmeis et al. |
| 2014/0275143 A1 | 9/2014 | Devarakonda et al. |
| 2014/0294947 A1 | 10/2014 | Reilly et al. |

FOREIGN PATENT DOCUMENTS

| | | |
|---|---|---|
| EP | 0493513 | 7/1992 |
| EP | 0406315 | 11/1992 |
| EP | 0 908 181 | 4/1999 |
| EP | 1 027 888 | 8/2000 |
| EP | 0 335 560 | 1/2002 |
| EP | 1213014 | 6/2002 |
| EP | 1 371 360 | 5/2005 |
| GB | 1430684 | 3/1976 |
| GB | 2170104 | 7/1986 |
| GB | 2182559 | 5/1987 |
| JP | 60/255719 | 12/1985 |
| JP | 07/100191 | 4/1995 |
| WO | WO 86/04817 | 8/1986 |
| WO | WO 89/09066 | 10/1989 |
| WO | WO 90/08536 | 8/1990 |
| WO | WO 91/04015 | 4/1991 |
| WO | WO 92/09270 | 6/1992 |
| WO | WO 93/10765 | 6/1993 |
| WO | WO 95/22962 | 8/1995 |
| WO | WO 96/00066 A1 | 1/1996 |
| WO | WO 96/08253 A1 | 3/1996 |
| WO | WO 97/33566 A2 | 9/1997 |
| WO | WO 99/05105 | 2/1999 |
| WO | WO 99/44591 A1 | 9/1999 |
| WO | WO 99/51208 | 10/1999 |
| WO | WO 00/41704 | 7/2000 |
| WO | WO 01/35958 | 5/2001 |
| WO | WO 01/51035 | 7/2001 |
| WO | WO 01/51036 | 7/2001 |
| WO | WO 01/74357 | 10/2001 |
| WO | WO 02/056861 A2 | 7/2002 |
| WO | WO 02/065834 | 8/2002 |
| WO | WO 02/087512 A1 | 11/2002 |
| WO | WO 02/092078 | 11/2002 |
| WO | WO 03/024426 | 3/2003 |
| WO | WO 03/024429 | 3/2003 |
| WO | WO 03/024430 | 3/2003 |
| WO | WO 03/026613 | 4/2003 |
| WO | WO 03/039521 | 5/2003 |
| WO | WO 03/075897 | 9/2003 |
| WO | WO 03/082204 | 10/2003 |
| WO | WO 03/092648 A1 | 11/2003 |
| WO | WO 03/101384 A2 | 12/2003 |
| WO | WO 2004/002447 A2 | 1/2004 |
| WO | WO 2004/041252 | 5/2004 |
| WO | WO 2004/047839 A1 | 6/2004 |
| WO | WO 2004/054542 A2 | 7/2004 |
| WO | WO 2004/056337 A2 | 7/2004 |
| WO | WO 2004/084868 | 10/2004 |
| WO | WO 2004/084869 | 10/2004 |
| WO | WO 2004/091512 A2 | 10/2004 |
| WO | WO 2004/093819 | 11/2004 |
| WO | WO 2004/093843 | 11/2004 |
| WO | WO 2005/000310 A1 | 1/2005 |
| WO | WO 2005/007074 | 1/2005 |
| WO | WO 2005/016313 | 2/2005 |
| WO | WO 2005/016314 A1 | 2/2005 |
| WO | WO 2005/027878 | 3/2005 |
| WO | WO 2005/034859 A2 | 4/2005 |
| WO | WO 2005/053587 A1 | 6/2005 |
| WO | WO 2005/063206 A1 | 7/2005 |
| WO | WO 2005/063214 A1 | 7/2005 |
| WO | WO 2005/102286 A1 | 11/2005 |
| WO | WO 2006/002883 A1 | 1/2006 |
| WO | WO 2006/002884 A1 | 1/2006 |
| WO | WO 2006/002886 A1 | 1/2006 |
| WO | WO 2006/026504 | 3/2006 |
| WO | WO 2006/030402 A2 | 3/2006 |
| WO | WO 2006/031209 A1 | 3/2006 |
| WO | WO 2006/058249 | 6/2006 |
| WO | WO 2006/058249 A2 | 6/2006 |
| WO | WO 2006/088305 A1 | 8/2006 |
| WO | WO 2006/089843 A2 | 8/2006 |
| WO | WO 2006/103418 A1 | 10/2006 |
| WO | WO 2006/103551 | 10/2006 |
| WO | WO 2006/106344 | 10/2006 |
| WO | WO 2005/107713 | 11/2006 |
| WO | WO 2006/128471 | 12/2006 |
| WO | WO 2007/014061 A2 | 2/2007 |
| WO | WO 2007/030754 A2 | 3/2007 |
| WO | WO 2007/053698 | 5/2007 |
| WO | WO 2007/082757 A2 | 7/2007 |
| WO | WO 2007/085024 A2 | 7/2007 |
| WO | WO 2007/106550 A2 | 9/2007 |
| WO | WO 2007/112285 A2 | 10/2007 |
| WO | WO 2007/112286 A2 | 10/2007 |
| WO | WO 2007/131357 | 11/2007 |
| WO | WO 2007/133583 A2 | 11/2007 |
| WO | WO 2007/135193 A2 | 11/2007 |
| WO | WO 2007/150074 A2 | 12/2007 |
| WO | WO 2007/150075 A2 | 12/2007 |
| WO | WO 2008/023261 | 2/2008 |
| WO | WO 2008/023261 A1 | 2/2008 |
| WO | WO 2008/027442 A2 | 3/2008 |
| WO | WO 2008/028047 A2 | 3/2008 |
| WO | WO 2008/033523 A1 | 3/2008 |
| WO | WO 2008/068471 A1 | 6/2008 |

(56) References Cited

FOREIGN PATENT DOCUMENTS

| WO | WO 2008/086804 | | 7/2008 |
|---|---|---|---|
| WO | WO 2008/100375 | A2 | 8/2008 |
| WO | WO 2008/107149 | A2 | 9/2008 |
| WO | WO 2008/148798 | | 12/2008 |
| WO | WO 2008148798 | A2 * | 12/2008 |
| WO | WO 2009/035474 | A1 | 3/2009 |
| WO | WO 2009/075782 | A1 | 6/2009 |
| WO | WO 2009/076236 | A2 | 6/2009 |
| WO | WO 2009/076764 | A1 | 6/2009 |
| WO | WO 2009/088414 | A2 | 7/2009 |
| WO | WO 2009/092601 | A1 | 7/2009 |
| WO | WO 2009/104838 | A1 | 8/2009 |
| WO | WO 2009/114648 | A1 | 9/2009 |
| WO | WO 2010/017821 | A1 | 2/2010 |
| WO | WO 2010/032128 | | 3/2010 |
| WO | WO 2010/032128 | A1 | 3/2010 |
| WO | WO 2010/066034 | A1 | 6/2010 |
| WO | WO 2010/069050 | A1 | 6/2010 |
| WO | WO 2010/083894 | A1 | 7/2010 |
| WO | WO 2010/088911 | | 8/2010 |
| WO | WO 2010/089132 | | 8/2010 |
| WO | WO 2010/140007 | A2 | 12/2010 |
| WO | WO 2010/151741 | A1 | 12/2010 |
| WO | WO 2011/009602 | A1 | 1/2011 |
| WO | WO 2011/009603 | A1 | 1/2011 |
| WO | WO 2011/009604 | A1 | 1/2011 |
| WO | WO 2011/041414 | A1 | 4/2011 |
| WO | WO 2011/068723 | A1 | 6/2011 |
| WO | WO 2011/079248 | A1 | 6/2011 |
| WO | WO 2011/106416 | A2 | 9/2011 |
| WO | WO 2012/028317 | A1 | 3/2012 |
| WO | WO 2012/028318 | A1 | 3/2012 |
| WO | WO 2012/028319 | A1 | 3/2012 |
| WO | WO 2012/040651 | A1 | 3/2012 |
| WO | WO 2012/061779 | A1 | 5/2012 |
| WO | WO 2012/076907 | A2 | 6/2012 |
| WO | WO 2012/080833 | A2 | 6/2012 |
| WO | WO 2012/085656 | A2 | 6/2012 |
| WO | WO 2012/085657 | A2 | 6/2012 |
| WO | WO 2012/112952 | A1 | 8/2012 |
| WO | WO 2012/131463 | A2 | 10/2012 |
| WO | WO 2013/017234 | A1 | 2/2013 |
| WO | WO 2013/017242 | A1 | 2/2013 |
| WO | WO 2013/030177 | | 3/2013 |
| WO | WO 2013/038267 | A1 | 3/2013 |
| WO | WO 2013/038268 | A1 | 3/2013 |
| WO | WO 2013/050539 | A2 | 4/2013 |
| WO | WO 2013/057570 | A2 | 4/2013 |
| WO | WO 2013/072395 | A1 | 5/2013 |
| WO | WO 2013/077851 | A1 | 5/2013 |
| WO | WO 2013/084059 | A1 | 6/2013 |
| WO | WO 2013/128276 | A2 | 9/2013 |
| WO | WO 2013/171146 | | 11/2013 |
| WO | WO 2014/091437 | | 6/2014 |

OTHER PUBLICATIONS

Meyer, et al., "Awareness Topic: Mitigating the Risks of Ethanol Induced Dose Dumping from Oral Sustained/Controlled Release Dosage Forms," FDA's ACPS Meeting, Oct. 2005.
National Institute on Drug Abuse, Monitoring the Future, "National Results on Adolescent Drug Use—Overview of Key Findings 2009," http://www.monitoringthefuture.org/ (Originally Published in May, 2010).
National Institute on Drug Abuse, Monitoring the Future, "National Results on Adolescent Drug Use—Overview of Key Findings 2008," http://www.samhsa.gov/ (Originally Published in May, 2009).
National Institute of Drug Abuse, 2008 http://www.nida.nih.gov/dmgpages/prescription.html (Last Accessed on Jul. 15, 2008).
Roberts, et al., "Enterohepatic Circulation: Physiological, Pharmacokinetic and Clinical Implications." Clin. Pharmacokinet., vol. 41 Issue 10, pp. 751-790, (2002).
Supplemental Amendment filed Jul. 11, 2013, in U.S. Appl. No. 12/523,045.
Notice of Allowance issued Jun. 11, 2013, in U.S. Appl. No. 12/823,067.
Notice of Allowance issued Jul. 24, 2013, in U.S. Appl. No. 12/701,429.
Amendment after Notice of Allowance filed Aug. 26, 2013, in U.S. Appl. No. 12/701,429.
International Preliminary Report on Patentability issued Jul. 16, 2009 in corresponding International Application No. PCT/DK2008/000016, now WO 2008/086804.
International Preliminary Report on Patentability issued Aug. 6, 2011 in corresponding International Application No. PCT/EP2010/000728, now WO 2010/089132.
International Preliminary Report on Patentability issued Aug. 6, 2011 in corresponding International Application No. PCT/DK2010/000019, now WO 2010/088911.
Notification of Transmittal of the International Search Report and the Written Opinion of the International Searching Authority issued Jan. 28, 2009 in International Application No. PCT/US2008/056910.
Notification of Transmittal of the International Search Report and the Written Opinion of the International Searching Authority issued Feb. 6, 2010 in International Application No. PCT/DK2010/050016.
International Type Search Report issued Jun. 17, 2009 in International Application No. DK 2009001925.
Office Action issued Oct. 26, 2011 in U.S. Appl. No. 12/523,045, now US 2010/0291205.
Response to Oct. 26, 2011 Office Action filed Feb. 21, 2012 in co-pending U.S. Appl. No. 12/523,045, now US 2010/0291205.
Office Action issued May 24, 2012 in U.S. Appl. No. 12/523,045, now US 2010/0291205.
First Office Action issued Apr. 11, 2012 in U.S. Appl. No. 12/694,197, now US 2010/0203129.
Response to First Office Action filed Jul. 11, 2012 in U.S. Appl. No. 12/694,197, now US 2010/0203129.
First Office Action issued Nov. 14, 2011 in U.S. Appl. No. 12/823,067, now US 2011/0159100.
Response to Nov. 14, 2011 Office Action filed May 14, 2012 in co-pending U.S. Appl. No. 12/823,067, now US 2011/0159100.
Camu & Vanlersberghe, "Pharmacology of Systemic Analgesics." Best Practice and Research Clinical Anesthesiology, 2002; 16(4): 475-88.
Dahlstrom, et al., "Patient-Controlled Analgesic Therapy, Part IV: Pharmacokinetics and Analgesic Plasma Concentrations of Morphine." Clinical Pharmacokinetics, 1982; 7:266-79.
Graves et al., "Relationship Between Plasma Morphine Concentrations and pharmacologic Effects in Postoperative Patients Using Patient-Controlled Analgesia." Clinical Pharmacology, 1985; 4:41-7.
Haahr, et al. (Poster—Drug Abuse Resistant, Controlled Release using Egalet Dosage Units. Proceedings of the 34th Annual Meeting Exposition of the Controlled Release Society Jul. 7-11, 2007).
Hemmingsen, et al., "Drug Abuse Resistant, Controlled Release, Using Egalet Dosage Units" poster. Published Jun. 28, 2007.
Katikaneni, et al. Ethylcellulose Matrix controlled Release Tablets of a Water-Soluable Drug. International Journal of Pharmaceutics 123 pp. 119-125 1995.
L. Qui, et al., "Design Core-Shelled Polymer Cylinder for Potential Programmable Drug Delivery." Int. J. Pharm., 2001; 219:151-160.
Raehhal & Bohn, "Mu Opioid Receptor Regulation and Opiate Responsiveness." The AAPS Journal 2005; 7(3): Article 60.
(www.rxlist.com/miralax-drug.htm) as referenced Oct. 19, 2011.
Office Action issued Dec. 17, 2012 in co-pending U.S. Appl. No. 12/701,429, now US 2010/0203130.
Response to First Office Action filed Mar. 13, 2013 in in co-pending U.S. Appl. No. 12/701,429, now US 2010/0203130.
Response to May 24, 2012 Office Action filed Aug. 7, 2012 in U.S. Appl. No. 12/523,045, now US 2010/0291205.
Interview Summary issued Dec. 14, 2012 in U.S. Appl. No. 12/523,045, now US 2010/0291205.
First Office Action issued Mar. 7, 2013 in co-pending U.S. Appl. No. 12/602,953, now US 2010/0239667.
Final Office Action issued Sep. 14, 2012 in co-pending U.S. Appl. No. 12/694,197, now US 2010/0203129.
Response to Final Office Action filed Mar. 13, 2013 in co-pending U.S. Appl. No. 12/694,197, now US 2010/0203129.

(56) References Cited

OTHER PUBLICATIONS

Final Office Action issued Sep. 10, 2012 in U.S. Appl. No. 12/823,067, now US 2011/0159100.
Interview Summary issued Dec. 20, 2012 in U.S. Appl. No. 12/823,067, now US 2011/0159100.
Response to Sep. 10, 2012 Final Office Action filed Jan. 10, 2013 in U.S. Appl. No. 12/823,067, now US 2011/0159100.
Brannan, et al. (Geometry 2nd Edition. Cambridge University Press: NY; 2012 p. 78).
U.S. Appl. No. 13/900,933, filed Aug. 25, 2006, Purdue Pharma C.
Bravo et al., "In-vitro studies of diclofenac sodium controlled-release from biopolymeric hydrophilic matrices," *J. Pharmaceutical Science*, vol. 5, No. 3, pp. 213-219 (2002).
The Condensed Chemical Dictionary, "mixture," 9th edition, p. 584 (1977).
Giunchedi et al., "Hydrophilic matrices for the extended release of a model drug exhibiting pH-dependent solubility," *International Journal of Pharmaceutics*, vol. 85, pp. 141-147 (1992).
Miyazaki et al., "In situ-gelling gellan formulations as vehicles for oral drug delivery," *J. Control Release*, vol. 60, pp. 287-295 (1999).
Rowe et al., "Glycerin," *Handbook of Pharmaceutical Excipients*, Pharmaceutical Presse, 4$^{th}$ edition, pp. 257-258 (2003).
Yamakita et al., "In Vitro/in Vivo Evaluation of Two Series of TA5707F Controlled Release Matrix Tablets Prepared with Hydroxypropyl Methyl Cellulose Derivatives with Entero-Soluble or Gel-Formation Properties," *Biol. Pharm. Bull*, vol. 18, No. 10, pp. 1409-1416 (1995).
Marvola et al., "Enteric polymers as binders and coating materials in multiple-unit site-specific drug delivery systems," *European Journal of Pharmaceutical Sciences*, vol. 7, pp. 259-267, 1999.
Varshosaz et al., "Use of enteric polymers for production of microspheres by extrusion-spheronization," *Pharmaceutica Acta Helvetiae*, vol. 72, pp. 145-152. 1997.
Wanka et al., "Phase Diagrams and Aggregation Behavior of Poly(oxyethylene)-Poly(oxypropylene)-Poly(oxyethylene) Triblock Copolymers in Aqueous Solutions," vol. 27, pp. 4145-4159, 1994.
Katikaneni et al., "Ethylcellulose matrix controlled release tablets of a water-soluble drug," International Journal of Pharmaceutics, vol. 123, pp. 119-125, 1995.
Polysciences, Inc., "Monomers & Polymers," http://www.polysciences.com/Catalog/Department/Product/98/categoryid-298/productid--422/, published Apr. 3, 2004.

* cited by examiner

IMMEDIATE RELEASE COMPOSITION RESISTANT TO ABUSE BY INTAKE OF ALCOHOL

This application claims the benefit of priority of U.S. Provisional Application No. 61/150,577, filed Feb. 6, 2009; and the benefit of priority of U.S. Provisional Application No. 61/151,491, filed Feb. 10, 2009. This application also claims priority of Denmark Patent Application No. PA 2009 00190, Feb. 6, 2009.

All patent and non-patent references cited in the application are hereby incorporated by reference in their entirety.

FIELD OF THE INVENTION

Pharmaceutical compositions that are suitable for oral administration and resistant to abuse by the intake of alcohol are described herein. In particular embodiments, the compositions are matrix compositions or coated matrix compositions, wherein the matrix compositions comprise one or more low molecular weight polyglycols combined with one or more effervescent agents.

BACKGROUND OF THE INVENTION

In recent years, the abuse of prescription and over-the-counter (OTC) pharmaceutical products has become a concerning trend. For example, in some instances, potential abusers simultaneously ingest one or more prescription or over-the-counter pharmaceuticals in combination with alcohol in order to increase the effect of the alcohol and/or the specific drug substances contained in the pharmaceutical product. In particular, certain pharmaceutical products for oral administration release the drug substance contained therein at a faster rate in the presence of alcohol and, accordingly, the drug substance is available for absorption at a faster rate than intended by the manufacturer. Such a faster release rate may lead to unwanted and potentially dangerous effects.

An unintended rapid release of all or a significant fraction of a drug substance contained within a pharmaceutical composition over a short period of time is often referred to as "dose dumping". In the context of modified-release pharmaceutical compositions (e.g., sustained or controlled release pharmaceutical compositions), which are often formulated to include relatively high amounts of drug substance in order to preserve a therapeutic benefit over an extended period of time, some compositions have been reported to contain drug substances and excipients that exhibit higher solubility in ethanolic solutions than in aqueous solutions that are free of ethanol. Such compositions have the potential to exhibit relatively high rates of drug dissolution and increased release rates of drug substance in the presence of ethanol. Therefore, consumption of alcoholic beverages in combination with modified-release compositions that exhibit increase release rates of drug substance in the presence of ethanol has the potential to induce dose dumping, which may increase the ease with which such modified-release compositions can be abused. However, the potential problems resulting from dose dumping in the presence of ethanol are not limited to modified-release compositions. Conventional oral compositions (e.g., immediate release compositions dosage forms) may also exhibit dose dumping behaviour in the presence of ethanol, which, in turn, can result in even more rapid delivery and uptake of the drug substance or easier isolation of the drug substance from formulation excipients and/or other inactive constituents included in the pharmaceutical product.

In the 1990s, the U.S. Food and Drug Administration (FDA) required that certain OTC pain relievers and fever reducers carry a warning label advising consumers who consume three or more alcoholic drinks every day to consult a physician before using such products. FDA issued this final rule after considering public comments and data on the effects of combining chronic alcohol ingestion and the use of various OTC analgesics. The action also followed the recommendations of the Nonprescription Drugs Advisory Committee and the Arthritis Drugs Advisory Committee, which concluded that chronic alcohol users should be warned that they may be at an increased risk of liver damage or stomach bleeding from use of these drugs. Drug substances affected by this labelling requirement include, for example, aspirin, other salicylates, acetaminophen, ibuprofen, naproxen sodium, and ketoprofen.

FIGURES

FIG. 1. PEG 3350S without disintegrant or effervescence. Dissolution-profiles % release versus time in minutes (n=3) in HCl solution-buffer (pH 1.2) and 40% (v/v) alcohol/pH 1.2.

Figure 2:
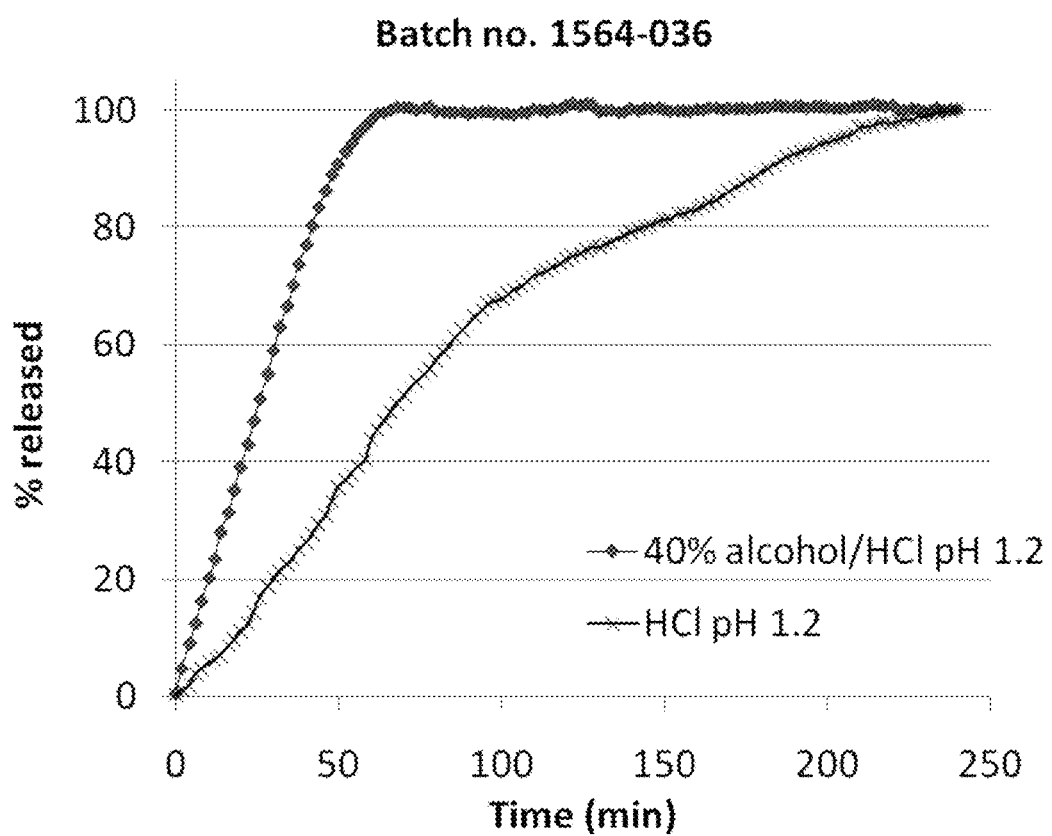

FIG. 2. PEG 6000 without disintegrant or effervescence. Dissolution-profiles % release versus time in minutes (n=3) in HCl solution (pH 1.2) and 40% (v/v) alcohol/pH 1.2.

Figure 3:
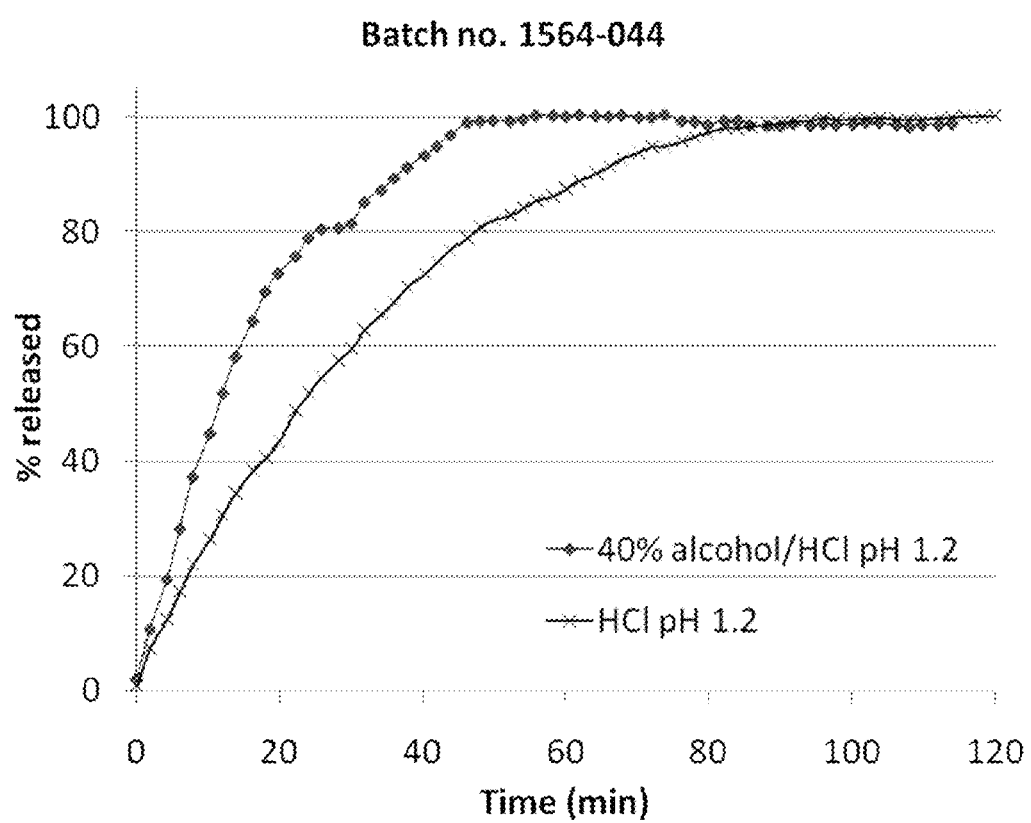

FIG. 3. PEG 17,000 without disintegrant or effervescence. Dissolution-profiles % release versus time in minutes (n=3) in HCl solution (pH 1.2) and 40% (v/v) alcohol/pH 1.2.

Figure 4:
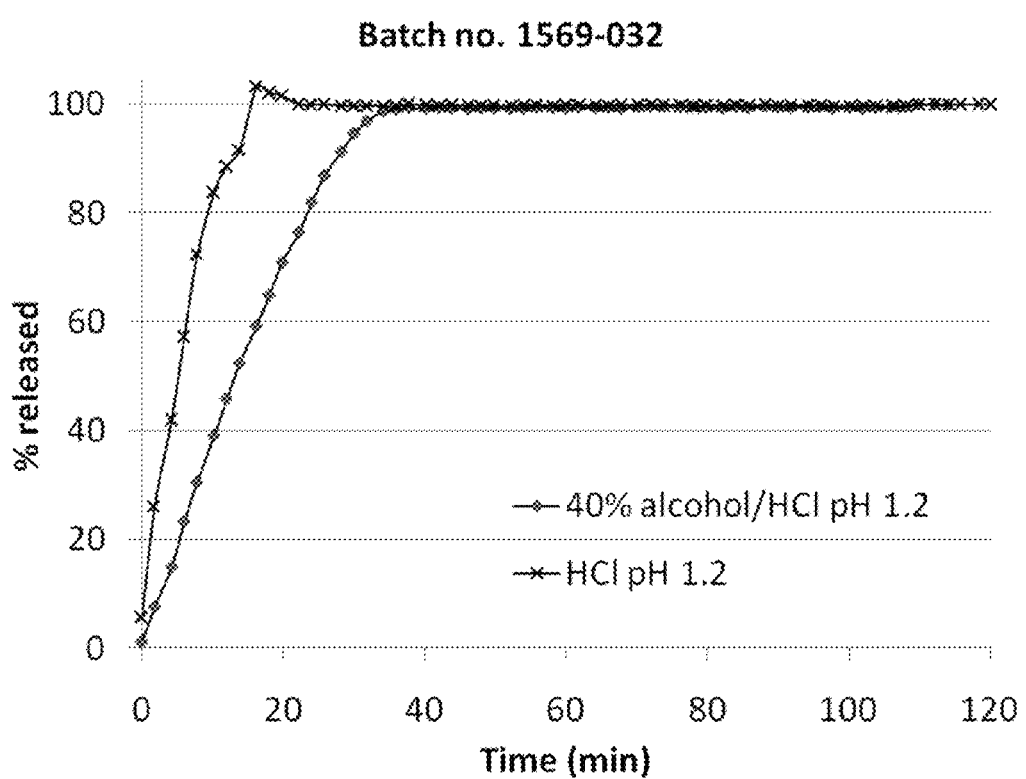

FIG. 4. PEG 3350 with a combination of 2% citric acid and 5% $NaHCO_3$ as effervescent agent. Dissolution-profiles % release versus time in minutes (n=3) in HCl solution (pH 1.2) and 40% (v/v) alcohol/pH 1.2.

Figure 5:
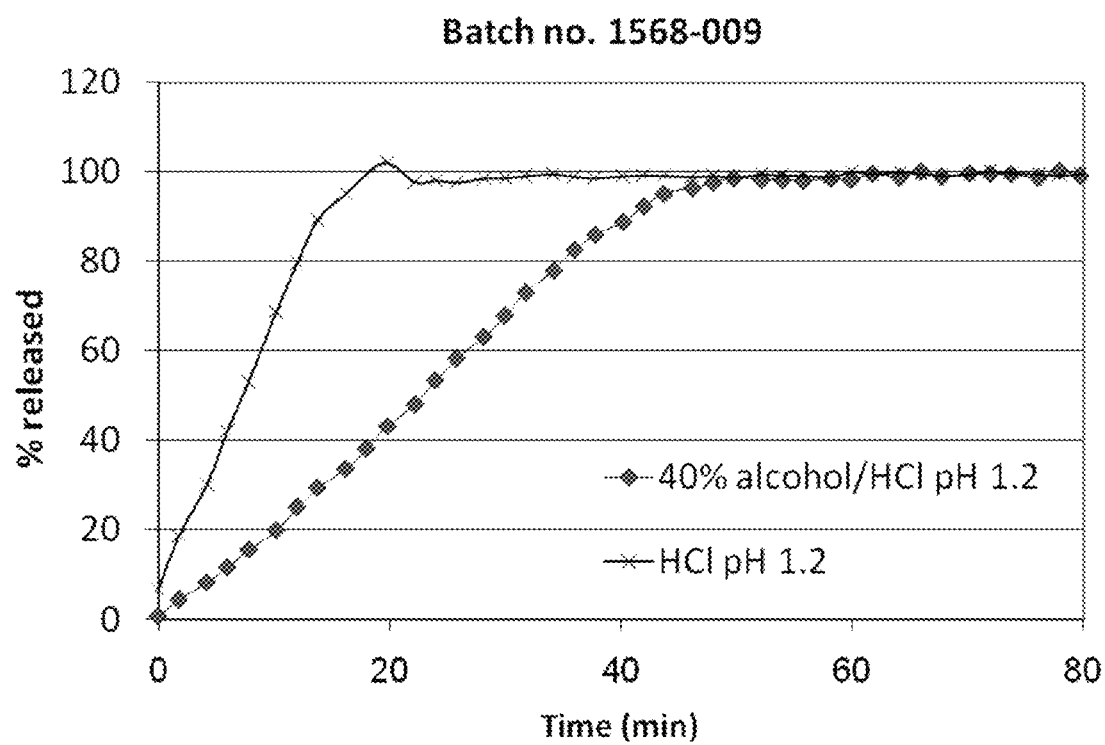

FIG. 5. PEG 6000 with a combination of 2% citric acid and 5% $NaHCO_3$ as effervescent agent. Dissolution-profiles % release versus time in minutes (n=3) in HCl solution (pH 1.2) and 40% (v/v) alcohol/pH 1.2.

Figure 6:
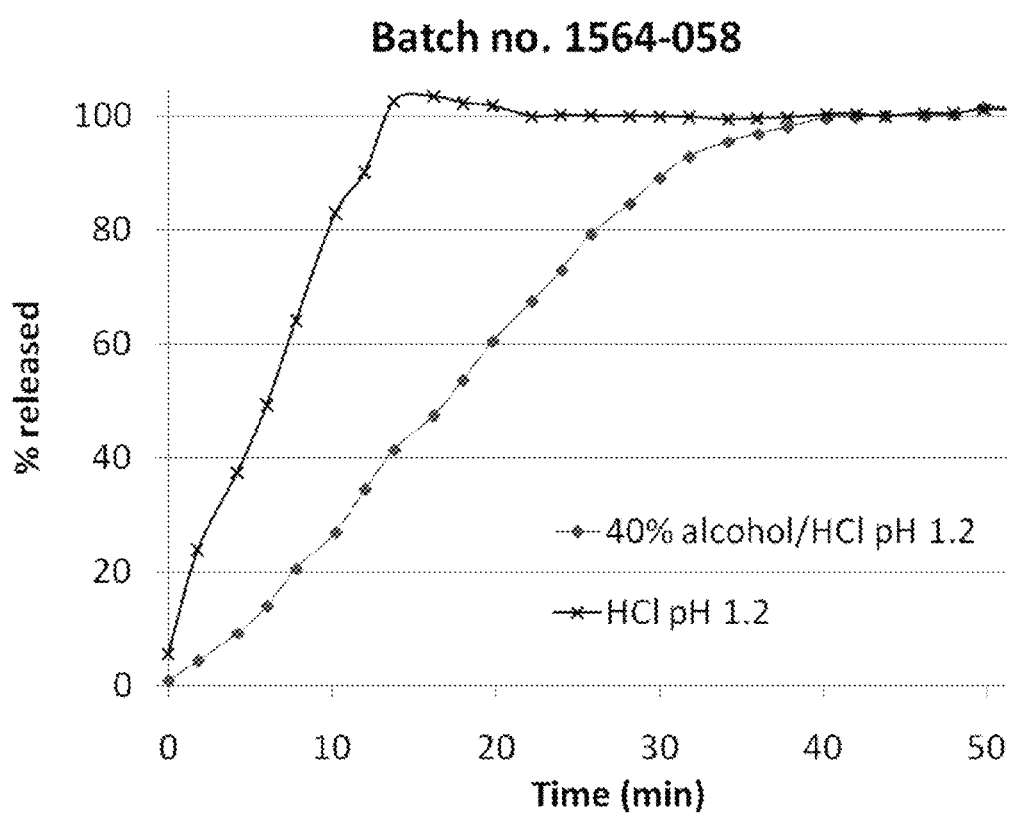

FIG. 6. PEG 17,000 with a combination of 4% citric acid and 10% $NaHCO_3$ as effervescent agent. Dissolution-profiles % release versus time in minutes (n=3) in HCl solution (pH 1.2) and 40% (v/v) alcohol/pH 1.2.

Figure 7:
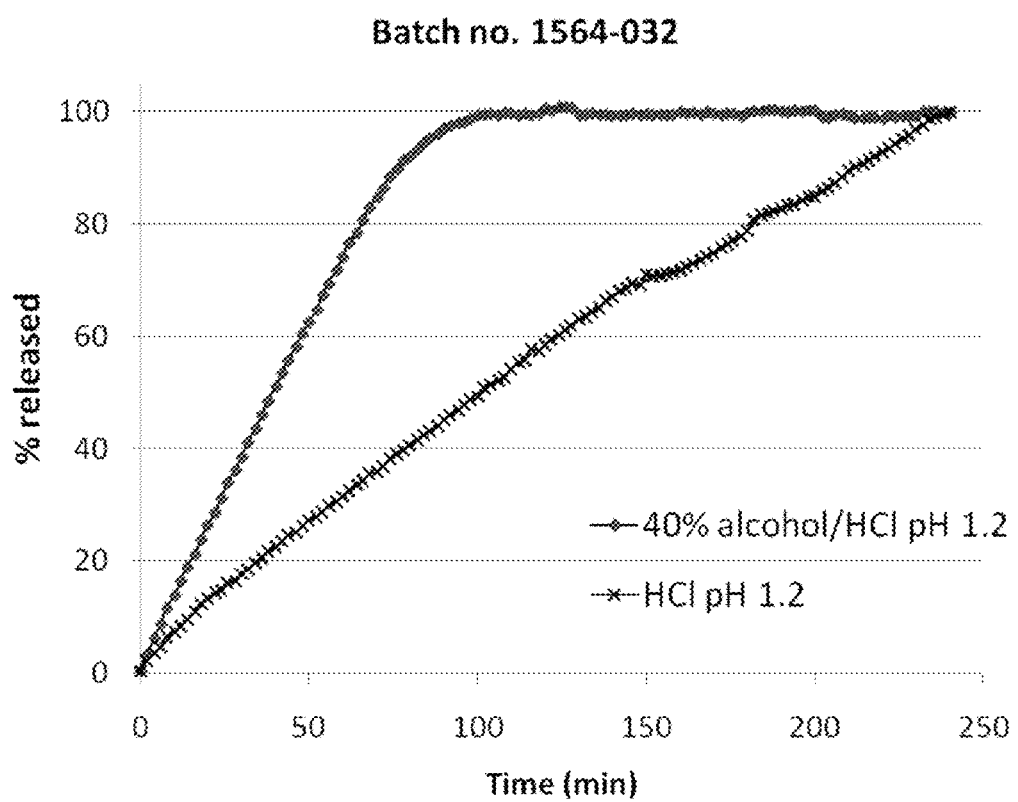

FIG. 7. PEG 6000 with 10% Cross-caramellose Na as disintegrant. Dissolution-profiles % release versus time in minutes (n=3) in HCl solution (pH 1.2) and 40% (v/v) alcohol/pH 1.2.

Figure 8:
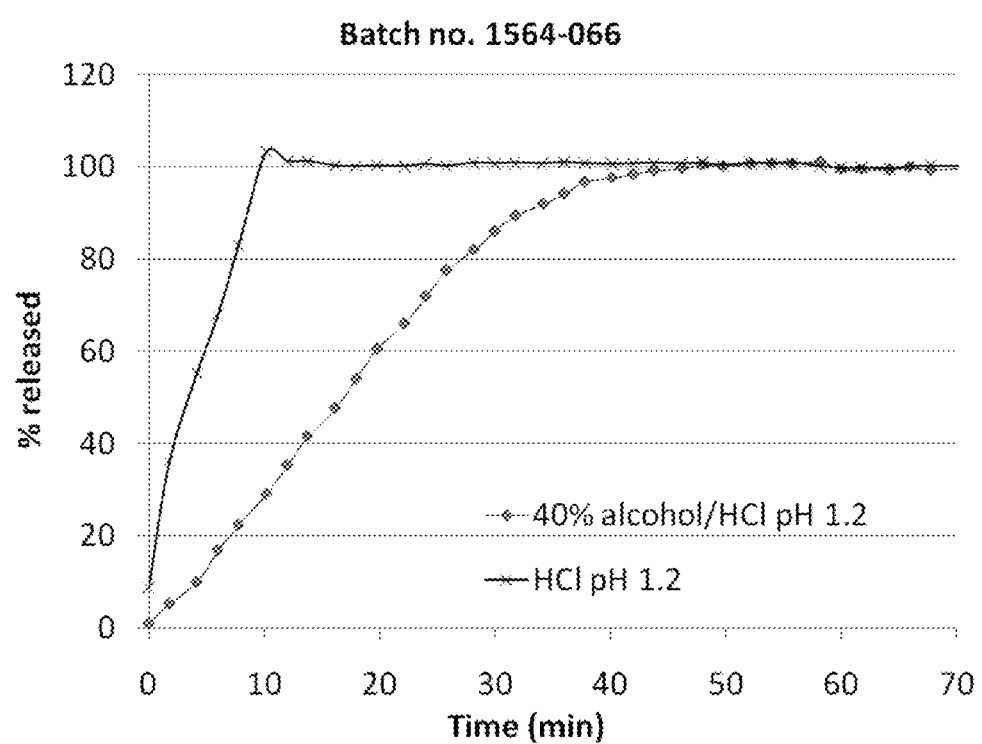

FIG. 8. PEG 17,000 with a combination of 4% citric acid and 10% $NaHCO_3$ as effervescent agent and 5% Cross-caramellose Na as disintegrant. Dissolution-profiles % release versus time in minutes (n=3) in HCl solution (pH 1.2) and 40% (v/v) alcohol/pH 1.2.

Figure 9:
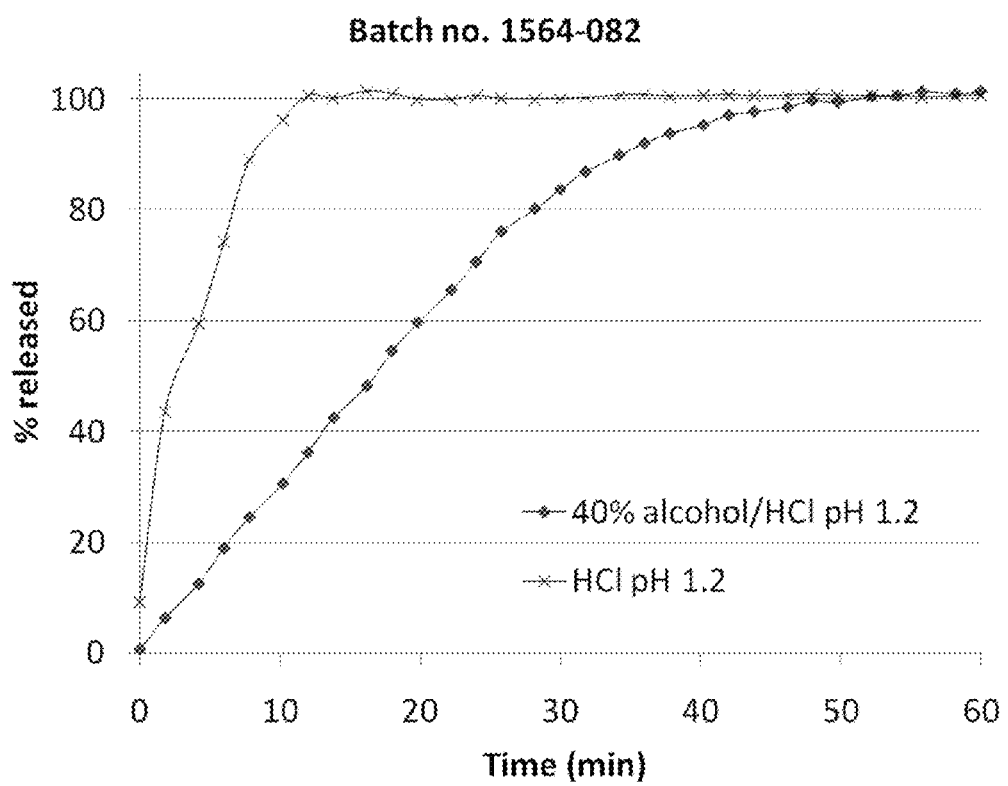

FIG. 9. PEG 14,000 with a combination of 3% citric acid and 7.5% $NaHCO_3$ as effervescent agent and 12.5% Cross-caramellose Na as disintegrant. Dissolution-profiles % release versus time in minutes (n=3) in HCl solution (pH 1.2) and 40% (v/v) alcohol/pH 1.2.

Figure 10:
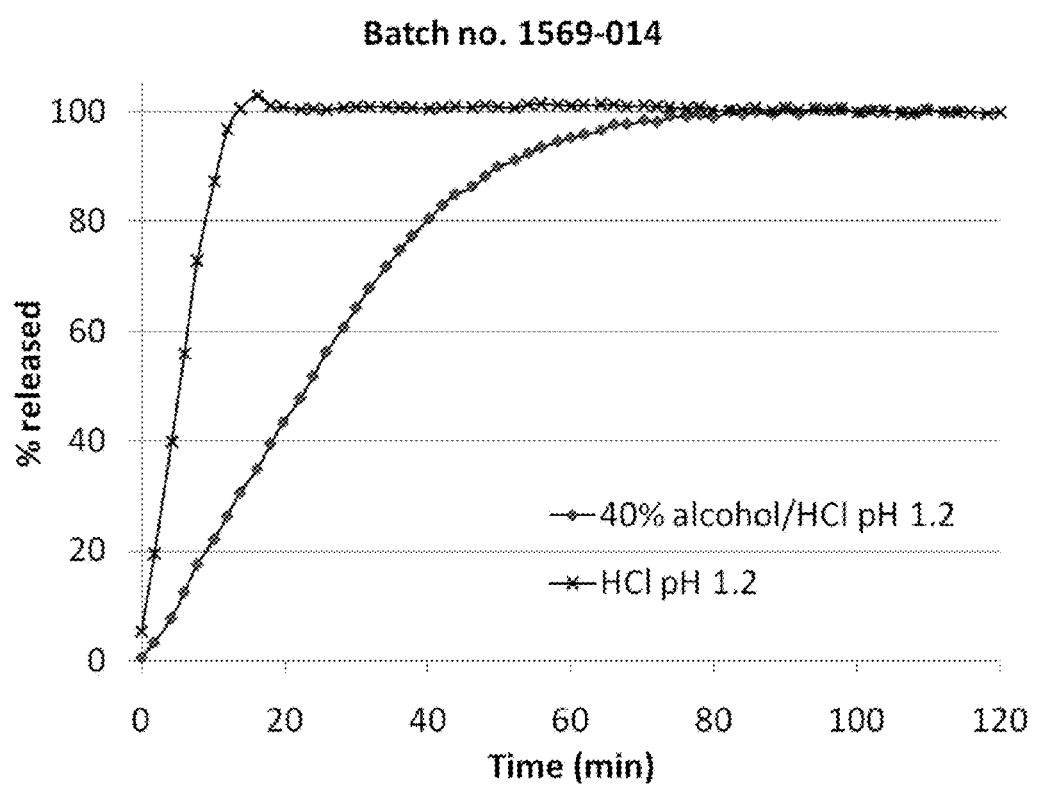

FIG. 10. PEG 10,000 with a combination of 2.5% citric acid and 6.25% $NaHCO_3$ as effervescent agent and 12.5% Cross-caramellose Na as disintegrant. Dissolution-profiles % release versus time in minutes (n=3) in HCl solution (pH 1.2) and 40% (v/v) alcohol/pH 1.2.

Figure 11:
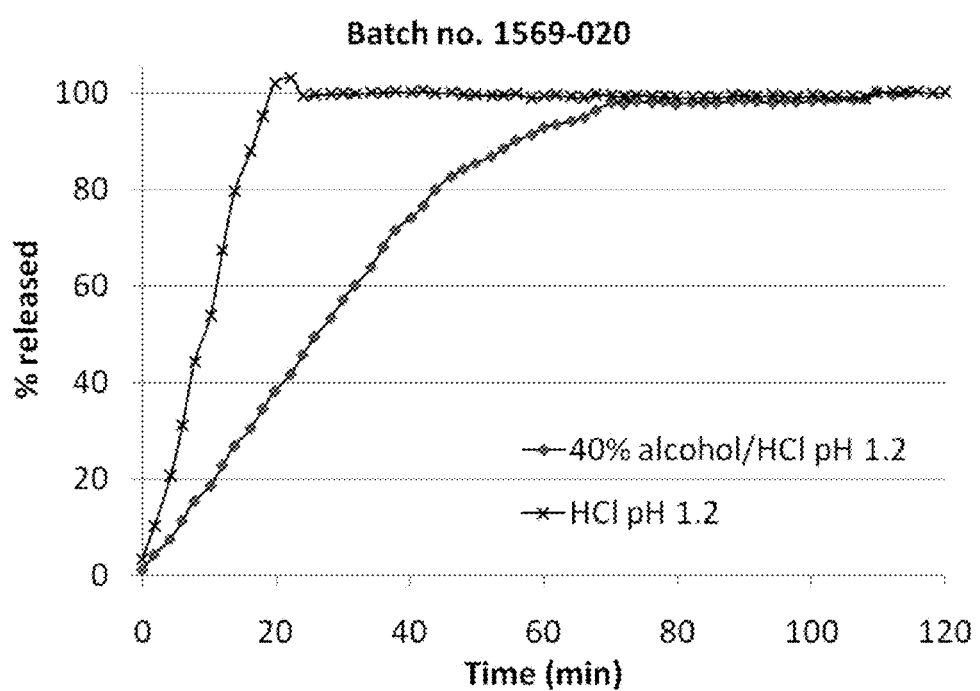

FIG. 11. PEG 6000 with a combination of 2% citric acid and 5% $NaHCO_3$ as effervescent agent and 12.5% Cross-caramellose Na as disintegrant. Dissolution-profiles % release versus time in minutes (n=3) in HCl solution (pH 1.2) and 40% (v/v) alcohol/pH 1.2.

Figure 12:
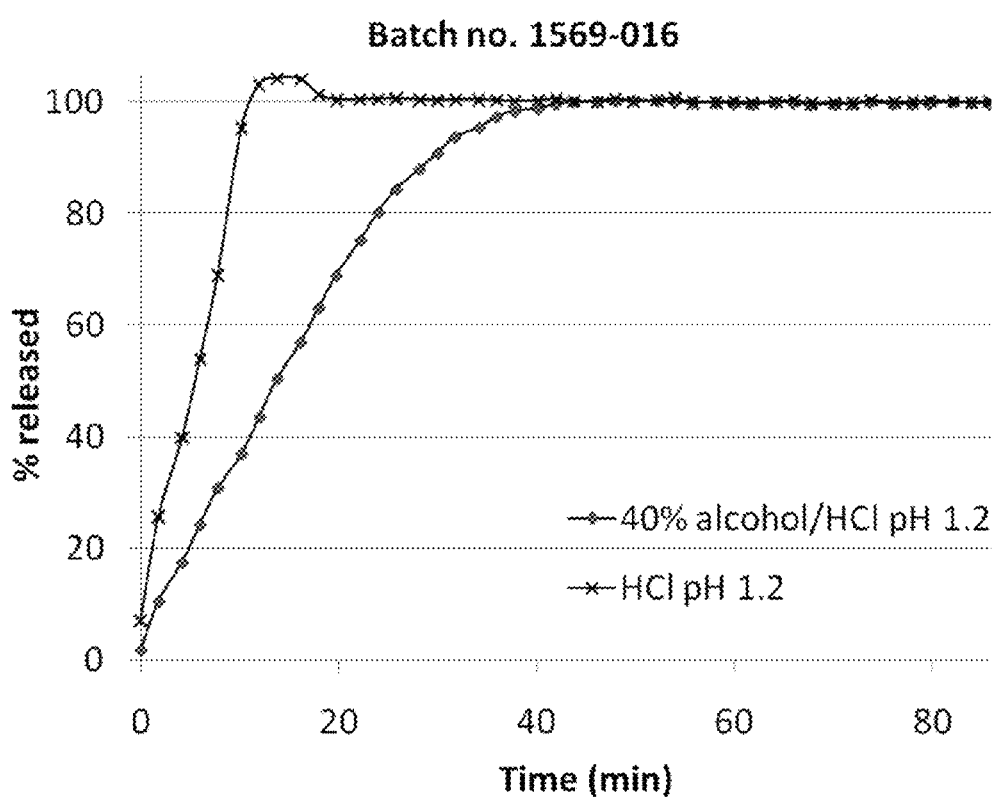

FIG. 12. PEG 3350 with a combination of 2% citric acid and 5% $NaHCO_3$ as effervescent agent and 12.5% Cross-caramellose Na as disintegrant. Dissolution-profiles % release versus time in minutes (n=3) in HCl solution (pH 1.2) and 40% (v/v) alcohol/pH 1.2.

Figure 13:
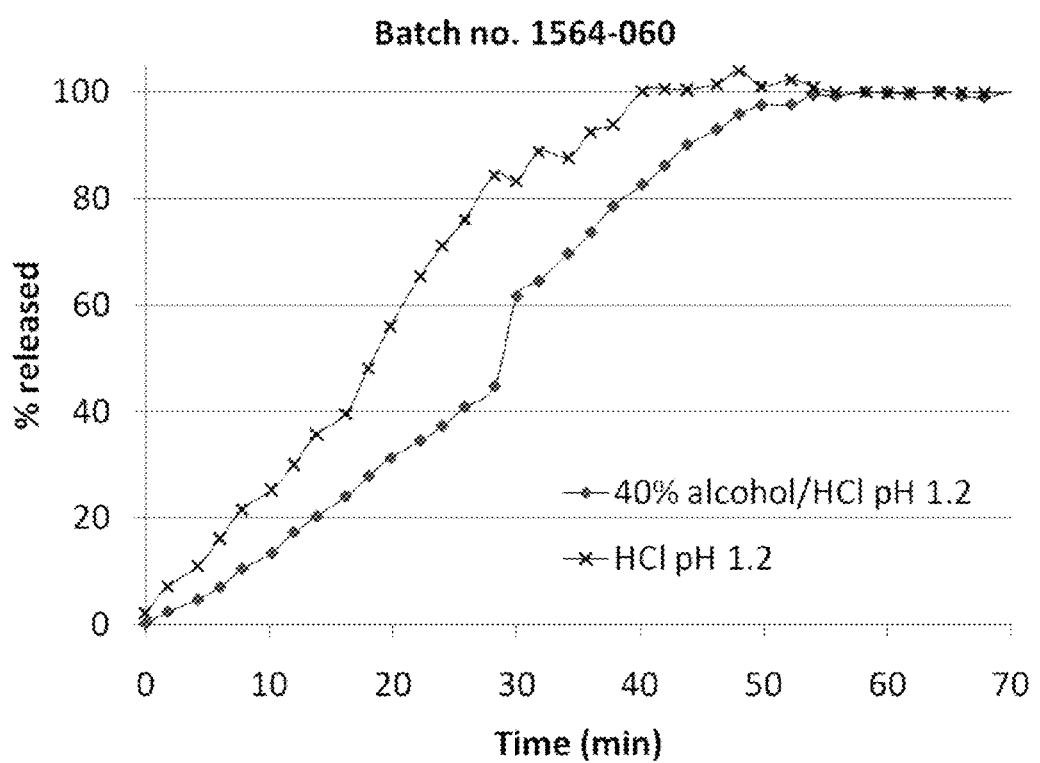

FIG. 13. PEG 6000 with a combination of 2% tartaric acid and 5% NaHCO$_3$ as effervescent agent. No disintegrant added. Dissolution-profiles % release versus time in minutes (n=3) in HCl solution (pH 1.2) and 40% (v/v) alcohol/pH 1.2.

Figure 14:
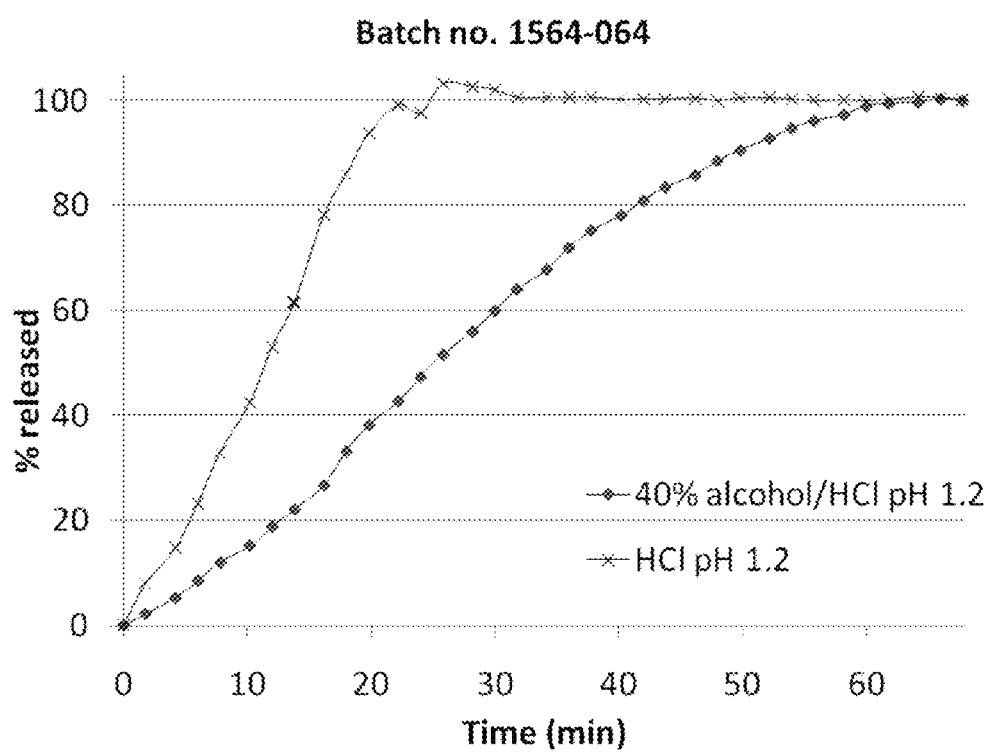

FIG. 14. PEG 6000 with a combination of added 4% tartaric acid and 5% NaHCO$_3$ as effervescent agent. No disintegrant added. Dissolution-profiles % release versus time in minutes (n=3) in HCl solution (pH 1.2) and 40% (v/v) alcohol/pH 1.2.

Figure 15:
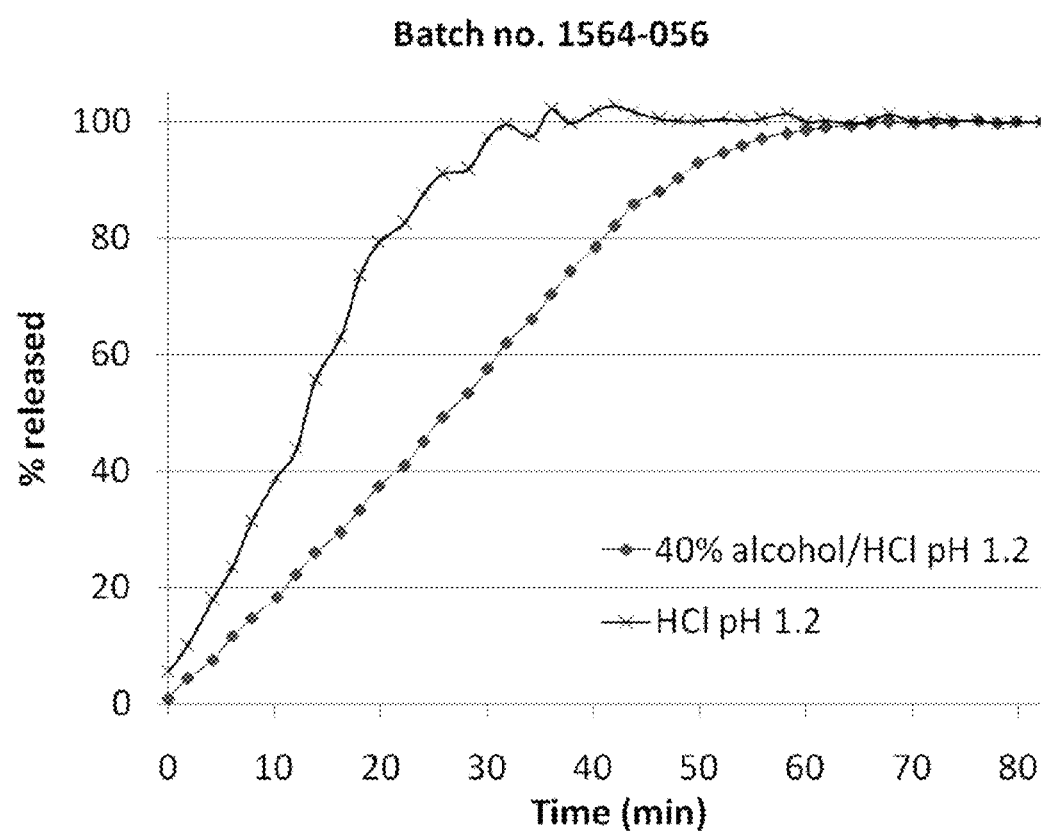

FIG. 15. PEG 6000 with a combination of added 2% succinic acid and 5% NaHCO$_3$ as effervescent agent. No disintegrant added. Dissolution-profiles % release versus time in minutes (n=3) in HCl solution (pH 1.2) and 40% (v/v) alcohol/pH 1.2.

Figure 16:
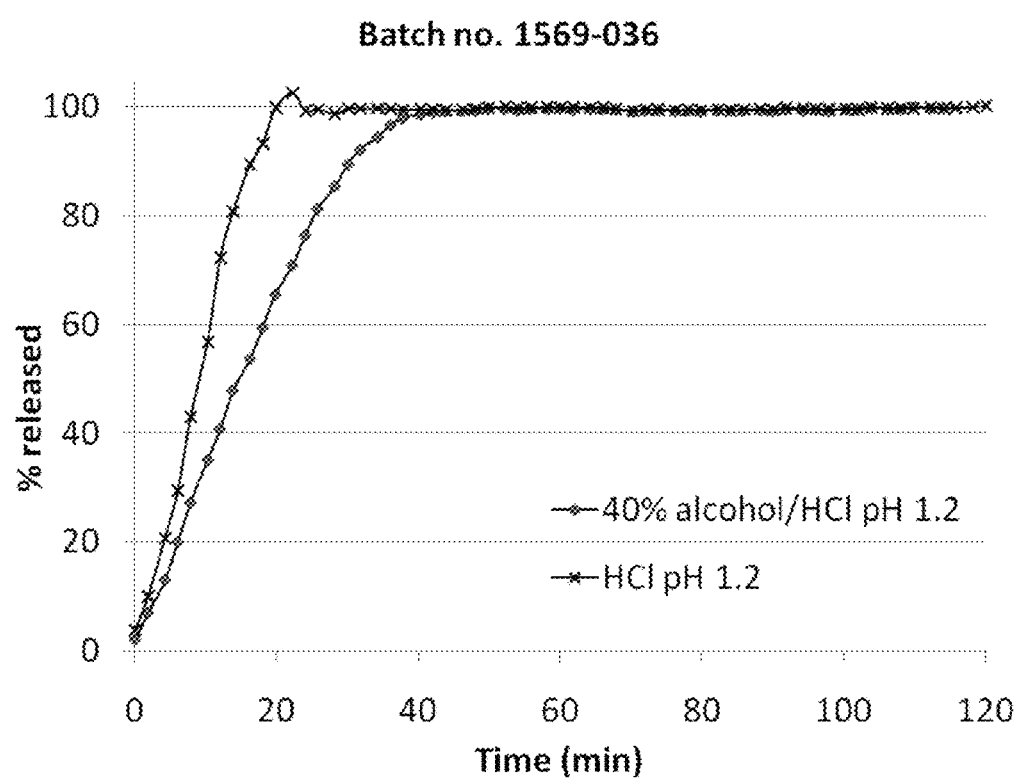

FIG. 16. PEG 6000 with a combination of added 4% malonic acid and 5% NaHCO$_3$ as effervescent agent. No disintegrant added. Dissolution-profiles % release versus time in minutes (n=3) in HCl solution (pH 1.2) and 40% (v/v) alcohol/pH 1.2.

Figure 17:
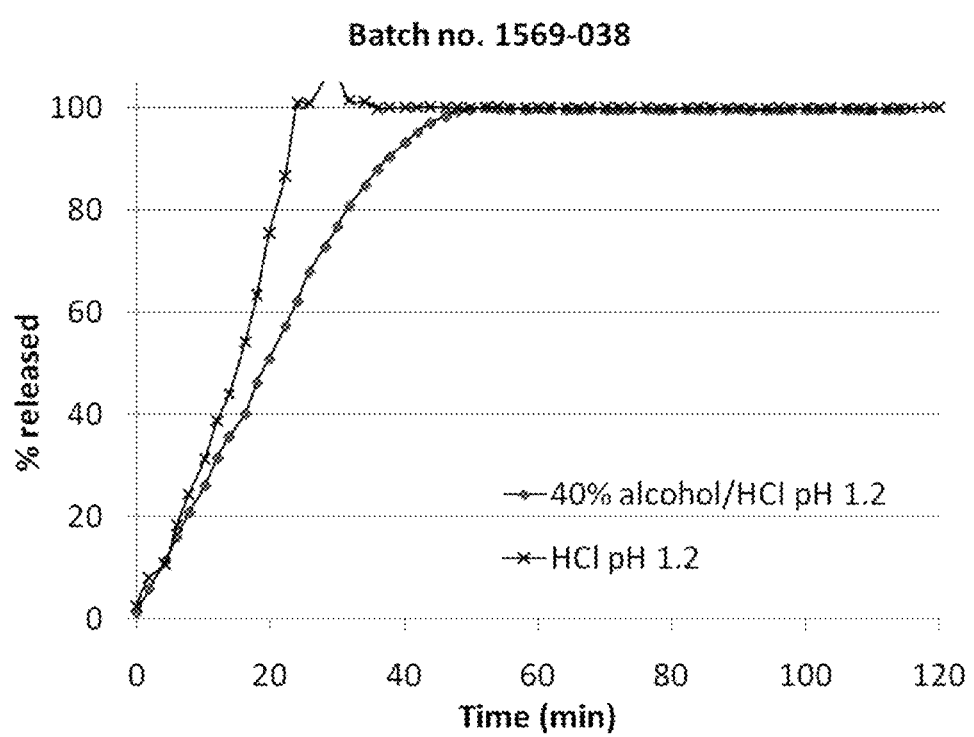

FIG. 17. PEG 6000 with a combination of added 4% benzoic acid and 5% NaHCO$_3$ as effervescent agent. No disintegrant added. Dissolution-profiles % release versus time in minutes (n=3) in HCl solution (pH 1.2) and 40% (v/v) alcohol/pH 1.2.

Figure 18:
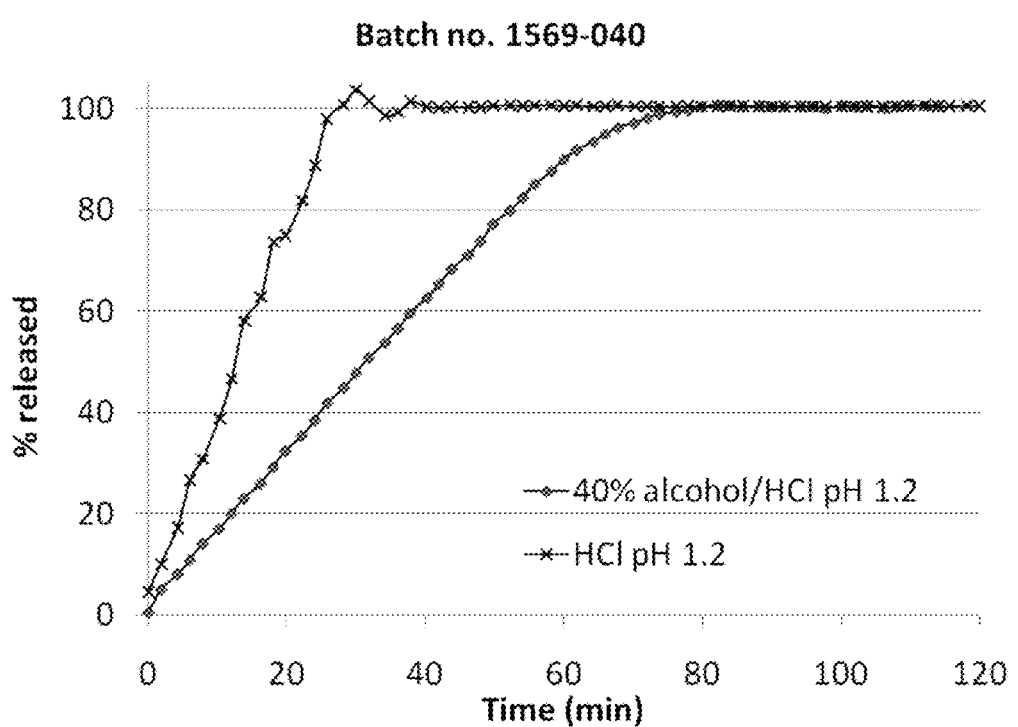

FIG. 18. PEG 6000 with a combination of added 4% Oxalic acid and 5% NaHCO$_3$ as effervescent agent. No disintegrant added. Dissolution-profiles % release versus time in minutes (n=3) in HCl solution (pH 1.2) and 40% (v/v) alcohol/pH 1.2.

Figure 19:
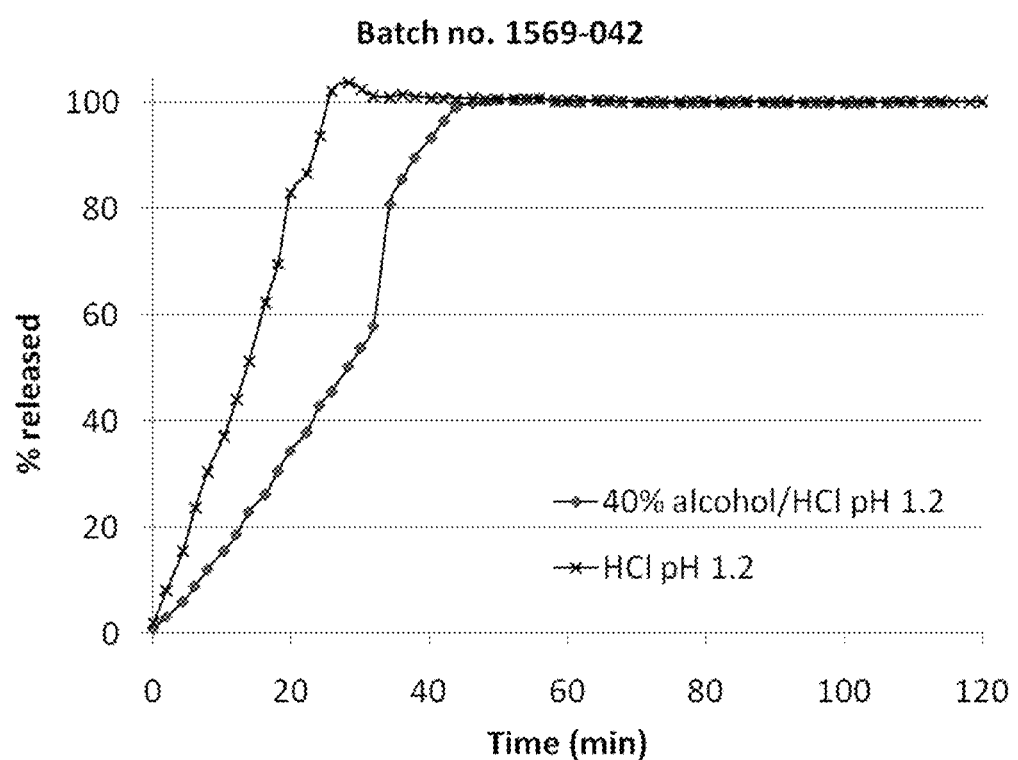

FIG. 19. PEG 6000 with a combination of added 4% Malic acid and 5% NaHCO$_3$ as effervescent agent. No disintegrant added. Dissolution-profiles % release versus time in minutes (n=3) in HCl solution (pH 1.2) and 40% (v/v) alcohol/pH 1.2.

Figure 20:
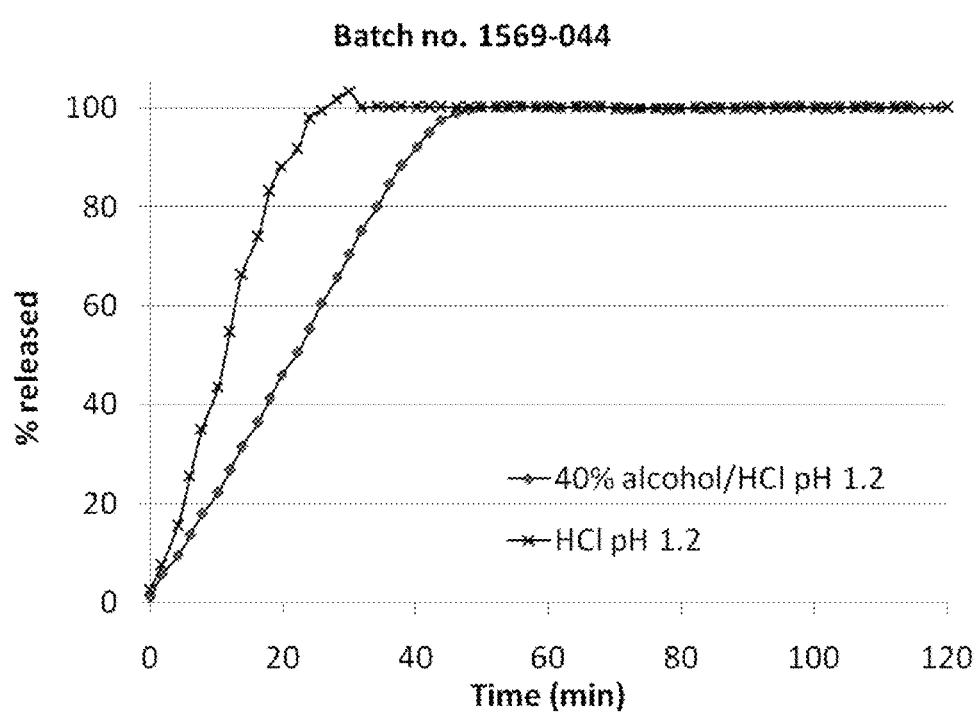

FIG. 20. PEG 6000 with a combination of added 4% glutaric acid and 5% NaHCO$_3$ as effervescent agent. No disintegrant added. Dissolution-profiles % release versus time in minutes (n=3) in HCl solution (pH 1.2) and 40% (v/v) alcohol/pH 1.2.

Figure 21:
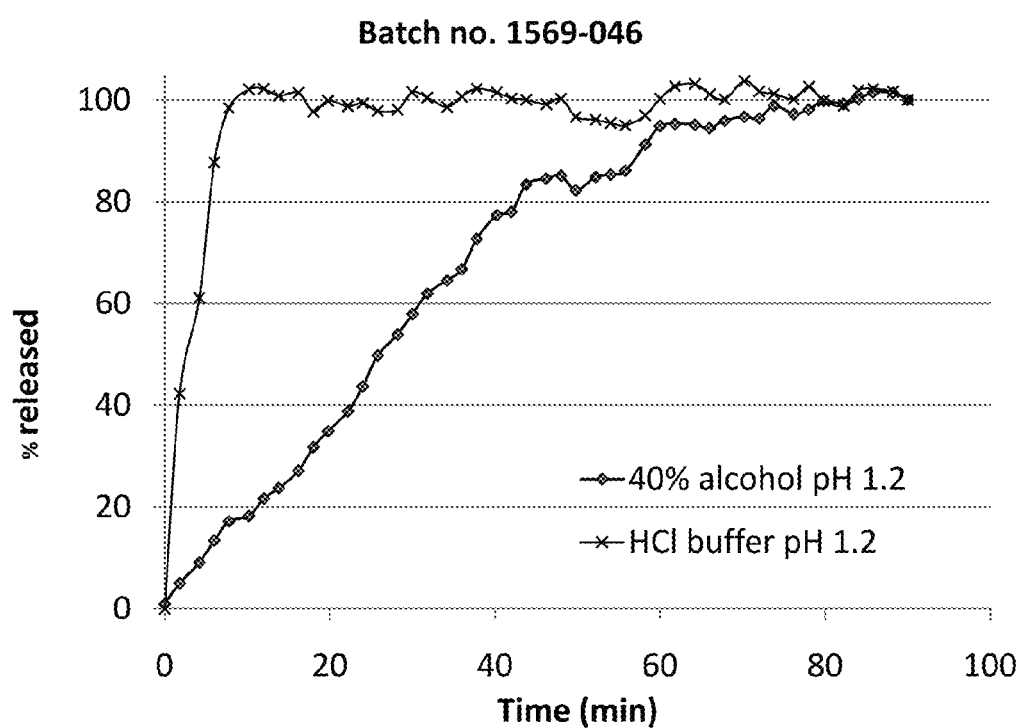

FIG. 21. PEG 6,000 with a combination of 2.5% citric acid and 6.25% NaHCO$_3$ as effervescent agent and 12.5% Cross-caramellose Na as disintegrant. Dissolution-profiles % release versus time in minutes (n=3) in HCl solution (pH 1.2) and 40% (v/v) alcohol/pH 1.2.

Figure 22:
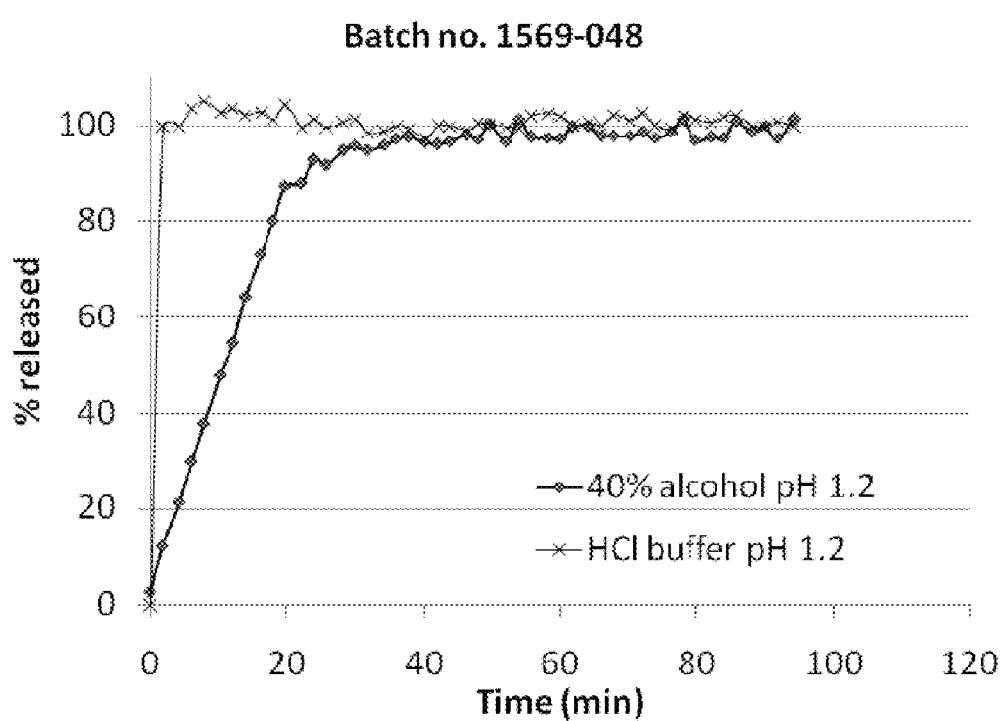

FIG. 22. PEG 6,000 with a combination of 6% citric acid and 15% NaHCO$_3$ as effervescent agent and 12.5% Cross-caramellose Na as disintegrant. Dissolution-profiles % release versus time in minutes (n=3) in HCl solution (pH 1.2) and 40% (v/v) alcohol/pH 1.2.

Figure 23:
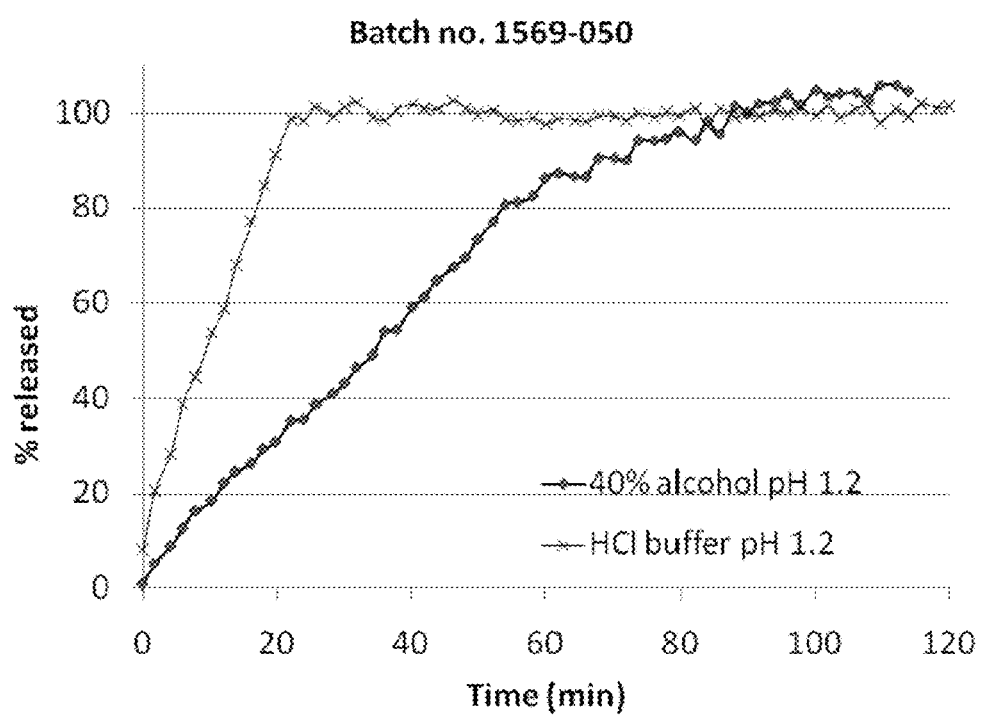

FIG. 23. PEG 17,000 with a combination of 2.5% citric acid and 6.25% NaHCO$_3$ as effervescent agent and 12.5% Cross-caramellose Na as disintegrant. Dissolution-profiles % release versus time in minutes (n=3) in HCl solution (pH 1.2) and 40% (v/v) alcohol/pH 1.2.

DISCLOSURE OF THE INVENTION

Immediate release compositions for the delivery of drug substances and methods of using the same are described herein. In specific embodiments, the immediate release compositions described herein exhibit a decreased release rate of drug substance in the presence of ethanol. For example, in one such embodiment, the release of the drug substance from the immediate release composition is decreased when the composition is exposed to a dissolution medium that includes ethanol. In one such embodiment, when compared to the release rate in a dissolution medium free of ethanol, an immediate release composition as described herein exhibits a decreased release rate of drug substance when exposed to a dissolution medium containing 40% v/v ethanol. In specific embodiments, the solubility of the immediate release composition and/or the release rate of the drug substance from the immediate release composition in an aqueous media that is free of ethanol is selected from at least 1.5 times higher, at least 2 times higher, at least 5 times higher, at least 10 times higher, at least 25 times higher, at least 50 times higher or at least 100 times higher than the dissolution and/or release rate exhibited in a dissolution medium containing 40% v/v ethanol, as measured in the in vitro dissolution test described herein.

In specific embodiments, the immediate release compositions described herein may be formulated with constituents and manufactured in a manner that results in a pharmaceutical composition exhibiting resistance to crushing (i.e., exhibiting a relatively high hardness). In one such embodiment, immediate release compositions according to the present description may be manufactured using an injection moulding or heat extrusion process. In another such embodiment, immediate release compositions according to the present description may be manufactured in the form of compressed tablets.

Compositions described herein may be formulated to include at least one polyglycol and at least one effervescent agent. For example, a composition according to the present description may include at least one polyglycol having a molecular weight of from about 900 to about 17,000 Daltons at a concentration of at least 5% w/w, one or more effervescent agents, and, optionally, one or more disintegrants.

Whenever an amount is recited herein, it is understood that the amount may also be recited with terms of approximation such as "about" or "approximately." For example, a disclosure regarding a definite numerical amount such as "an amount of 1 unit" can also be substituted by an approximate amount such as "about 1 unit." As another example, a disclosure regarding a numerical range that is recited with definite endpoints such as "an amount ranging from 1 unit to 2 units" can also be substituted by a range with approximate endpoints such as "an amount ranging from about 1 unit to about 2 units." It is also understood that the use of the term "about" may be used to account for variations due to experimental errors.

Methods suitable for preparing an immediate release composition as describe herein include injection moulding and heat extrusion. Tableting, such as by known compression techniques and tableting machines, is also a suitable method for preparing such compositions. Where the immediate release compositions are prepared by means of either injection moulding or heat extrusion, the nature of the polyglycols available for use in the composition may be determined by their melting point as the final composition should be in solid form. The immediate release composition described herein may be prepared as matrix compositions, wherein the drug substance is dispersed in the matrix. The use of polyglycols with a molecular weight of from about 20,000 and above for the preparation of a controlled release pharmaceutical composition has been described in, for example, WO 89/09066, WO 91/004015, WO 95/22962, WO 99/51208, WO 03/024429, WO 03/024426, WO 03/024430, WO 2004/041252, WO 2004/084869, WO 2004/084868, WO 2006/128471, WO 2008/086804, WO 2008/148798.

In contrast to references teachings the composition and manufacture of controlled release pharmaceutical compositions, the present invention provides compositions for immediate release of one or more drug substances. In particular embodiments, the compositions described herein are formulated to reduce the potential for abuse of such composition through exposure of such composition to ethanol. For example, in certain such embodiments, the compositions described herein may be formulated to exhibit a release rate of drug substance that is lower in an aqueous dissolution media that includes ethanol when compared to the release rates achieved in an aqueous dissolution media free of ethanol. Moreover, the immediate release compositions described herein may be formulated to resist crushing, such as by chewing. Embodiments of abuse resistant, immediate release compositions described herein include a polyglycol having a molecular weight of from 900 to 17,000 Daltons at a concentration of about 5% w/w or more, a drug substance, one or more effervescent agents, and, optionally, one or more disintegrants.

In a specific embodiments, the immediate release compositions resistant to abuse by the intake of alcohol may be prepared using a polyglycol having a molecular weight of from about 900 to about 17,000 Daltons, a drug substance, one or more effervescent agents, and, optionally, one or more disintegrants. In such embodiments, the release rate of drug substance delivered from the immediate release composition is decreased when the immediate release composition is ingested with an alcohol, such as may be present in, for example, an alcoholic beverage or certain pharmaceutical compositions. In a further embodiment, said immediate release composition is formulated to exhibit a hardness that renders the composition resistant to crushing.

In particular embodiments, the immediate release compositions described herein are resistant to abuse by intake of alcohol when said alcohol is ingested either:
a. together with the immediate release composition; or
b. within a period of up to 60 minutes before and up to 60 minutes after ingesting the composition.

In such embodiments, when compared to the release rate achieved in an aqueous environment free of alcohol, such as ethanol, the release rate of drug substance delivered from the immediate release composition is decreased when the immediate release composition is administered substantially simultaneously with the ingestion of alcohol or within a period of up to 60 minutes before and up to 60 minutes after ingesting alcohol.

In other embodiments, the immediate release compositions described herein are resistant to dose dumping in the presence of alcohol when said alcohol is ingested either:
a. together with the immediate release composition; or
b. within a period of up to 60 minutes before and up to 60 minutes after ingesting the composition.

In such embodiments, when compared to the release rate achieved in an aqueous environment free of alcohol, such as ethanol, the release rate of drug substance delivered from the immediate release composition is decreased when the immediate release composition is administered substantially simultaneously with the ingestion of alcohol or within a period of up to 60 minutes before and up to 60 minutes after ingesting alcohol.

In another embodiment, the immediate release compositions described herein include a polyethylene glycol having a molecular weight of from about 900 to about 17,000 Daltons, one or more effervescent agents, one or more drug substances selected from anaesthetics, analgesics, opioids, antipyretics, antimigraine agents, antiepileptics, anti-parkinson agents, dopaminergic agents, antipsychotics, anxiolytics, sedatives, antidepressants, psychostimulating agents used for ADHD and nootropics, and agents used in addictive disorders. In such an embodiment, the immediate release composition may optionally include one or more disintegrants.

The compositions described herein are suitable for use in various methods. For example, in particular embodiments, immediate release compositions as described herein may be used:
i) to prevent abuse of said drug substance, when the composition is ingested with alcohol;
ii) to prevent dose dumping of said drug substance, when the composition is ingested with alcohol; and/or
iii) to treat a patient suffering from a disease, disorder or condition to which the drug substance is therapeutically effective, wherein the patient ingests 3 or more alcoholic beverages daily. In such embodiments, the patient to be treated may an alcoholic beverage or pharmaceutical composition containing alcohol either:
a. together with the composition, or
b. within a period of up to 60 minutes before and up to 60 minutes after ingesting the composition.

Immediate release compositions suitable for use in the methods described herein include compositions that comprise a drug substance, a polyglycol having a molecular weight of from about 900 to about 17,000 Daltons, one or more effervescent agents, and, optionally, one or more disintegrants.

Methods for preparing immediate release compositions resistant to abuse by intake of alcohol or by crushing are also provided herein. For example, in specific embodiments, methods of manufacturing an immediate release composition according to the present description include:
i) mixing a drug substance and a polyglycol having a molecular weight of from about 900 to about 17,000 Daltons with one or more effervescent agents and, optionally, one or more disintegrants; and
ii) feeding an injection moulding machine, an extruder or a tablet compression machine with the mixture obtained in step i).

As is detailed herein, immediate release compositions according to the present description can be formulated such that drug substance contained therein is released from the composition in the stomach of a patient with a release profile that is dependent on the concentration of ethanol. In particular, immediate release compositions according to the present description can be formulated such that the release rate of drug substance from the composition decreases as the concentration of ethanol in the dissolution environment (e.g., the stomach or gastrointestinal tract of a patient) increases.

Polymers

Polymers suitable for use in the compositions described herein include polyglycols. The polyglycols used in immediate release compositions according to the present description are typically in the form of a homopolymer. In specific embodiments the immediate release compositions described herein are formulated using at least one polyglycol polymer that is substantially water-soluble, thermoplastic, crystalline, semi-crystalline or amorphous. Of course, mixtures of substantially water-soluble, crystalline, semi-crystalline or amorphous polyglycol polymers may also be used in formulating the immediate release compositions described herein. Specific examples of polymers suitable for use in the immediate release compositions described herein are polyethylene glycols, including derivatives such as mono- and dimethoxy-polyethylene glycols (mPEGs), and polyethylene oxides. The immediate release compositions described herein may be prepared as matrix compositions formed using the polyglycol polymers described herein.

In specific embodiments, the one or more polymers included in the immediate release compositions described herein are present at a concentration of from about 5% w/w to about 99.9% w/w. For example, in one embodiment, the immediate release composition may include one or more polymers as described herein in at a concentration selected from about 10% w/w to about 95% w/w, about 15% w/w to about 90% w/w, about 20% w/w to 85% w/w, and about 30% w/w to about 85% w/w, calculated as w/w % of the composition. Specific examples of polyglycol polymers are described herein. In addition, polymers other than polyglycol polymers may be used in immediate release compositions according to the present description, and examples of such non-polyglycol polymers are also described.

Polyethylene glycols (PEGs) are linear polydisperse polymers composed of repeating units of ethylene glycol. Their chemical formula is $HOCH_2[CH_2OCH_2]_mCH_2OH$ where m represents the average number of repeating units. Alternatively, the general formula $H[OCH_2CH_2]_nOH$ may be used to represent polyethylene glycol, where n is a number m in the previous formula+1. See the structural presentations of polyethylene glycol below. n is the average number of oxyethylene groups. n equals m+1.

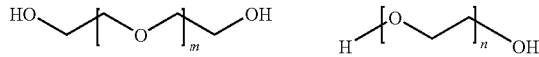

Polyethylene oxides (PEOs) are linear polydisperse nonionic polymers composed of repeating units of ethylene oxide. Their chemical formula is $HO[CH_2CH_2O]_nH$ where n represents the average number of oxyethylene groups. See the structural presentation of polyethylene oxide below. n is the average number of oxyethylene groups.

Depending on the preparation method, high molecular weight PEO may have one terminal methyl group.

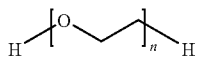

Polyethylene glycols are mixtures of addition of ethylene glycol. In general PEG refers to polymers chains with molecular weights below 20,000, while PEO refers to higher molecular weights polymers. However, because of the similarities between PEO and PEG, the terms are often used interchangeably for the same compound.

Polyethylene glycols and/or polyethylene oxides, which are suitable for use in the immediate release compositions described herein, include those having molecular weights of from about 900 Daltons, to about 17,000 Daltons. Commercially available PEG/PEO's relevant for the present invention may have an average molecular weight selected from the following: 1000, 1100, 1900, 2000, 2800, 2900, 3350, 4400, 5800, 6000, 8000, 8400, 10,000, 12,000, 14,600 or 17,000 Daltons. The immediate release compositions that utilize one or more polyethylene glycols and/or polyethylene oxides as described herein may be formulated and manufactured as matrix compositions.

In specific embodiments, an immediate release composition according to the present description thus comprises one or more polyglycols having a molecular weight selected from 1000, 1100, 1900, 2000, 2800, 2900, 3350, 4400, 5800, 6000, 8000, 8400, 10,000, 12,000, 14,600 or 17,000 Daltons. In one such embodiment, the immediate release composition includes one or more polyglycols having a molecular weight selected from PEG 3,350 S, PEG 6,000, PEG 10,000, PEG 14,000 and PEG 17,000.

In particular embodiments, it has been found that, in order to achieve immediate release of the drug substance, it is beneficial to select PEG's/PEO's having a molecular weight of from about 900 to about 17,000 Daltons when formulating immediate release compositions. Where desired, mixtures of PEO and/or mixtures of PEG materials with different average molecular weights can be used in order to obtain a desired average molecular weight for the polyglycol material utilized in immediate release compositions described herein.

Polymer materials used in immediate release compositions according to the present description, such as, for example, polyglycol, PEG and PEO materials, should exhibit a melting point higher than the body temperature of the patient, such as a human patient, to whom the composition is to be administered. Thus, the polymer material employed in the immediate release compositions described herein composition will typically have a melting point of about 30° C. to about 120° C. such as, for example, from about 35° C. to about 100° C. or from about 40° C. to about 80° C.

In addition to a polymer of a polyglycol type as described above, other polymers may be suitable for use in the immediate release compositions described herein, provided that the solubility of the composition and/or release rate of the drug substance from the composition in an aqueous media that is free of ethanol water is higher than the solubility of the composition and/or release rate of the drug substance from the composition in a dissolution medium containing 40% v/v ethanol, as tested in the in vitro dissolution test described herein. In specific embodiments, the solubility of the immediate release composition in an aqueous media that is free of ethanol and/or the release rate in an aqueous media that is free of ethanol of the drug substance from the immediate release composition including one or more polymers other than a polyglycol type polymer is selected from at least 1.5 times higher, at least 2 times higher, at least 5 times higher, at least 10 times higher, at least 25 times higher, at least 50 times higher or at least 100 times higher than the dissolution and/or release rate exhibited in a dissolution medium containing 40% v/v ethanol, as tested in the in vitro dissolution test described herein. Polymers other than polyglycol polymers that may be suited for use in the immediate release compositions described herein, either as a substitute for one or more polyglycol polymers or in addition to one or more polyglycol polymers, may be selected from, for example: modified or unmodified water soluble natural polymers, such as glucomannan, galactan, glucan, polygalacturonic acid, polyxylane, polygalactomannans, rhanogalacturonan, polyxyloglycan, arabinogalactan, and starch, cellulose, chitosan, alginate, fibrin, collagen, gelatin, hyaluronic acid, amylopectin, pectin including low methylated or methoxylated pectins, dextran and fatty acids and alcohols; synthetic polymers such as polyvinylpyrrolidone (PVP), PVA, PVB, Eudragit L methyl ester, Eudragit L, Eudragit RL, Eudragit E, Eudragit S, PHPV, PHA, PCL, PLGA and PLA; and hydrogels made from the polymers or combinations of the polymers mentioned above and/or from polymers derived from HEMA, HEEMA, MEMA, MEEMA, EDGMA, NVP, VAc, AA, acrylamide, MAA, HPMA, PEGA, PEGMA, PEGDMA, PEGDA, and PEGDMA.

Disintegrants and Effervescent Agents

The immediate release compositions described herein include one or more effervescent agents and may optionally include one or more disintegrants. In some embodiments, the disintegrant and/or the effervescent agent are swellable in water or are soluble to very soluble in water and inswellable or insoluble in a dissolution medium containing 40% v/v of ethanol. Accordingly, in particular embodiments of the immediate release compositions described herein, wherein the composition includes one or more disintegrants, such disintegrants are selected such that the disintegrants exert their disintegration properties (e.g., swelling) in water or aqueous solutions free of alcohol, such as ethanol, while also exhibiting a loss or marked reduction of their disintegration performance in aqueous solutions containing 40% v/v ethanol. Moreover, in particular embodiments, the effervescent agent and, where included, the disintegrant utilized in the immediate release composition are selected such that they are only sparingly soluble, as defined herein, in aqueous solutions containing 40% v/v ethanol, as measured in the in vitro dissolution test described herein.

For purposes of the present disclosure, the following definitions for varying degrees of solubility will be used: "very soluble" refers solute materials wherein less than 1 part solvent is required to dissolve 1 part solute; "freely soluble" refers to solute materials wherein about 1 to about 10 parts solvent are required to dissolve 1 part solute; "soluble" refers to solute materials wherein about 10 to about 30 parts solvent are required to dissolve 1 part solute; "sparingly soluble" refers to solute materials wherein about 30 to about 100 parts solvent are required to dissolve 1 part solute; "slightly soluble" refers to solute materials wherein about 100 to about 1,000 parts solvent are required to dissolve 1 part solute; "very slightly soluble" refers to solute materials wherein about 1,000 to about 10,000 parts solvent are required to dissolve 1 part solute; and "insoluble" refers to solute materials wherein more than 10,000 parts solvent are required to dissolve 1 part solute.

It has been found that immediate release compositions according to the present description exhibit a significantly slower drug substance release rate when introduced in dissolution environments including alcohol. Specific embodiments exhibiting such behavior include compositions formulated with one or more polyglycol polymers, such as one or more PEG and/or PEO polymers as described herein, and one or more effervescent agents. In one such embodiment, the immediate release composition is formulated using one or more PEG polymers, one or more effervescent agent, and one or more disintegrating agent, with each of the polymer material, effervescent agent, and disintegrating agent selected from the materials described herein. The delay in release rate of the drug substances was not observed in compositions that included a disintegrant alone. This behavior may have an in vivo effect, so that potential abusers would not achieve an enhancing effect when taking the tablet in combination with alcohol.

In specific embodiments, the immediate release composition described herein, when introduced into a dissolution environment including alcohol, exhibits a slower release of drug substance selected from at least about 20 minutes, at least 30 minutes, as at least about 40 minutes, at least about 50 minutes, and at least about 60 minutes. In one such embodiment, the immediate release composition described herein is formulated such that, when introduced into a dissolution environment including 40% v/v alcohol, such as an aqueous solution including 40% v/v ethanol, the composition exhibits a slower release of the drug substance selected from at least about 20 minutes, at least about 30 minutes, at least about 40 minutes, at least about 50 minutes, and at least about 60 minutes. Alcohol generally enhances penetration of the epithelia by drug substances, but the slower release provided by immediate release compositions described herein may offset the increase in permeability normally associated by the presence of alcohol such that the desired in vivo effect of the immediate release composition is substantially maintained (e.g., absorption rate of the drug from the immediate release composition is substantially maintained), even in the presence of alcohol.

In specific embodiments, the effervescent agent included in an immediate release composition as described herein is at least one component of an effervescent couple that includes an acid and a base. Such an effervescent couple is activated when contacted with water. In examples of effervescent couples suited to use in the immediate release compositions described herein, water liberates the acid and base, enabling the acid and base to react with each other to produce carbon dioxide gas. Examples of acids that may be used to form an effervescent couple include water soluble organic acids. Further specific examples include citric acid, ascorbic acid, glutaric acid, malic acid, malonic acid, adipic acid, clavulanic acid, oxalic acid, tartaric acid, fumaric acid, succinic acid, sodium acid pyrophosphate, sorbic acid, sodium citrate dehydrate, lactic acid, hexamic acid, benzoic acid, etianic acids, disphosphonoic acids and acidic salts and acid anhydrides thereof, and mixtures thereof. Examples of useful acid anhydrides include citraconic anhydride, glucono-D-lactone, sulphuric acid, hyaluronic acid and succinic anhydride. Examples of useful acid salts include potassium bitartrate, acid citrate salts, sodium dihydrogen phosphate, disodium dihydrogen phosphate, and combinations thereof. In particular embodiments, the immediate release composition described herein may be formulated with an acid present in the composition in an amount selected from about 1% by weight to about 60% by weight and from about 2% by weight to about 30% by weight.

The base of an effervescent couple utilized in an immediate release composition as described herein, may be selected based on its capability to generate carbon dioxide. Examples of bases that may be used in formulated an effervescent couple included in an immediate release composition as described herein include, for example, water soluble carbonates and bicarbonates. Further specific examples of suitable bases include sodium bicarbonate such as "Effer-Soda", sodium carbonate, sodium sesqui-carbonate, potassium carbonate, potassium bicarbonate, ammonium bicarbonate, calcium carbonate, magnesium carbonate, sodium glycine carbonate, L-lysine carbonate, arginine carbonate, zinc carbonate, and mixtures thereof. In particular embodiments, the immediate release composition described herein may be formulated with a base present in the composition in an amount selected from about 1% by weight to about 60% by weight and from about 2% by weight to about 50% by weight.

In particular embodiments, the immediate release composition described herein includes an effervescent couple selected from citric acid+$NaHCO_3$, Tartaric acid+$NaHCO_3$, Succinic acid+$NaHCO_3$, Malonic acid+$NaHCO_3$, Benzoic acid+$NaHCO_3$, Oxalic acid+$NaHCO_3$, Malic acid+$NaHCO_3$ and Glutaric acid+$NaHCO_3$ As detailed herein, the immediate release composition may optionally include a disintegrant. Examples of disintegrants suitable for use in the compositions described here include Sodium starch glycolate, Povidone, Sodium alginate, Alginic acid, Calcium alginate, Carboxymethylcellulose calcium, Carboxymethylcellulose sodium, Powdered cellulose, Chitosan, Croscarmellose sodium (Croscarmellose Na), Crospovidone, Cross-linked polyvinylpyrrolidone, Hydroxypropyl starch, Hydroxypropyl cellulose low-substituted, Magnesium aluminium silicate, Methylcellulose, Microcrystalline cellulose, pregelatinized starch, Docusae sodium, Guar gum, Polacrilin potassium. In one embodiment, the immediate release composition is formulated with Croscarmellose sodium as a disintegrant. Where included, a disintegrant may be included in an immediate release composition in an amount selected from about 1% by weight to about 60% by weight and from about 5% by weight to about 50% by weight.

In some embodiments, the immediate release composition described herein includes both a disintegrant and an effervescent agent. Where the immediate release composition includes both a disintegrant and an effervescent agent, the concentration of the one or more disintegrants, and/or effervescent agent may be selected from about 1% w/w to about 80% w/w, about 5% w/w to about 70% w/w, and about 10% w/w to about 60% w/w.

One or more pharmaceutically acceptable excipients or additives may also be present (see the section "Pharmaceutically acceptable excipients").

Pharmaceutically Acceptable Excipients

The compositions described herein may additionally include one or more pharmaceutically acceptable excipients in addition to the constituents already described. For example, one or more excipients may be included to improve the technical properties of the composition so that it is be easier to manufacture or in order to improve the properties of the composition, such as, for example release rate of the drug substance, stability of the drug substance, stability of the immediate release composition itself, etc.

Suitable pharmaceutically acceptable excipients for use in a composition of the invention may be selected from, for example, fillers, diluents, disintegrants, glidants, pH-adjusting agents, viscosity adjusting agents, solubility increasing or decreasing agents, osmotically active agents and solvents. Where utilized in the immediate release compositions described herein, glidants/lubricants may be included at a concentration of from 0% w/w to about 5% w/w, binders may be included at a concentration of from 0% w/w to about 25% w/w, solubility increasing agents may be included at a concentration of from 0% w/w to about 15% w/w, stabilizers may be included at a concentration of 0% w/w to 15% w/w, and modifiers may be included at a concentration of 0% w/w to about 15% w/w.

Excipients suitable for use in the immediate release compositions according to the present description include conventional tablet or capsule excipients. These excipients may be, for example, diluents such as dicalcium phosphate, calcium sulphate, lactose or sucrose or other disaccharides, cellulose, cellulose derivatives, kaolin, mannitol, dry starch, glucose or other monosaccharides, dextrin or other polysaccharides, sorbitol, inositol or mixtures thereof; binders such as alginic acid, calcium alginate, sodium alginate, starch, gelatin, saccharides (including glucose, sucrose, dextrose and lactose), molasses, panwar gum, ghatti gum, mucilage of isapol husk, carboxy-methyl-cellulose, methylcellulose, veegum, larch arabolactan, polyethylene glycols, ethylcellulose, water, alcohols, waxes, polyvinylpyrrolidone such as, e.g., PVP K90 or mixtures thereof; lubricants such as talc, silicium dioxide, magnesium stearate, calcium stearate, stearic acid, hydrogenated vegetable oils, sodium benzoate, sodium chloride, leucine, carbowax 4000, magnesium lauryl sulphate, sodium laurylsulphate, stearyl alcohol, Polysorbate 20, Polysorbate 60, Polysorbate 80, Macrogol stearate, Macrogol lauryl ether, stearoyl macrogolglycerides, sorbitan stearate, sorbitan laurate, Macrogol glycerol hydroxystearat, colloidal silicon dioxide and mixtures thereof, disintegrants such as starches, clays, cellulose derivatives including microcrystalline cellulose, methylcellulose, carboxymethycellulose calcium, carboxymethylcellulose sodium, cellulose, cross-carmellose sodium, gums, aligns, various combinations of hydrogen-carbonates with weak acids (e.g. sodium hydrogencarbonate/tartaric acid or citric acid) crosprovidone, sodium starch glycolate, agar, alginic acid, calcium alginate, sodium alginate, chitosan, colloidal silicon dioxide, docusate sodium, guar gum, low-substituted hydroxypropyl cellulose, hydroxypropyl starch, magnesium aluminium silicate, polacrilin potassium, povidone, sodium starch glycolate, pregelatinized starch, cation exchange resins, citrus pulp, veegum, glycollate, natural sponge, bentonite, sucralfate, calcium hydroxyl-apatite or mixtures thereof, effervescent agents (carbonate release) such as citric acid, anhydrous, citric acid, monohydrate, dextrates, fumaric acid, potassium bicarbonate, sodium bicarbonate, sodium citrate, dehydrate, tartaric acid or mixtures thereof.

Furthermore, in some embodiments, the immediate release compositions described herein may comprise one or more agents selected from the group consisting of sweetening agents, flavouring agents and colouring agents, in order to provide an aesthetic and palatable preparation. Examples of such agents include maltol, citric acid, water soluble FD&C dyes and mixtures thereof, and direct compression sugars such as Di-Pac from Amstar. In addition, coloured dye migration inhibitors such as tragacanth, acacia or attapulgite talc may be added. Specific examples include Calcium carbonate, 1,3,5-trihydroxybenzene, chromium-cobalt-aluminium oxide, ferric ferrocyanide, ferric oxide, Iron ammonium citrate, iron (III) oxide hydrated, iron oxides, carmine red, magnesium carbonate and titanium dioxide.

In other embodiments, immediate release compositions according to the present description may further include one or more plasticizers. Plasticizer suitable for use in the compositions described herein may be selected from, for example, mono- and di-acetylated monoglycerides, diacetylated monoglycerides, acetylated hydrogenated cottonseed glyceride, glycerol cocoate, Polyethylene glycols or polyethylene oxides (e.g. with a molecular weight of about 1,000-500,000 Daltons), dipropylene glycol salicylate glycerin, fatty acids and esters, phthalate esters, phosphate esters, amides, diocyl phthalate, phthalyl glycolate, mineral oils, hydrogenated vegetable oils, vegetable oils, acetylated hydrogenated soybean oil glycerides, Castor oil, acetyl tributyl citrate, acetyl triethyl citrate, methyl abietate, nitrobenzene, carbon disulfide, β-naphtyl salicylate, sorbitol, sorbitol glycerol tricitrate, fatty alcohols, cetostearyl alcohol, cetyl alcohol, stearyl alcohol, oleyl alcohol, myristyl alcohol, sucrose octaacetate, alfa-tocopheryl polyethylene glycol succinate (TPGS), tocopheryl derivative, diacetylated monoglycerides, diethylene glycol monostearate, ethylene glycol monostearate, glycerol monooleate, glycerol monostearate, propylene glycol monostearate, macrogol esters, macrogol stearate 400, macrogol stearate 2000, polyoxyethylene 50 stearate, macrogol ethers, cetomacrogol 1000, lauromacrogols, nonoxinols, octocinols, tyloxapol, poloxamers, polyvinyl alcohols, polysorbate 20, polysorbate 40, polysorbate 60, polysorbate 65, polysorbate 80, polysorbate 85, sorbitan monolaurate, sorbitan monooleate, sorbitan monopalmitate, sorbitan monostearate, sorbitan sesquioleate, sorbitan trioleate, sorbitan tristearate and sucrose esters, amyl oleate, butyl oleate, butyl stearate, diethylene glycol monolaurate, glycerol tributyrate, Cumar W-1, Cumar MH-1, Cumar V-1, Flexol B-400, monomeric polyethylene ester, Piccolastic A-5, Piccalastic A-25, Beckolin, Clorafin 40, acetyl tributyl citrate, acetyl triethyl citrate, benzyl benzoate, butoxyethyl stearate, butyl and glycol esters of fatty acids, butyl diglycol carbonate, butyl ricinoleate, butyl phthalyl butyl glycolate, camphor, dibutyl sebacate, dibutyl tartrate, diphenyl oxide, glycerine, HB-40, hydrogenated methyl ester of rosin, methoxyethyl oleate, monoamylphthalate, Nevillac 10, Paracril 26, technical hydroabietyl alcohol, triethylene glycol dipelargonate, solid aliphatic alcohols, nitrobenzene, carbon disulfide, β-naphtyl salicylate, phthalyl glycolate, dioctyl phthalate, and mixtures thereof.

In other embodiments, immediate release compositions according to the present description may further include one or more stabilizers. Stabilizers (chemical) suitable for use in the compositions described herein may be selected from, for example, TPG, such as in the form of TPGS due to surfactant properties, BHA, BHT, t-butyl hydroquinone, calcium ascorbate, gallic acid, hydroquinone, maltol, octyl gallate, sodium bisulfite, sodium metabisulfite, tocopherol and derivates thereof, citric acid, tartaric acid, and ascorbic acid. Other suitable stabilisers include, for example, trivalent phosphorous, such as phosphite, phenolic antioxidants, hydroxylamines, lactones such as substituted benzofuranones, hindered phenols, thiosynergists and/or hindered amines, acids (ascorbic acid, erythorbic acid, etidronic acid, hypophosphorous acid, nordihydroguaiaretic acid, propionic acid etc.), phenols, dodecyl gallate, octyl gallate, 1,3,5-trihydroxybenzene, organic and inorganic salts (calcium ascorbate, sodium ascorbate, sodium bisulphite, sodium metabisulfite, sodium sulfite, potassium bisulphite, potassium metabisulphite), esters (calcium ascorbate, dilauryl thiodipropionate, dimyristyl thiodipropionate, distearyl thiodipropionate), pyranon (maltol), and vitamin E (tocopherol, D-α-tocopherol, DL-α-tocopherol, tocopheryl acetate, d-α-tocopheryl acetate, dl-α-tocopheryl acetate. In addition, other anti-oxidative agents known in the art may be included in the compositions according to the present description. Other stabilizers suitable for use in the compositions described herein may be selected from sorbitol glycerol tricitrat and sucrose octaacetate.

Compositions according to the present description may additionally include a release modifier. A suitable release modifier may be selected from, for example, fatty acids and esters, fatty alcohols, cetyl alcohol, stearyl alcohol, mineral oils, hydrogenated vegetable oils, vegetable oils, acetylated hydrogenated soybean oil glycerides, Castor oil, phosphate esters, amides, phthalate esters, glycerol cocoate, oleyl alcohol, myristyl alcohol, sucrose octaacetate, diacetylated monoglycerides, diethylene glycol monostearate, ethylene glycol monostearate, glycerol monooleate, glycerol monostearate, propylene glycol monostearate, macrogol esters, macrogol stearate 400, macrogol stearate 2000, polyoxyethylene 50 stearate, macrogol ethers, cetomacrogol 1000, lauromacrogols, poloxamers, polyvinyl alcohols, sorbitan monolaurate, sorbitan monooleate, sorbitan monopalmitate, sorbitan monostearate, sorbitan sesquioleate, sorbitan trioleate, sorbitan tristearate, ethylcellulose, cellulose acetate, cellulose propionate, cellulose nitrate, cellulose derivative selected from the group consisting of methylcellulose, carboxymethylcellulose and salts thereof, cellulose acetate phthalate, microcrystalline cellulose, ethylhydroxyethylcellulose, ethylmethyl-cellulose, hydroxyethylcellulose, hydroxyethylmethylcellulose, hydroxypropylcellulose, hydroxypropylmethylcellulose, hydroxymethylcellulose and hydroxymethylpropyl-cellulose, cellulose acetate, polylactic acid or polyglycolic acid and copolymers thereof, methacrylates, a co-polymer of methacrylate-galactomannan, polyvinyl alcohols, glycerinated gelatin, cocoa butter. Other suitable release modifiers may be selected from, for example, inorganic acids, inorganic bases, inorganic salts, organic acids or bases and pharmaceutically acceptable salts thereof, saccharides, oligosaccharides, polysaccharides, polyethylene glycol derivatives and cellulose and cellulose derivatives.

Alternatively or additionally, the compositions described here may include a pharmaceutically acceptable excipient selected from mono-, di-, oligo, polycarboxylic acid and one or more amino acids, such as, for example, acetic acid, succinic acid, citric acid, tartaric acid, acrylic acid, benzoic acid, malic acid, maleic acid, sorbic acid etc., aspartic acid, glutamic acid, etc.

The compositions described herein may further include an organic acid as an excipient. Examples of suitable organic acids that may be further included in the compositions described herein include acetic acid/ethanoic acid, adipic acid, angelic acid, ascorbic acid/vitamin C, carbamic acid, cinnamic acid, citramalic acid, formic acid, fumaric acid, gallic acid, gentisic acid, glutaconic acid, glutaric acid, glyceric acid, glycolic acid, glyoxylic acid, lactic acid, levulinic acid, malonic acid, mandelic acid, oxalic acid, oxamic acid, pimelic acid, and pyruvic acid.

The compositions described herein may further include an inorganic acid as an excipient. Examples of suitable inorganic acids that may be further included in the compositions described herein include pyrophosphoric, glycerophosphoric, phosphoric such as ortho- and meta phosphoric acid, boric acid, hydrochloric acid, and sulfuric acid.

The compositions described herein may further include an organic compound, such as aliminum as an excipient.

The compositions described herein may further include an organic base as an excipient. Examples of organic bases are p-nitrophenol, succinimide, benzenesulfonamide, 2-hydroxy-2cyclohexenone, imidazole, pyrrole, diethanolamine, ethyleneamine, tris (hydroxymethyl) aminomethane, hydroxylamine and derivates of amines, sodium citrate, aniline, hydrazine.

The compositions described herein may further include an inorganic base as an excipient. Examples of inorganic bases include, for example, an aluminium oxide such as, for example, aluminium oxide trihydrate, alumina, sodium hydroxide, potassium hydroxide, calcium carbonate, ammonium carbonate, ammonium hydroxide, and the like.

The compositions described herein may further include a pharmaceutically acceptable salt of an organic acid as an excipient. Suitable pharmaceutically acceptable salts of an organic acid include, for example, an alkali metal salt or an alkaline earth metal salt such as, for example, sodium phosphate, sodium dihydrogenphosphate, disodium hydrogenphosphate, potassium phosphate, potassium dihydrogenphosphate, potassium hydrogenphosphate, calcium phosphate, dicalcium phosphate, sodium sulphate, potassium sulphate, calcium sulphate, sodium carbonate, sodium hydrogencarbonate, potassium carbonate, potassium hydrogencarbonate, calcium carbonate, magnesium carbonate, sodium acetate, potassium acetate, calcium acetate, sodium succinate, potassium succinate, calcium succinate, sodium citrate, potassium citrate, calcium citrate, sodium tartrate, potassium tartrate, calcium tartrate, etc.

The compositions described herein may further include a pharmaceutically acceptable inorganic salt as an excipient. Examples of suitable inorganic salts for use in a matrix composition according to the present description include sodium chloride, potassium chloride, calcium chloride, magnesium chloride, etc.

The compositions described herein may further include a pharmaceutically acceptable saccharide as an excipient. Suitable saccharides include, for example, glucose, ribose, arabinose, xylose, lyxose, xylol, allose, altrose, inosito, glucose, sorbitol, mannose, gulose, Glycerol, idose, galactose, talose, maltose, mannitol, erythritol, ribitol, xylitol, maltitol, isomalt, lactitol, sucrose, fructose, lactose, dextrin, dextran, amylose, and xylan.

The compositions described herein may further include a pharmaceutically acceptable cellulose or cellulose derivative as an excipient. Examples of such materials include, cellulose and cellulose derivatives selected from methylcellulose, carboxymethylcellulose and salts thereof, microcrystalline cellulose, ethylhydroxyethylcellulose, ethylcellulose, cellulose acetate, cellulose proprionate, cellulose nitrate, cellulose acetate phthalate, ethylmethylcellulose, hydroxy-ethylcellulose, hydroxyethylmethylcellulose, hydroxypropylcellulose, hydroxypropyl-methylcellulose, hydroxymethylcellulose, and hydroxymethylpropylcellulose.

Drug Substances for use in a Composition of the Invention

The immediate release compositions described herein include one or more drug substances. The amount of substance is determined by the therapeutic index of the indication for which the drug substance is intended. Typically, the amount of the drug substance corresponds to a daily or part of a daily therapeutic dose. The immediate release compositions described herein are suitable for use with both water soluble drug substances as well as drug substances that are slightly soluble or insoluble in water. Thus, a composition according to the present description may comprise one or more drug substances. As used herein, the term "drug substance" is used broadly, and refers to materials that are biologically active such that they are useful for therapeutic or prophylactic treatment of one or more diseases, disorders or conditions. Additionally, the term "drug substance" includes materials that may be used in diagnostic applications. The term "drug substance" also includes any compound, or mixture thereof, that can be delivered from the immediate release compositions described herein to produce a beneficial result, such as, for example, but not limited to, an anti-inflammatory effect, an antirheumatic effect, an analgesic effect, an antimigraine effect, an antiepileptic effect, an anticholinergic effect, a dopaminergic effect, an antipsychotic effect, an anxiolytic effect, a hypnotic and/or sedative effect or an antidepressant effect, depending on the specific drug substance comprised by the composition.

Examples of specific drug substances suitable for use in a composition of the invention are:

Antiinflammatory and antirheumatic drug substances, such as, for example, Butylpyrazolidines, Phenylbutazone, Mofebutazone, Oxyphenbutazone, Clofezone, Kebuzone, Acetic acid derivatives and related substances, Indometacin, Sulindac, Tolmetin, Zomepirac, Diclofenac, Alclofenac, Bumadizone, Etodolac, Lonazolac, Fentiazac, Acemetacin, Difenpiramide, Oxametacin, Proglumetacin, Ketorolac, Aceclofenac, Bufexamac, Oxicams, Piroxicam, Tenoxicam, Droxicam, Lornoxicam, Meloxicam, Propionic acid derivatives, Ibuprofen, Naproxen, Ketoprofen, Fenoprofen, Fenbufen, Benoxaprofen, Suprofen, Pirprofen, Flurbiprofen, Indoprofen, Tiaprofenic acid, Oxaprozin, Ibuproxam, Dexibuprofen, Flunoxaprofen, Alminoprofen, Dexketoprofen, Fenamates, Mefenamic acid, Tolfenamic acid, Flufenamic acid, Meclofenamic acid, Coxibs, Celecoxib, Rofecoxib, Valdecoxib, Parecoxib, Etoricoxib, Lumiracoxib, Nabumetone, Niflumic acid, Azapropazone, Glucosamine, Benzydamine, Glucosaminoglycan polysulphate, Proquazone, Orgotein, Nimesulide, Feprazone, Diacerein, Morniflumate, Tenidap, Oxaceprol, Chondroitin sulphate, Feprazone, Dipyrocetyl, Acetylsalicylic acid, Quinolines, Oxycinchophen, Gold preparations, Sodium aurothiomalate, Sodium aurotiosulphate, Auranofin, Aurothioglucose, Aurotioprol, Penicillamine and similar agents, and Bucillamine;

Analgesics such as, for example, Opioids, Natural opium alkaloids, semi-synthetic opium alkaloids, Morphine, Opium, Hydromorphone, Nicomorphine, Oxycodone, Dihydrocodeine, Diamorphine, Papaveretum, Codeine, Phenylpiperidine derivatives, Ketobemidone, Pethidine, Fentanyl, Diphenylpropylamine derivatives, Dextromoramide, Piritramide, Dextropropoxyphene, Bezitramide, Methadone, Benzomorphan derivatives, Pentazocine, Phenazocine, Oripavine derivatives, Buprenorphine, Morphinan derivatives, Butorphanol, Nalbuphine, Tilidine, Tramadol, Dezocine, Salicylic acid and derivatives, Acetylsalicylic acid, Aloxiprin, Choline salicylate, Sodium salicylate, Salicylamide, Salsalate, Ethenzamide, Morpholine salicylate, Dipyrocetyl, Benorilate, Diflunisal, Potassium salicylate, Guacetisal, Carbasalate calcium, Imidazole salicylate, Pyrazolones, Phenazone, Metamizole sodium, Aminophenazone, Propyphenazone, Nifenazone, Anilides, Paracetamol, Phenacetin, Bucetin, Propacetamol, Rimazolium, Glafenine, Floctafenine, Viminol, Nefopam, Flupirtine, and Ziconotide;

Anesthetics such as, for example, Ethers, Diethyl ether, Vinyl ether, Halogenated hydrocarbons, Halothane, Chloroform, Methoxyflurane, Enflurane, Trichloroethylene, Isoflurane, Desflurane, Sevoflurane, Barbiturates, Methohexital, Hexobarbital, Thiopental, Narcobarbital, Opioid anesthetics, Fentanyl, Alfentanil, Sufentanil, Phenoperidine, Anileridine, Remifentanil, Other general anesthetics, Droperidol, Ketamine, Propanidid, Alfaxalone, Etomidate, Propofol, Hydroxybutyric acid, Nitrous oxide, Esketamine, Xenon, Esters of aminobenzoic acid, Metabutethamine, Procaine, Tetracaine, Chloroprocaine, Benzocaine, Amides, Bupivacaine, Lidocaine, Mepivacaine, Prilocaine, Butanilicaine, Cinchocaine, Etidocaine, Articaine, Ropivacaine, Levobupivacaine, Esters of benzoic acid, Cocaine, Ethyl chloride, Dyclonine, Phenol, and Capsaicin;

Antimigraine drug substances such as, for example, Ergot alkaloids, Dihydroergotamine, Ergotamine, Methysergide, Lisuride, Corticosteroid derivatives, Flumedroxone, Selective serotonin (5HT1) agonists, Sumatriptan, Naratriptan, Zolmitriptan, Rizatriptan, Almotriptan, Eletriptan, Frovatriptan, Other antimigraine preparations, Pizotifen, Clonidine, Iprazochrome, Dimetotiazine, and Oxetorone;

Antiepileptic drug substancessuch as, for example, Barbiturates and derivatives, Methylphenobarbital, Phenobarbital, Primidone, Barbexaclone, Metharbital, Hydantoin derivatives, Ethotoin, Phenytoin, Amino(diphenylhydantoin) valeric acid, Mephenytoin, Fosphenytoin, Oxazolidine derivatives, Paramethadione, Trimethadione, Ethadione, Succinimide derivatives, Ethosuximide, Phensuximide, Mesuximide, Benzodiazepine derivatives, Clonazepam, Carboxamide derivatives, Carbamazepine, Oxcarbazepine, Rufinamide, Fatty acid derivatives, Valproic acid, Valpromide, Aminobutyric acid, Vigabatrin, Progabide, Tiagabine, Other antiepileptics, Sultiame, Phenacemide, Lamotrigine, Felbamate, Topiramate, Gabapentin, Pheneturide, Levetiracetam, Zonisamide, Pregabalin, Stiripentol, Lacosamide, and Beclamide;

Anticholinergic drug substances such as, for example, Tertiary amines, Trihexyphenidyl, Biperiden, Metixene, Procyclidine, Profenamine, Dexetimide, Phenglutarimide, Mazaticol, Bornaprine, Tropatepine, Ethers chemically close to antihistamines, Etanautine, Orphenadrine (chloride), Ethers of tropine or tropine derivatives, Benzatropine, Etybenzatropine;

Dopaminergic drug substances such as, for example, Dopa and dopa derivatives, Levodopa, Melevodopa, Etilevodopa, Adamantane derivatives, Amantadine, Dopamine agonists, Bromocriptine, Pergolide, Dihydroergocryptine mesylate, Ropinirole, Pramipexole, Cabergoline, Apomorphine, Piribedil, Rotigotine, Monoamine, oxidase B inhibitors, Selegiline, Rasagiline, other dopaminergic agents, Tolcapone, Entacapone, and Budipine;

Antipsychotic drug substances such as, for example, Phenothiazines with an aliphatic side-chain, Chlorpromazine, Levomepromazine, Promazine, Acepromazine, Triflupromazine, Cyamemazine, Chlorproethazine, Phenothiazines with piperazine structure, Dixyrazine, Fluphenazine, Perphenazine, Prochlorperazine, Thiopropazate, Trifluoperazine, Acetophenazine, Thioproperazine, Butaperazine, Perazine, Phenothiazines with piperidine structure, Periciazine, Thioridazine, Mesoridazine, Pipotiazine, Butyrophenone derivatives, Haloperidol, Trifluperidol, Melperone, Moperone, Pipamperone, Bromperidol, Benperidol, Droperidol, Fluanisone, Indole derivatives, Oxypertine, Molindone, Sertindole, Ziprasidone, Thioxanthene derivatives, Flupentixol, Clopenthixol, Chlorprothixene, Tiotixene, Zuclopenthixol, Diphenylbutylpiperidine derivatives, Fluspirilene, Pimozide, Penfluridol, Diazepines, oxazepines and thiazepines, Loxapine, Clozapine, Olanzapine, Quetiapine, Neuroleptics, in tardive dyskinesia, Tetrabenazine, Benzamides, Sulpiride, Sultopride, Tiapride, Remoxipride, Amisulpride, Veralipride, Levosulpiride, Lithium, Other antipsychotics, Prothipendyl, Risperidone, Clotiapine, Mosapramine, Zotepine, Aripiprazole, and Paliperidone;

Anxiolytic drug substancessuch as, for example, Benzodiazepine derivatives, Diazepam, Chlordiazepoxide, Medazepam, Oxazepam, Potassium clorazepate, Lorazepam, Adinazolam, Bromazepam, Clobazam, Ketazolam, Prazepam, Alprazolam, Halazepam, Pinazepam, Camazepam, Nordazepam, Fludiazepam, Ethyl loflazepate, Etizolam, Clotiazepam, Cloxazolam, Tofisopam, Diphenylmethane derivatives, Hydroxyzine, Captodiame, Carbamates, Meprobamate, Emylcamate, Mebutamate, Dibenzo-bicyclo-octadiene derivatives, Benzoctamine, Azaspirodecanedione derivatives, Buspirone, Other anxiolytics, Mephenoxalone, Gedocarnil, and Etifoxine Hypnotic and sedative drug substances such as, for example, Barbiturates, Pentobarbital, Amobarbital, Butobarbital, Barbital, Aprobarbital, Secobarbital, Talbutal, Vinylbital, Vinbarbital, Cyclobarbital, Heptabarbital, Reposal, Methohexital, Hexobarbital, Thiopental, Etallobarbital, Allobarbital, Proxibarbal, Aldehydes and derivatives, Chloral hydrate, Chloralodol, Acetylglycinamide chloral hydrate, Dichloralphenazone, Paraldehyde, Benzodiazepineemepronium derivatives, Flurazepam, Nitrazepam, Flunitrazepam, Estazolam, Triazolam, Lormetazepam, Temazepam, Midazolam, Brotizolam, Quazepam, Loprazolam, Doxefazepam, Cinolazepam, Piperidinedione derivatives, Glutethimide, Methyprylon, Pyrithyldione, Benzodiazepine related drugs, Zopiclone, Zolpidem, Zaleplon, Ramelteon, Other hypnotics and sedatives, Methaqualone, Clomethiazole, Bromisoval, Carbromal, Scopolamine, Propiomazine, Triclofos, Ethchlorvynol, Valerian, Hexapropymate, Bromides, Apronal, Valnoctamide, Methylpentynol, Niaprazine, Melatonin, Dexmedetomidine, and Dipiperonylaminoethanol;

Antidepressant drug substancessuch as, for example, Nonselective monoamine reuptake inhibitors, Desipramine, Imipramine, Imipramine oxide, Clomipramine, Opipramol, Trimipramine, Lofepramine, Dibenzepin, Amitriptyline, Nortriptyline, Protriptyline, Doxepin, Iprindole, Melitracen, Butriptyline, Dosulepin, Amoxapine, Dimetacrine, Amineptine, Maprotiline, Quinupramine, Selective serotonin reuptake inhibitors, Zimeldine, Fluoxetine, Citalopram, Paroxetine, Sertraline, Alaproclate, Fluvoxamine, Etoperidone, Escitalopram, Monoamine oxidase inhibitors, non-selective, Isocarboxazid, Nialamide, Phenelzine, Tranylcypromine, Iproniazide, Iproclozide, Monoamine oxidase A inhibitors, Moclobemide, Toloxatone, Other antidepressants, Oxitriptan, Tryptophan, Mianserin, Nomifensine, Trazodone, Nefazodone, Minaprine, Bifemelane, Viloxazine, Oxaflozane, Mirtazapine, Medifoxamine, Tianeptine, Pivagabine, Venlafaxine, Milnacipran, Reboxetine, Gepirone, Duloxetine, Agomelatine, Desvenlafaxine, Centrally acting sympathomimetics, Amphetamine, Dexamphetamine, Metamphetamine, Methylphenidate, Pemoline, Fencamfamin, Modafinil, Fenozolone, Atomoxetine, Fenetylline, Xanthine derivatives, Caffeine, Propentofylline, Meclofenoxate, Pyritinol, Piracetam, Deanol, Fipexide, Citicoline, Oxiracetam, Pirisudanol, Linopirdine, Nizofenone, Aniracetam, Acetylcarnitine, Idebenone, Prolintane, Pipradrol, Pramiracetam, Adrafinil, and Vinpocetine;

Anti-dementia drug substances such as, for example, Anticholinesterases, Tacrine, Donepezil, Rivastigmine, Galantamine, Other anti-dementia drugs, Memantine, Ginkgo biloba;

Other nervous system drug substances such as, for example, Parasympathomimetics, Anticholinesterases, Neostigmine, Pyridostigmine, Distigmine, Ambenonium, Choline esters, Carbachol, Bethanechol, Other parasympathomimetics, Pilocarpine, and Choline alfoscerate;

Drug substances used in addictive disorders such as, for example, drugs used in nicotine dependence, Nicotine, Bupropion, Varenicline, Drugs used in alcohol dependence, Disulfiram, Calcium carbimide, Acamprosate, Naltrexone, Drugs used in opioid dependence, Buprenorphine, Methadone, Levacetylmethadol, Lofexidine. Antivertigo drug substances; Betahistine, Cinnarizine, Flunarizine, Acetylleucine, other nervous system drugs, Gangliosides and ganglioside derivatives, Tirilazad, Riluzole, Xaliproden, Hydroxybutyric acid, and Amifampridine; and Opium alkaloids and derivatives such as, for example, Ethylmorphine, Hydrocodone, Codeine, Opium alkaloids with morphine, Normethadone, Noscapine, Pholcodine, Dextromethorphan, Thebacon, Dimemorfan, Acetyldihydrocodeine, Benzonatate, Benproperine, Clobutinol, Isoaminile, Pentoxyverine, Oxolamine, Oxeladin, Clofedanol, Pipazetate, Bibenzonium bromide, Butamirate, Fedrilate, Zipeprol, Dibunate, Droxypropine, Prenoxdiazine, Dropropizine, Cloperastine, Meprotixol, Piperidione, Tipepidine, Morclofone, Nepinalone, Levodropropizine, and Dimethoxanate.

In certain embodiments, the drug substance included in the immdiate release compositions described herein is selected from the therapeutic classes including non-steroids anti-inflammatory and antirheumatic drug substances.

In other embodiments, the drug substance included in the immediate release composition is selected from the therapeutic classes including analgesics, opioids, antipyretics, anaesthetics, antimigraine agents, antiepileptics, anti-parkinson agents, dopaminergic agents, antipsychotics, anxiolytics, sedatives, antidepressants, psychostimulants agents, dopamine, noradrenaline, nicotinic, alfa-andrenergic, serotonin, $H_3$ antagonist used for ADHD and nootropics agents used in addictive disorders.

In still other embodiments, the drug substance included in the immediate release composition is from the therapeutic classes including anaesthetics, centrally-acting analgesics, sedative-hypnotics, anxiolytics; appetite suppressants, decongestants, antitussives, antihistamines, antiemetics, antidiarrheals, and drugs used to treat narcolepsy and attention deficit hyperactivity disorder.

In other embodiments, the drug substance included in the immediate release composition is associated with abuse syndromes include opioids, CNS depressants, CNS stimulants, cannabinoids, nicotine-like compounds, glutamate antagonists and N-methyl-D-aspartate (NMDA) antagonists.

In yet other embodiments, the drug substance included in the immediate release composition is selected from buprenorphine, codeine, dextromoramide, dihydrocodeine, fentanyl, hydrocodone, hydromorphone, morphine, pentazocine, oxycodeine, oxycodone, oxymorphone and tramadol.

In still other embodiments, the drug substance included in the immediate release composition is selected from amphetamine, metamphetamine dexamphetamine, lisdexamphetamine, methylphenidate and dexmethylphenidate.

In still other embodiments, the drug substances included in the immediate release composition have abuse potential or safety risk. In principle, the use of a composition to avoid alcohol dose dumping can be of relevance for any drug substance. However, the potential abuse deterrence provided by the immediate release compositions described herein that are resistant to dose dumping in the presence of alcohol are particularly beneficial for drug substances with abuse potential or safety risk.

Examples of drug substances that present a potential for abuse or a potential safety risk and are suitable for use in the immediate release compositions described herein include:

1-(1-Phenylcyclohexyl)pyrrolidine, 1-(2-Phenylethyl)-4-phenyl-4-acetoxypiperidine, 1-[1-(2-Thienyl)-cyclohexyl]piperidine, 1-[1-(2-Thienyl)cyclohexyl]pyrrolidine, 1-Methyl-4-phenyl-4-propionoxy-piperidine, 1-Phenylcyclohexylamine, 1-Piperidinocyclohexane-carbonitrile, 2,5-Dimethoxy-4-ethylamphetamine, 2,5-Dimethoxyamphetamine, 2C-B (i.e. 4-bromo-2,5-dimethoxypenethylamine), 2C-D (i.e. 2,5-dimethoxy-4-methylphenethylamine), 2C-I (i.e. 4-iodo-2,5-dimethoxy-phenethylamine), 2C-T-2 (i.e. 2,5-dimethoxy-4-ethylthiophenethylamine), 2C-T-4 (i.e. 2,5-dimethoxy-4-isopropyl thiophenethylamine), 2C-T-7 (i.e. 2,5-dimethoxy-4-(n)-propylthiopenethylamine), 3,4-Methylene-dioxymethamphetamine, 3,4,5-Trimethoxyamphetamine, 3,4-Methylene-dioxyamphetamine, 3,4-Methylenedioxy-N-ethylamphetamine, 3-Methylfentanyl, 3-Methylthiofentanyl, 4-Bromo-2,5-dimethoxyamphetamine, 4-Bromo-2,5-dimethoxy-phenethylamine, 4-Methoxyamphetamine, 4-Methyl-2,5-dimethoxyamphetamine, 4-Methylaminorex (cis isomer), 5-MeO-DIPT (i.e. 5-Methoxy-N,N-diisopropyltryptamine), 5-MeO-DMT (i.e. 5-Methoxy-N,N-dimethyltryptamine), 5-Methoxy-3,4-methylenedioxy-amphetamine, Acetorphin, Acetorphine, Acetyl-alpha-methylfentanyl, Acetyldihydro-codeine, Acetylmethadol, Alfentanil, Allobarbital, Allylprodin, Allylprodine, Alphacetylmethadol, levo-alphacetylmethadol, Alpha-ethyltryptamine, Alphameprodine, Alphamethadol, Alpha-Methylfentanyl, Alpha-Methylthiofentanyl, Alphaprodine, Alprazolam, Amfepramon, Amfetaminil, Amineptin, Aminorex, Amobarbital, Amphetamine, Dexamphetamine, Lisdexamphetamine, Amylnitrit (all isomers of the amyl group), Anabolic steroids, Anileridine, Aprobarbital, Barbital, Barbituric acid derivative, BDB (i.e. 3,4-methylenedioxyphenyl)-2-butanamine), Benzethidin, Benzethidine, Benzoylecgonine, Benzphetamine, Benzphetamine, Benzylmethylketon, Benzylmorphine, Betacetylmethadol, Beta-Hydroxy-3-methylfentanyl, Beta-Hydroxyfentanyl, Betameprodine, Betameprodine, Betamethadol, Betaprodine, Bezitramide, Bezitramide, Boldenone, Brolamfetamin, Bromazepam, Brotizolam, Bufotenine, Buprenorphine, Butabarbital, Butalbital, Butobarbital, Butorphanol, BZP (A 2)(i.e. 1-benzylpiperazin), Camazepam, Cannabis, Carfentanil, Catha edulis, Cathine, Cathinone, Chloral betaine, Chloral hydrate, Chlordiazepoxide, Chlorhexadol, Chlorotestosterone (same as clostebol), Chlorphentermine, Clobazam, Clonazepam, Clonitazene, Clonitazene, Clorazepate, Clortermine, Clostebol, Clotiazepam, Cloxazolam, Coca Leaves, Cocaine, Codeine, Codeine & isoquinoline alkaloid, Codeine methylbromide, Codeine-N-oxide, Codoxim, Cyclobarbital (Hexemal NFN), Cyprenorphine, Dehydrochlormethyltestosterone, Delorazepam, Desomorphine, Dexamphetamine, Dexfenfluramine, Dextromoramide, Dextropropoxyphene, Diacetylmorphine, Diampromide, Diazepam, Dichloralphenazone, Diethylpropion, Diethylthiambutene, Diethyltryptamine, Difenoxin, Dihydrocodeine, Dihydroetorphine, Dihydromorphine, Dihydrotestosterone, Dimenoxadol, Dimepheptanol, Dimethyl-thiambutene, Dimethyltryptamine, Dioxaphetyl butyrate, Diphenoxylate, Dipipanone, Diprenorphine, Dronabinol, Drostanolone, Drotebanol, Ecgonine, Estazolam, Ethchlorvynol, Ethinamate, Ethyl loflazepate, Ethylestrenol, Ethylmethylthiambutene, Ethylmorphine, Ethylmorphine, Eticyclidin, Etilamphetamine, Etonitazene, Etorphine, Etoxeridine, Etryptamine, Fencamfamin, Fenethylline, Fenetylline, Fenfluramine, Fenproporex, Fentanyl, Fludiazepam, Flunitrazepam, Fluoxymesterone, Flurazepam, Formebolone, Fungi and Spores of the species Psilocybe Semilanceata, Furethidine, Gammahydroxybutanic acid, Glutethimide, Halazepam, Haloxazolam, Heroine, Hydrocodone, Hydrocodone & isoquinoline alkaloid, Hydromorphinol, Hydromorphone, Hydroxypethidine, Ibogaine, Isobutylnitrit, Isomethadone, Ketamine, Ketazolam, Ketobemidone, Levamphetamine, Levo-alphacetylmethadol, Levo-methamphetamine, Levomethorphan, Levomoramide, Levophenacylmorphan, Levorphanol, Loprazolam, Lorazepam, Lormetazepam, Lysergic acid, Lysergic acid amide, Lysergic acid diethylamide, Marijuana, Mazindol, MBDN (i.e. N-methyl-1-(3,4-methylene-dioxyphenyl)-2-butanamine), mCPP (i.e. 1-(3-chlorophenyl)piperazine), Mebutamate, Mecloqualone, Medazepam, Mefenorex, MeOPP (i.e. 1-(4-methoxyphenyl)piperazine), Meperidine, Meperidine intermediate, Meprobamate, Mescaline, Mesocarb, Mesterolone, Metamphetamine, Metazocine, Methadone, Methadone intermediate, Methamphetamine, Methandienone, Methandranone, Methandriol, Methandrostenolone, Methaqualone, Methcathinone, Methenolone, Methohexital, Methyldesorphine, Methyldihydromorphine, Methylphenidate, Dexmethylphenidate, Methylphenobarbital (mephobarbital), Methyltestosterone, Methyprylone, Metopone, Mibolerone, Midazolam, Modafinil, Moramide-intermediate, Morpheridine, Morphine, Morphine methylbromide, Morphine methylsulfonate, Morphine-N-oxide, Myrophine, N,N-Dimethylamphetamine, Nabilone, Nalorphine, Nandrolone, N-Ethyl-1-phenyl-cyclohexylamine, N-Ethyl-3-piperidyl benzilate, N-Ethylamphetamine, N-Hydroxy-3,4-methylenedioxyamphetamine, Nicocodeine, Nicocodine, Nicodicodine, Nicomorphine, Nimetazepam, Nitrazepam, N-Methyl-3-piperidyl benzilate, Noracymethadol, Norcodeine, Nordiazepam, Norethandrolone, Norlevorphanol, Normethadone, Normorphine, Norpipanone, Norpipanone, Opium, Oxandrolone, Oxazepam, Oxazolam, Oxycodone, Oxymesterone, Oxymetholone, Oxymorphone, Para-Fluorofentanyl, Parahexyl, Paraldehyde, Pemoline, Pentazocine, Pentobarbital, Petrichloral, Peyote, Phenadoxone, Phenampromide, Phenazocine, Phencyclidine, Phendimetrazine, Phenmetrazine, Phenobarbital, Phenomorphan, Phenoperidine, Phentermine, Phenylacetone, Pholcodine, Piminodine, Pinazepam, Pipradrole, Piritramide, PMMA (paramethyxymethyl amphetamine), Prazepam, Proheptazine, Properidine, Propiram, Psilocybine, Psilocyn, Pyrovalerone, Quazepam, Racemethorphane, Racemoramide, Racemorphane, Remifentanil, Salvia divinorum, Salvinorin A, Secobarbital, Secobarbital, Sibutramine, SPA, Stanolone, Stanozolol, Sufentanil, Sulfondiethylmethane, Sulfonethylmethane, Sulfonmethane, Talbutal, Temazepam, Tenamfetamin, Testolactone, Testosterone, Tetrahydrocannabinols, Tetrazepam, TFMPP (i.e. 1-(3-trifluormethylphenyl)piperazine), Thebacon, Thebaine, Thiamylal, Thiofentanyl, Thiopental, Tiletamine & Zolazepam in Combination, Tilidine, Trenbolone, Triazolam, Trimeperidine, Vinbarbital, Zaleplon, Zipeprol, Zolpidem, and Zopiclon.

Additional examples of drug substances that present a potential for abuse or a potential safety risk and are suitable for use in the immediate release compositions described herein include: alfentanil, allylprodine, alphaprodine, aniloridine, benzylmorphine, bezitramide, buprenorphine, butophanol, clonitazene, codeine, cyclazocine, desomorphine, dextromoramide, dezocine, diapromide, dihydrocodeine, dihydromorphine, dimenoxadol, dimephetanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, dextropropoxyphene, ketobemidone, levallorphan, levorphanol, levophenacylmorphan, lofentanil, meperidine, meptazinol, metazocine, methadone, metopon, morphine, morphine 6-glucuronide, morphine 3-glucuronide, myrophine, nalbuphine, narccine, nicomorphine, norlevorphanol, normethadone, nalorphine, normorphine, norpipanone, opium, oxycodone, oxycodeine, oxymorphone, papaveretum, pentazocine, phenadoxone, phenomorphan, phenazocine, phenoperidine, piminodine, piritramide, propheptazine, promedol, properidine, propiram, propoxyphene, sufentanil, tilidine, tramadol, thebaine, levo-alphacetylmethadol (LAAM), remifentanil, carfentanyl, ohmefentanyl, MPPP (ie. 1-methyl-4-phenyl-4-propionoxypiperidine), prodine, PEPAP (ie. 4-phenyl-1-(2-phenyl-ethyl)piperidin-4-yl acetate), levomethorphan, etorphine, lefetamine, loperamide, diphenoxylate, and pethidine.

Even further examples of drug substances that present a potential for abuse or a potential safety risk and are suitable for use in the immediate release compositions described herein include anabolic steroids, cannabis, cocaine and diazepam.

The above mentioned drug substances may be incorporated in the immediate release compositions described herein in any suitable form, such as, for example, as pharmaceutically acceptable salts, uncharged or charged molecules, molecular complexes, solvates or anhydrates, and, if relevant, isomers, enantiomers, racemic mixtures, and/or mixtures thereof. Furthermore, the drug substance may be in any of its crystalline, polymorphous, semi-crystalline, and amorphous or polyamorphous forms.

If desired, the drug substance included in the immediate release compositions described herein may be modified to change physical-chemical properties of the drug substance, which may, for example, be carried out by increasing or decreasing lipophilicity to modify the release characteristics of the drug substance.

The term "pharmaceutically acceptable salts" of a drug substance includes alkali metal salts such as, for example, sodium or potassium salts, alkaline earth metal salts such as, for example, calcium and magnesium salts, and salts with organic or inorganic acid like, for example, hydrochloric acid, hydrobromic acid, nitric acid, sulfuric acid, phosphoric acid, citric acid, formic acid, maleic acid, succinic acid, tartaric acid, methansulphonic acid, toluenesulphonic acid, etc.

The term "solvates" includes hydrates or solvates wherein other solvates than water are involved such as, for example, organic solvents like chloroform and the like.

The concentration of the drug substance included in an immediate release composition described herein will depend on several factors, including, for example, the specific drug substance, the disease to be treated, the condition of the patient, the age and gender of the patient, etc. The above-mentioned drug substances are well-known drug substances and a person skilled in the art will be able to find information as to the dosage of each drug substance and, accordingly, will know how to determine the amount of each drug substance in a composition.

It is also contemplated, however, that the immediate release compositions described herein may be used to deliver new drug substances. Where the drug substance is a new chemical entity for which the amount of dosing information is limited, the concentration and delivered dose provided by the immediate release composition may be evaluated and selected on, for example, any available preclinical or clinical data.

In specific embodiments, the drug substance included in the immediate release formulations described herein is present in a concentration selected from about 0.01% w/w to about 99% w/w, about 0.01% w/w to about 90% w/w, about 0.01% w/w to about 80% w/w, about 0.01% w/w to about 70% w/w, about 0.01% w/w to about 50% w/w, and from about 0.01% w/w to about 40% w/w.

In one embodiment, the drug substance included in the immediate release composition is provided as a pharmaceutically active powder. Where the active agent is provided as a powder, the powder may exhibit a particle size selected from about 0.1 µm to about 500 µm, about 0.5 µm to about 300 µm, about 1 µm to about 200 µm, and about 5 µm to about 100 µm.

In one embodiment, the drug substance included in the immediate release composition is provided in its crystalline form. In one such embodiment, the crystalline drug substance exhibits a particle size selected from about 0.1 µm to about 1000 µm, about 0.1 µm to about 750 µm, about 0.1 µm to about 500 µm, about 0.5 µm to about 500 µm, about 1 µm to about 500 µm, and about 5 µm to about 500 µm.

In another embodiment, the drug substances provided in an immediate release composition as described herein is provided in a form that is at least partially amorphous. In one such embodiment, the mean particle size of drug substance material may be selected from at least about 0.01 µm such as, for example, from about 0.01 µm to about 500 µm, from about 0.05 µm to about 500 µm, from about 0.1 µm to about 500 µm, from about 0.5 µm to about 500 µm, from about 1 µm to about 500 µm, from about 0.5 µm to about 300 µm, from about 1 µm to about 200 µm, and from about 1 µm to about 100 µm.

The immediate release compositions described herein are typically prepared for oral administration. The formulation of the immediate release compositions described herein may be adjusted to suit a desired dosing regimen. For example, the immediate release compositions described herein may be adapted for oral administration 1-6 times a day. In specific embodiments, the immediate release composition may be formulated to be administered, for example, 1-4 times daily, 1-3 times daily, and 1-2 times daily or once a day.

Pharmaceutical Compositions

A number of pharmaceutical compositions were developed to reduce the likelihood of improper administration of drugs in combination with alcohol, especially drugs such as opioids or combinations of opioids and relevant drug compounds such as paracetamol or ibuprofen. In specific embodiments, analgesics. antipyretics, or CNS drug substances are included in the immediate release compositions described herein to provide a pharmaceutical composition. Specific examples of drug substances suitable for use in the compositions described herein are described above.

In particular embodiments, a pharmaceutical composition according to the present description includes an immediate release composition as described herein. In certain such embodiments, the immediate release composition may be formed as a matrix composition. In such embodiments, the immediate release composition may include one or more polyglycols as described herein. In specific embodiments, such compositions provide a lower solubility and/or release rate of drug substance when placed in alcohol (such as ethanol) containing media than in aqueous media (such as water, buffer, hydrochloride solution). As demonstrated in the examples herein, the alcohol containing media may include an alcohol, such as ethanol, in a wide concentration range. Thus, in particular embodiments, relative to the solubility and/or release rate of a drug substance exhibited in a dissolution environment substantially free of alcohol, the immediate release compositions described herein provide lower solubility and/or release rate of drug substance when placed in a dissolution environment wherein the dissolution media contains from about 2.5% v/v to about 80% v/v of alcohol, the remaining part being an aqueous medium (i.e. water, aqueous buffer or hydrochloride solution).

Therefore, in particular embodiments, the immediate release compositions described herein provide a pharmaceutical composition that does not exhibit alcohol-induced dose dumping. In such embodiments, the solubility or release rate of the drug substance included in the immediate release composition is lower in aqueous dissolution environments that include alcohol than that in aqueous dissolution environments that are free of alcohol. More specifically, when compared to the solubility and release rate of drug substance in a dissolution environment free of alcohol, in certain such embodiments, the solubility or release rate of drug substance from an immediate release composition described herein is selected from at least 1.5 times lower, at least 2 times lower, at least 5 times, at least 10 times lower, at least 25 times lower, at least 50 times lower and at least 100 times lower in an aqueous dissolution environment containing alcohol.

As illustrated in the Examples herein, an immediate release composition as described herein may be a coated matrix composition. The release rate provided by such a composition may be governed by erosion of the amount of surface area of the composition exposed to the dissolution environment, and the area of the composition exposed for erosion may be manipulated by employment of a coat that is not subject to erosion. For example, a relatively high rate of release may be achieved where the composition is free of a coating that is not subject to erosion, and a relatively lower rate of release may be achieved by coating progressively more of the outside surface of the immediate release composition with a coating that is not subject to erosion. For such compositions the geometric form of the composition can also be important for achieving a desired rate of release. Thus, in one embodiment, the immediate release composition described herein is a matrix composition exhibiting a geometric shape that enables a substantially constant surface area to become exposed during erosion of the matrix.

In a specific example, the matrix compositions employed are coated in such a manner that the surface has a substantially constant or controlled surface area during release or erosion. In the present context, controlled surface area relates to a predetermined surface area typically predicted from the shape of the coat of the unit dosage system. It may have a simple uniform cylindrical shape or the cylindrical form can have one or more tapered ends in order to decrease (or increase) the initial release period.

As another example, in diffusion based compositions, the release will furthermore depend on the thickness of the diffusion layer, and in such an embodiment, the release will depend both on the diffusion area and thickness of the diffusion composition.

As yet another example the release mechanism of dissolving/solubilisation also depends on the area of the composition exposed to the dissolution environment, and the release rate may be controlled by controlling the surface area of the composition exposed to the dissolution environment. Again, for example, varying release rates of the drug substance may be achieved by coating varying amounts of the outside surface of the composition with a coating that is not subject to erosion in the dissolution environment.

The composition may be partly or fully covered by a coat with specific properties in such a way that the exposed area of the matrix may be controlled by the use of a coat.

Where the release rate of the drug substance from the compositions described herein is to be controlled or adjusted using a non-erodible coating as described herein, 0 to 99% of outside surface of the composition may be covered by the non-erodible coating.

A composition as described herein is normally prepared for oral intake, preferably for oral intake by swallowing. Accordingly, the size of the composition is desirably in a range that allows oral intake by swallowing.

Geometry

In particular embodiments, the pharmaceutical compositions described herein are formed as cylindrical compositions. Such cylindrical compositions may optionally be formed with one or two tapered end(s). In certain such embodiments, the pharmaceutical compositions are formed as a matrix composition having a cylindrical shape (optionally with one or two tapered end(s)), and such embodiments may further include a coating that does not erode in the dissolution environment, is positioned over at least a portion of the outside surface of the cylindrical, matrix composition, and has at least one opening exposing one surface of the matrix composition. For purposes of the compositions described herein, the cylindrical shape may be any geometrical shape having the same cross section area throughout the length of the geometrical shape. Within the present context, cross sections are perpendicular to the axis of the cylinder. By way of example, if the cylindrical shape is elongated then the cross sections are perpendicular to the longitudinal axis. Preferably, the cylindrical shape is elongated. The cross section of a cylinder within the meaning of the present invention may have any two-dimensional shape, for example the cross section may be circular, oval, parabola, hyperbola, rectangular, triangular, otherwise angular, star shaped or an irregular shape. In certain embodiments, the pharmaceutical compositions described herein have a cylindrical shape, wherein one or two end(s) are tapered. Accordingly, the cylindrical shape may for example be an elliptic cylinder, a parabolic cylinder, a hyperbolic cylinder or a prism. A prism within the present context is a cylinder whose cross-section is a polygon.

Where a pharmaceutical composition as described herein includes a coating that does not eroded in the dissolution environment, the coating provides at least one opening through which the surface of the matrix composition is exposed to the dissolution environment. In certain embodiments, the pharmaceutical compositions described herein are formed by a cylindrical matrix composition as described herein having two ends, wherein the matrix composition is substantially surrounded by a coating that does not erode in the dissolution environment and includes two openings, each of the openings in the coating exposing an end of the cylindrical shape.

Coating

The compositions described herein may be partly covered by a coat with specific properties in such a way that the exposed area of the composition is controlled. By controlling the exposed surface area of the pharmaceutical composition the release rate of drug substance from pharmaceutical compositions described herein can be controlled.

If the coating is to be used as a means for controlling erosion or dissolution of the pharmaceutical composition, the coating will typically be selected to be impermeable to an aqueous dissolution medium, such as water. This ensures that the matrix only is in contact with surrounding aqueous media via the openings in the coating. In addition to being impermeable to the aqueous dissolution medium, the coating material can be selected such that it is substantially insoluble to insoluble in an aqueous environment.

In a specific example the coating is substantially insoluble, non-erodable and impermeable to water leaving only the exposed areas of the pharmaceutical composition for release of drug substance. Within the present context, the coating is considered substantially insoluble in an aqueous medium if the coating dissolves so much slower in an aqueous medium than the pharmaceutical composition that the coating remains intact until the pharmaceutical composition has eroded and/or released the drug substance.

In an embodiment of the invention, the coating biodegrades, disintegrates crumbles, or dissolves after erosion of the matrix and/or during the release of the drug substance. In certain embodiments, a coating applied to a matrix composition as described herein will remain intact as long as it is supported by the matrix composition containing the drug substance. In specific embodiments, the coating may be is formulated to lose the ability to remain intact after erosion of the matrix composition. For example, the coating may be formulated to biodegrades, disintegrates or crumbles upon erosion of the matrix composition, so that the coating will not remain in a subject to whom the pharmaceutical composition is administered, e.g., a human, for any significant amount of time after the complete erosion of the matrix and the release of the drug substance.

In a one embodiment, the coating may biodegrade, disintegrate, crumble or dissolve after erosion of the matrix composition and/or during the release of the drug substance in the matrix composition.

The coating may in general comprise or even consist of one or more polymers. Polymers suited for forming the coating that substantially covers the matrix composition may be selected from thermoplastic polymers. In one embodiment, the coating is formed entirely of thermoplastic polymers. Thus, in one embodiment of the invention all the polymers included in the coating are thermoplastic polymers. As used herein, the term "thermoplastic polymer" refers to polymer(s) that is/are an elastic and flexible liquid when heated, but freezes to a solid state when cooled (e.g., cooled to 20° C. or to ambient temperature).

The coating may be made of a material comprising one or more of the polymers described herein in this section, such as, for example, a material comprising one or more starch based polymers, one or more cellulose based polymers, one or more synthetic polymers, one or more biodegradable polymers or a combination thereof, such as mixtures of starch and synthetic polymers or mixtures of starch and biodegradable polymers. In certain embodiments, the coating may be made of a material comprising one or more polymers selected from the group consisting of Ethyl cellulose grade 20 and 100, polylactic acid (PLA), Cornpack 200, polycaprolactone, PEO 7000000 and polyhydroxybuturate.

Starch Based Polymers

The coating may comprise one or more starch based polymers. The starch based polymer may be starch as such or a polymer having a high starch content, preferably more than 70%, such as more than 80%, for example more than 90%. Starch is a linear polysaccharide made up of repeating glucose groups with glycosidic linkages in the 1-4 carbon positions with chain lengths of 500 to 2,000 glucose units. There are two major polymer molecules in starch-amylose and amylopectin.

The starch based polymers to be used according to the present invention may preferably be thermoplastic starch biodegradable plastics (TPS). TPS have a starch (amylose) content greater than 70% and are in general based on gelatinized vegetable starch. Said vegetable starch may for example be selected from the group consisting of potato starch, rice starch, maize starch, tapioca starch, wheat starch, dextrin, carrageenan and chitosan. Said vegetable starch may also as such be suitable polymers used in the coating composition. The group of starch based polymer in general do not have a specified melting point, but changes phase within a temperature range of 90° C. to 260° C. typically depending upon the chain length of the starch based polymer, water content, and their branching and added side-groups as does the degree of crystallinity of the starch. Long chained-starches are usually completely amorphous, while shorter length starches may be semi-crystalline (20-80% crystalline). Long polymer chains are preferable because it contributes to the hardness, while not being too brittle.

Starch-based polymers are in general fully biodegradable as they are product of plant materials. The degradation rate varies and can be further induced by addition of other biodegradable polymers as listed herein.

One example of a preferred starch based polymer, which may be comprised in the coating or coating according to the present description is maize starch. Maize starch is a linear polysaccharide made up of repeating glucose groups with glycosidic linkages in the 1-4 carbon positions with chain lengths of 500 to 2,000 glucose units. There are two major polymer molecules in starch, amylose and amylopectin. A preferred maize starch is cornpack. Cornpack is the maize starch used in some examples described herein below.

Starch is widely used in food and pharmaceutical industry as binder and diluent. It is edible and essentially nontoxic. Starch is in general cheap and obtains a good hardness when molded and thermoformed. Starch may in general also be reheated several times without losing its thermodynamic properties. Accordingly, in certain embodiments, the coating comprises at least one starch based polymer, and more preferably a starch, because starch may be a great advantage when applying injection molding or co-extrusion as a production process.

Starch based polymers are in general decomposable, and usually have a fast disintegration rate, especially in mixture with biodegradable polymers. These polymers are in generally recognized as stabile and inert in solid dosage forms.

Cellulose Based Polymers

The coating may also comprise one or more cellulose based polymers. In certain embodiments of the invention the coating may even consist of one or more cellulose based polymers (such as ethyl cellulose) and plasticizers (such as any of the plasticizers described in this section below) and UV stabilizers (such as any of the UV stabilizers described in this section below).

Cellulose based polymers are useful in the coating composition because cellulose based polymers e.g. ethyl cellulose (particularly grade 100-300) frequently have increased hardness and high ductility.

Therefore the coatings used over the matrix composition may include a cellulose based polymer. Where a cellulose based polymer is used in the coating, it is preferably a cellulose based that is substantially insoluble or insoluble in an aqueous medium. Suitable cellulose based polymers include cellulose polymers wherein one or more of the free —OH groups have been substituted with an R-group to form a —O—R group. In this context, R may be, for example, a linear or branched lower alkyl, linear or branched lower alkyl-OH, linear or branched lower alkyl-COOH, —CO-(linear or branched lower alkyl), nitrate, aromatic rings or combinations of the aforementioned. Lower alkyl is preferably a $C_{1-10}$ alkyl, more preferably $C_{1-6}$ alkyl.

Accordingly, where a cellulose based polymer is used in a coating as described herein, the cellulose based polymer may, for example, be one or more selected from ethylcellulose, cellulose acetate, cellulose propionate, cellulose nitrate, methylcellulose, carboxymethylcellulose and salts thereof, cellulose acetate phthalate, ethylhydroxyethylcellulose, ethylmethylcellulose, hydroxymethylcellulose, hydroxyethylmethylcellulose, hydroxypropylcellulose, hydroxypropylmethylcellulose, hydroxymethylcellulose and hydroxymethylpropylcellulose and cellulose acetate.

The coating may also comprise one or more cellulose based polymers selected from cellulose acetate, cellulose propionate, silicified microcrystalline cellulose, cellulose nitrate, methylcellulose, carboxymethylcellulose and salts thereof, cellulose acetate phthalate, microcrystalline cellulose, ethylhydroxyethylcellulose, ethylmethylcellulose, hydroxyethylcellu lose, hydroxyethylmethylcellu lose, hyd roxyl propylcellu lose, hydroxypropylmethylcellulose, hydroxymethylcellulose phthalate, hydroxymethylcellulose and hydroxymethylpropylcellulose, cellulose acetate, ceratonia (high molecular-weight 310 000).

Cellulose based polymers are in general fully biodegradable, as they are typically products of plant materials. The degradation rate of cellulose based polymers is generally slower than for starch based polymers. The degradation rate of cellulose based polymers, however, can be induced by addition of other biodegradable polymers as listed herein. Such additional polymers may be polymers susceptible to degradation by one or more microorganisms, which can result in quicker degradation of the coating composition into smaller pieces, giving rise to an increased surface area, and, thereby, resulting in faster degradation.

In a specific embodiment, the coating comprises ethyl cellulose $C_{12}H_{23}O_6(C_{12}H_{22}O_5)_nC_{12}H_{23}O_5$, wherein n can vary to provide a wide variety of molecular weights. Ethylcellulose, an ethyl ether of cellulose, is a long-chain polymer of β-anhydroglucose units joined together by acetal linkages. Ethyl cellulose comes in different grades which vary in molecular weight and number of ethoxy groups. Grades from 20-300 are suitable for use in the present context and are also readily commercially available. Grades with high molecular weights tend to be preferred because they are optimal to give a hard coating. The coating may comprise one or more ethyl celluloses with different grades, for example one ethyl cellulose with a grade of in the range of 20 to 300, preferably in the range of 20 to 100, more preferably in the range of 20 to 40, such as 20 and another ethyl cellulose with a grade of in the range of 20 to 300, preferably in the range of 50 to 200, more preferably in the range of 80 to 120, such as 100. Ethyl cellulose generally has a glass transition temperature within 129-133° C. These polymers are widely used in food and pharmaceutical industry as coater, stabilizer, matrix former and taste masking and are regarded as non toxic substances.

Cellulose based polymers are in general derived from plant material and may subsequently be modified. Many cellulose based polymers are cheap and give a good hardness when molded and thermoformed. As derivatives of plants, cellulose based polymers are in general easily decomposable when disposed. These polymers tend to be stable and inert in solid dosage.

Synthetic Polymers

The coating according to the invention may also comprise one or more synthetic polymers. Suitable synthetic polymers for use in the coating composition may, for example, be one or more selected from the group consisting of polyamide, polyethylene, polyethylene terephthalate, polypropylene, polyurethane, polyvinyl acetate, polyvinyl alcohol, polyvinyl butural, Eudragit L methyl ester, Eudragit RL and Eudragit E. polyvinyl chloride, silicone rubber, latex, teflon, copolymers such as ethylene vinyl acetate (EVA), styrene-butadienestyrene (SBS) and styrene-isoprene-styrene (SIS), Polyethylene glycols, polyvinylpyrrolidone, polyethylene oxide (ranging in molecular weights 100,000 to 8,000,000), carboxymethylene (Carbomer) and sugars thereof (e.g. allylsucrose) and co-polymers of ethylene and propylene oxide (PoloXamer).

Biodegradable Polymers

Biodegradation is the process by which microorganisms (microbes such as bacteria, fungi or algae) convert materials into biomass, carbon dioxide and water. Biomass is a general term used to refer to the cells of the microorganisms that are using the material as a carbon source to grow on.

The coating may also comprise one or more biodegradable polymers. Said biodegradable polymer(s) may be one or more selected from starch based polymers as described herein above in this section and cellulose based polymers as described herein above in this section. However, the biodegradable polymer may also one or more selected from polyhydroxybutyrate (PHB), polyhydroxyvalerate (PHV), polyhydroxyvalerate-co-hydroxyvalerate (PHV/VH), Polyhydroxyalkanoates (PHA), poly-3-hydroxy-5-phenylvalerate (PHPV), aliphatic polyesters, polycaprolactone (PCL), polylactic acid (PLA), polyglycolic acid (PGA), copolymers or block copolymers of poly-caprolactone (PCL), polylactic acid (PLA) and/or polyglycolic acid (PGA), poly-propylene carbonate (PPC), polyester amide (PEA), polybutylene succinate adipate (PBSA), polybutylene adipate co-terephtalate (PBAT) and polybutylene succinate-adipate (PESA).

Copolymers or block copolymers of polycaprolactone (PCL), polylactic acid (PLA) and/or polyglycolic acid (PGA) may, for example, be selected from, poly(lactic-co-glycolic acid)(PLGA), polylactic acid and epsilon-caprolactone copolymer (PLA/CL) and polylactic acid/glycolic acid polymers)(PLA/GA), which are all commercially available.

In one embodiment, the coating comprises one or more biodegradable polymers selected from polylactic acid (PLA), polycaprolactone (PCL) and polyhydroxybutyrate (PHB). In one such embodiment, the coating comprises both polylactic acid (PLA), polycaprolactone (PCL) and polyhydroxybutyrate (PHB).

The use of polycaprolactone and other polymers in this group has been increased over the last decade, while the demand for environmental friendly plastics has grown. These polymers are regarded as nontoxic and are already used in parenteral pharmaceutical formulations. The advantages of these polymers are their ability to make a more flexible coating when molded in mixture with starch derived polymers. The somewhat rigid structure of pure thermoplastic starch is improved. Furthermore the polymers are decomposable and disintegrate by microorganisms.

Polylactic Acid

Polylactic acid or polylactide (PLA) is a biodegradable, thermoplastic, aliphatic polyester derived from renewable resources, such as corn starch. PLA belongs to the chemical family of polyesters, such as e.g. ε-caprolactone, PLA-caprolactone in different ratios 15% PLA to 100% (25, 35, 50, 75, 85%), polyglycolides, polyglycolic acids (PGA), poly (lactide-co-glycolide) in different ratios 15 to 100% PLA (25, 35, 50, 75, 85%), poly (lactide-co-glycolide)-OH in different ratios 15% PLA to 100% (25, 35, 50, 75, 85%). Each of the before mentioned polymers exist in L or D-form (making them optically active) and in equal amounts (1:1) of L- and D-forms results in an amorphous mixture, while the L- or D-form all possess a certain degree of crystallinity. The degree of crystallinity is highly related to the mechanical properties (incl. processability), physico-chemical properties related to particularly stability of the polymer. A high degree of crystallinity provides hardness, and possibly, more brittleness. This may affect processability as well as highly crystalline materials have a high melting temperature, hence process temperature, while amorphous esters have a lower melting temperature and thus a lower process temperature.

Moreover, an increased degree of crystallinity implies that the material is more thermodynamically stable, which leads to a longer shelf-life. A lower degree of crystallinity or amorphous materials are usually softer with a lower process temperature. A potential drawback of amorphous materials or materials with a lower degree of crystallinity is that their physical-chemical stability is lower due to their relatively thermodynamically unstable state.

Regarding PLA, it is necessary to find the optimal degree of crystallinity. Each degree of crystallinity has different mechanical properties, thus its adhesion to the matrix will vary depending on the degree of crystallinity of the given material (PLA).

The skeletal structure of PLA is shown below.

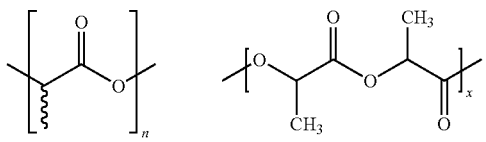

Due to the chiral nature of lactic acid, several distinct forms of polylactide exist: poly-L-lactide (PLA in its L-form) referred to as PLLA is the product resulting from polymerization of L,L-lactide (also known as L-lactide) and poly-D-lactide (PLA in its D-form) referred to as PDLA is the product resulting from polymerization of L,L-lactide (also known as L-lactide). Furthermore, PLLA and PDLA may be mixed with various ratios of the two stereo forms. As the L-form has stronger mechanical properties than the D-form and the L-form has been used in pharmaceutical products, it is attempted to optimize the blend by adding the D-form to the L-form, such as, for example, in amounts of 5, 10, 20, 30, 40% w/w, up to a ratio of 1:1, consequently making the material completely amorphous. However, it may also form a highly regular stereo complex with increased crystallinity. Addition of PDLA increases the molecular energy of the mixture by forming a concentration gradient, and depending on the extent/magnitude of the temperature gradient, it may induce slow nucleation and hence crystallization. However, it may as well induce a nucleation with an uncontrollable nucleation rate, which leads to an amorphous state.

PLA in its L-form has a crystallinity of around 35-45%, a glass transition temperature between 35-80° C. and a melting temperature between 173-178° C.

Due to the structure of PLA, PLA may be exposed to hydrolysis during its path through the gastro-intenstinal tract, but PLA is impermeable and insoluble in aqueous media. In applying PLA as shell material, it has been demonstrated that the shell remains intact, at least macroscopically, within the first 48 hours of exposure. Furthermore, the possible degradation product of PLA is merely lactic acid.

Polyglycols

The coating may comprise any of the above-mentioned polyglycols in a form that erodes at a substantially slower rate than the matrix composition. The coating may thus be one which is eroded in an aqueous medium at a substantially slower rate than the matrix composition comprising the active drug substance, whereby the area of the matrix composition comprising the active drug substance that is exposed during erosion and/or release of the matrix composition is substantially controlled, and whereby the coating is substantially eroded upon erosion and/or release of the matrix composition comprising the active drug substance. Such a coating can be designed so that its longitudinal erosion rate is substantially the same as the longitudinal erosion and/or release rate of the matrix, whereby the matrix and the coating will erode longitudinally towards the centre of the composition at substantially the same rate. Thus, when the matrix composition has been completely eroded and/or released by the aqueous medium, the coating will also be substantially completely eroded. A matrix composition having such a coating has the obvious advantage of being completely biodegraded upon release of the active drug substance.

A polyglycol suitable for use within the coating is high molecular weight PEO, such as, for example, PEO with an average molecular weight which is significantly higher than the average molecular weight of any of the PEOs contained in the matrix composition. Thus, where the coating composition includes a PEO, the PEO contained in the coating can be selected to have a significantly higher average molecular weight than any PEO contained in the matrix. Examples of PEO materials suited to use in the coating include, for example, one or more PEO with an average molecular weight selected from at least 900,000, at least 2,000,000, at least 4,000,000, at least 6,000,000, or at least 7,000,000.

Mixtures of Polymers

As noted herein above the coating may comprise one or more different polymers, and in particular one or more different polymers selected from the group consisting of starch based polymers, cellulose based polymers, synthetic polymers and biodegradable polymers, in particular from the group consisting of any of the starch based polymers, cellulose based polymers, synthetic polymers and biodegradable polymers described herein above in this section.

In one embodiment of the invention, the coating comprises polymers selected from or even that all polymers of the coating are selected from the group consisting of starch based polymer and biodegradable polymers, such as from the group consisting of any of the starch based polymers and biodegradable polymers described herein above in this section. In particular, biodegradeable polymers such as polycaprolactone, polyhydroxybuturate, polyhydroxyvalerate, polylactic acid, polyhydroxyalkanoates and/or polypropylenecarbonate can be blended with various starches (such as any of the starches described herein above in this section) in different ratios. Suitable mixtures for use in the coating composition are e.g. polycaprolactone and sago and/or cassava starch, polycaprolactone or polyhydroxybuturate and pre-dried, thermoplastic starch, polycaprolactone and gelatinized starch or thermoplastic starch. Other suitable mixtures are starch-based blends with biodegradable thermoplastic components like polyester amide, polyhydroxybuturate-co-valerate or polybutylene succinate-adipate. Polymers starches can be cross-linked with Maleic anhydride (MA) and dicumyl peroxide (DCP) giving harder items when molded and thermoformed.

In another embodiment, the coating comprises polymers selected from the starch based polymer and synthetic polymers described herein above in this section. In particular, suitable mixtures for use in the coating composition include, for example, native granular starch, modified starch, plasticized starch blended or grafted with many synthetic polymers such as polyethylene, polystyrene, Purified Terephthalic acid (PTA), optionally in mixture with aliphatic polyesters or polyvinyl alcohols in different ratios. Polybutylene succinate (PBS), polybutylene succinate adipate in blend with various starches in different ratios are also suitable, such as, for example, Polybutylene succinate in mixture with thermoplastic starch, alkylene oxide modified starches in combination with hydrolyzed polyvinyl alcohol.

In yet another embodiment, the coating comprises polymers selected from the cellulose based polymers and biodegradable polymers described herein above in this section. Thus, the coating may for example comprise a mixture of PLA and ethyl cellulose. In one embodiment the coating even consists of PLA, ethyl cellulose, one or more plasticizers (such as any of the plasticizers described herein below) and one or more UV stabilizers (such as any of the UV stabilizers described herein below).

UV Stabilizer

Radiation from sunlight can accelerate the degradation of plastics, such as the coating according to the invention. The packaging material to protect the pharmaceutical compositions (e.g. tablets) from direct sunlight may not be enough protection.

Especially for a coating with high concentration of biodegradable polymers, it can be relevant to add UV-stabilizers to the compositions, due to many unsaturated functional groups (e.g. carbonyl groups). UV-stabilizers could e.g. be titanium dioxide, metal complexes with sulfur containing groups, hindered amine light stabilizers (HALS), benzophenones, benzotriazoles. Titanium dioxide is already widely used in pharmaceutical preparations as pigment and is considered non toxic.

Plasticizer

In addition to above mentioned polymers, the coating may comprise one or more additional components. Thus, the coating may comprise at least one selected from the group consisting of i) polymers which are soluble or dispersible in water,
ii) plasticizers, and
iii) fillers In certain embodiments polymers that are soluble or dispersible in water are water soluble or dispersible cellulose derivatives. Thus, the coating material may comprise one or more plasticizers, preferably, any of the plasticizers described herein above in the section "pharmaceutically acceptable excipients" and/or any of the plasticizers described below. By way of example, the coating material may comprises one or more of the following plasticizers: Cetostearyl alcohol; castor oil; dibutyl sebacate; polyethylene oxides; and/or Poloxamer. However, other plasticizers may be also used to provide desired material properties.

Other suitable plasticizers may be selected from the group consisting of mono- and di-acetylated monoglycerides, diacetylated monoglycerides, acetylated hydrogenated cottonseed glyceride, glyceryl cocoate, Polyethylene glycols or polyethylene oxides (e.g. with a molecular weight of about 1,000-500,000 daltons), dipropylene glycol salicylate glycerin, fatty acids and esters, phthalate esters, phosphate esters, amides, diocyl phthalate, phthalyl glycolate, mineral oils, hydrogenated vegetable oils, vegetable oils, acetylated hydrogenated soybean oil glycerides, Castor oil, acetyl tributyl citrate, acetyl triethyl citrate, methyl abietate, nitrobenzene, carbon disulfide, β-naphtyl salicylate, sorbitol, sorbitol glyceryl tricitrate, fatty alcohols, cetostearyl alcohol, cetyl alcohol, stearyl alcohol, oleyl alcohol, myristyl alcohol, sucrose octaacetate, alfa-tocopheryl polyethylene glycol succinate (TPGS), tocopheryl derivative, diacetylated monoglycerides, diethylene glycol monostearate, ethylene glycol monostearate, glyceryl monooleate, glyceryl monostearate, propylene glycol monostearate, macrogol esters, macrogol stearate 400, macrogol stearate 2000, polyoxyethylene 50 stearate, macrogol ethers, cetomacrogol 1000, lauromacrogols, nonoxinols, octocinols, tyloxapol, poloxamers, polyvinyl alcohols, polysorbate 20, polysorbate 40, polysorbate 60, polysorbate 65, polysorbate 80, polysorbate 85, sorbitan monolaurate, sorbitan monooleate, sorbitan monopalmitate, sorbitan monostearate, sorbitan sesquioleate, sorbitan trioleate, sorbitan tristearate and sucrose esters, amyl oleate, butyl oleate, butyl stearate, diethylene glycol monolaurate, glycerol tributyrate, Flexol B-400, monomeric polyethylene ester, Piccolastic A-5, Piccalastic A-25, Clorafin 40, acetyl tributyl citrate, acetyl triethyl citrate, benzyl benzoate, butoxyethyl stearate, butyl and glycol esters of fatty acids, butyl diglycol carbonate, butyl ricinoleate, butyl phthalyl butyl glycolate, camphor, dibutyl sebacate, dibutyl tartrate, diphenyl oxide, glycerine, HB-40, hydrogenated methyl ester of rosin, methoxyethyl oleate, monoamylphthalate, Nevillac 10, Paracril 26, technical hydroabietyl alcohol, triethylene glycol dipelargonate, solid aliphatic alcohols and mixtures thereof.

In one embodiment, the coating is made of a material, wherein the concentration of plasticizer is from 0 to 30% w/w.

Accordingly, in certain embodiments, the coating comprises or even consists of one or more plasticizer(s) and one or more polymer(s).

Furthermore, the coating may comprise sweetening agents, flavouring agents and/or colouring agents, which may be any of the sweetening agents, flavouring agents and/or colouring agents described herein above in the section "pharmaceutically acceptable excipients".

The coating may be made of a material comprising one polymer, and wherein the concentration of the polymer is from 5 to 100% w/w.

The coating may be made of a material comprising a mixture of polymers, and wherein the total concentration of polymers is from 70 to 100% w/w.

In particular embodiments, the amount of substantially insoluble polymer included in the coating is selected from at least 50% w/w, at least 60% w/w, at least 70% w/w, or at least 80% w/w relative to the total amount of the coating.

Thus, in certain embodiments, wherein the coating comprises cellulose derivatives (such as ethyl cellulose), the amount of cellulose derivative included in the coating is selected from at least 50% w/w, at least 60% w/w, at least 70% w/w, and at least 80% w/w. In one such embodiment, the amount of cellulose derivative included in the coating is at least 85% w/w, such as, for example, 87% w/w.

In specific embodiments, the amount of plasticizer (such as cetostearyl alcohol) included in the coating is selected from at the most 19% w/w, at the most 15% w/w, at the most 12% w/w In embodiments where the coating comprises biodegradable polymers (such as polylactic acid), the amount of biodegradable polymer can be selected from at least 50% w/w, at least 60% w/w, at least 70% w/w, at least 80% w/w. In one such embodiment, the coating includes at least 85% w/w, such as, for example, 86% w/w biodegradable polymers (such as polylactic acid).

In a one embodiment, the coating includes a plasticizer (polyethylene oxides 200,000 daltons), and the amount of plasticizer is selected from at the most 20% w/w, at the most 17% w/w, at the most 15% w/w, and at the most 14% w/w plasticizer.

Outer Coat

In some cases, the pharmaceutical composition of the present invention may also comprise an outer coat that fully covers the composition, i.e., that fully covers both the matrix composition and the coating. Said outer coat may be selected from the group consisting of task masking coats, coats with aqueous moisture barriers and/or oxidative barriers to improve the stability of the composition, and cosmetic coats, such as a coat containing colouring agents, sweetening agents and/or flavouring agents in order to provide an elegant and palatable tablet and/or easily distinguishable dosage forms and dose strengths. Coating compositions having different dose strengths with outer coats of different colors can be an effective tool for easily distinguishing different dose strengths of a given drug substance. Were an outer coat is provided, it is preferably easily soluble in aqueous media such that, upon administration, the matrix comes in contact with the surrounding aqueous media via the openings in the coating and operation of the dosage form is not substantially delayed.

Preparation

The compositions for immediate release of a drug substance described herein, including matrix compositions, may be produced by various methods which are either known per se in the pharmaceutical industry or which, for example, are used in the production of polymer-based materials, depending upon the desired embodiment and the materials employed in the composition in question. One advantage of the compositions described herein is that it may be produced by methods that are relatively simple and inexpensive.

Suitable preparation methods for compositions according to the present description include, for example, extrusion, injection moulding, melt-processing, tabletting, capsule filling, thermoforming, spray coating, micro encapsulation and other methods of preparing pharmaceutical compositions. Additionally, combinations of one or more of the aforementioned methods may be employed.

Compositions as described herein may be prepared in numerous ways giving rise to different release mechanisms. In particular embodiments, the composition may be prepared, for example, by 1, 2 or multiple component injection mouldings, by conventional tablet compression, by micro encapsulation, by 1, 2 or multiple component extrusions, by capsule filling, by melt-processing or by thermoforming. The preparation may also comprise separate steps as for example wet granulation, dry granulation, melt granulation, pelletizing, spray coating, electrostatic coating or other forms of preparation methods.

Definitions

In the present context, the term "swellable" is intended to mean that the material increase/expand in size and volume as a result of contact with liquid.

In the present context, the term "immediate release" denotes a composition that disintegrates within at the most 60 minutes such as, e.g., at the most about 30 minutes or at the most about 15 minutes, when subjected to disintegration test according to Ph. Eur.

In the present context, the term "resistant to abuse by alcohol" is intended to mean that the in vitro dissolution behaviour of a composition described herein is the same or shows a decreased release rate when the composition is tested in a dissolution medium containing alcohol. The ratio ($R_{50}$) between $t_{50\% \ w/w}$ (40% v/v ethanol in medium 1) and $t_{50\% \ w/w}$ (medium 1) is 1.5 or more $t_{50\% \ w/w}$ (medium 1) denotes the time it takes to release 50% w/w of the drug substance from the pharmaceutical composition in an in vitro dissolution test according to USP 32, NF 27, (711), Apparatus 2, paddle employing water optionally buffered/adjusted to a specific pH as dissolution medium (medium 1), and $t_{50\% \ w/w}$ (40% v/v ethanol in medium 1) denotes the time it takes to release 50% w/w of the drug substance from the pharmaceutical composition in an in vitro dissolution test according to USP 32, NF 27, (711), Apparatus 2, paddle employing 40% v/v ethanol in medium 1 as dissolution medium.

The same may also apply for ratios determined, for example, when 25%, 30%, 40%, 60%, 70%, 80%, 90% and/or 95% w/w has been released, the conditions being as described above.

In the present context, the term "abuse" is intended to denote the use of a drug in order to induce euphoria or another excitement effect, i.e. the use is not intended to cure a disease or alleviate disease symptoms, but rather for obtaining intoxication.

In the present context, the term "alcoholic beverage" is intended to mean a liquid or brew containing more than 4% v/v ethanol and the volume of an alcoholic beverage is 0.4 L or more.

In the present context, the term "ingest 3 or more alcoholic beverages daily" is intended to mean that the subject on an average daily basis ingests liquid or brew with a total content of 100% ethanol of 40 ml or more. The number of alcoholic beverages is not that important, it is the total amount of alcohol ingested daily that is important. The term "average daily basis" is determined as the total intake during a week divided by 7.

The following methods and examples are intended to illustrate the invention and are not intended to limit the invention in any way.

EXPERIMENTAL

Dissolution Test

Dissolution tests were performed in accordance with USP 32, NF 27, (711), Apparatus 2 (paddle method). The dissolution medium consisted of ethanol and/or phosphate buffer solution pH 6.8, or ethanol and/or hydrochloride solution pH 1.2. The volume of the dissolution medium was 900 ml and the rotation speed of the paddles was 50 rpm throughout the dissolution run. The temperature was 37° C. Samples were withdrawn at suitable time intervals and analysed for content of drug substance by means of UV-detector or HPLC with UV-detector at a wavelength relevant for the particular drug substance. In the case of Paracetamol (Acetaminophen) a relevant wavelength is 280 nm. In the case of morphine, a relevant wavelength is 284 nm. The specific drug substances analysed for are described in the examples herein.

Methods

A general method for the preparation of a controlled release composition is described below.

Preparation of a Matrix Composition

An accurate amount of the polymer is weighed into a beaker followed by an accurate amount of the drug substance and of other pharmaceutically acceptable excipient(s), if any. The mixing is performed on a magnetic stirrer at up to 800 rpm for a time period up to 20 minutes. The mixing is performed at room temperature throughout the mixing process. The mixture is now ready to be fed into an injection moulding machine.

3 g of the mixture is then fed into a table top injection moulding machine (Haake MiniJet II, Thermo Electron, Karlsruhe, Germany) and moulded directly into a pre-moulded shell with a weight of approximately 160 mg to receive a total tablet weight of approximately 350 mg. The settings applied in the MiniJet are: Temperature 40-65° C., pressure 150-800 bar and time 10-30 seconds.

Preparation of the Coating/Shell Composition

The coating composition is prepared by first adding the ethylcellulose then cetostearyl alcohol, and finally the titanium dioxide to a MTI-Mixer at room temperature. After mixing at around 1000 rpm the mixer is stopped when the temperature reaches 40-50° C. and the adhered material is manually incorporated into the mixture. The mixture is left to cool for about 10 minutes. The mixing is then finalized with a short high-speed mix in order to minimize lump formation. The mixture is then allowed to cool to room temperature, after which it had a suitable consistency for being fed into an injection moulding machine. The injection moulding machine used is Arburg Allrounder 420 V 800-60/35.

Example of Coat Composition

Batch: 08-0017-058

| Material | % (w/w) |
|---|---|
| Ethocel | 87 |
| Cetostearyl Alcohol | 12 |
| TiO2 | 1 |
| Total | 100 |

Preparation of a Pharmaceutical Composition in Large Scale

The shell and matrix are moulded in one process, where the shell is moulded in a first step and the matrix is moulded directly into the coat in a second step (co-moulding or 2 component moulding). The injection moulding machine used is Arburg Allrounder 420 V 800-60/35.

In all the examples 1 to 21 the composition was 9 mm long, of cylindrical shape and with oval end surfaces.

Example 1

Preparation of an Immediate Release Composition Containing Hydrocodone and Paracetamol A composition (batch No. 1049-031) according to the invention was prepared from the following ingredients:

| | % (w/w) |
|---|---|
| Matrix | |
| Paracetamol | 70 |
| Hydrocodone | 2.1 |
| PEG 3350 S | 20.9 |
| Citric acid | 2 |
| Sodium bicarbonate | 5 |
| Shell/coat | |
| Ethylcellulose | 87 |
| Cetostearyl alcohol | 12 |
| Titanium dioxide | 1 |

The composition was prepared as described above.

The content of Hydrocodone in the formulation was 0.126 g and the content of paracetamol in the formulation was 4.2 g and the total mass was 6 gram. The mass of the matrix in the composition was approximately 180 mg.

The composition was subjected to the dissolution test described above. In addition to phosphate buffer medium, testing was performed in medium containing ethanol at the ratio 60:40 (v/v). The following results were obtained:

| Time (minutes) | % w/w release of Paracetamol from the composition | |
|---|---|---|
| | Buffer | Buffer:Ethanol 60:40 |
| 15 | 100 | 29 |
| 75 | 100 | 100 |
| Ratio ($R_{50}$) | $t_{50\% w/w}$ (min) in Buffer | $t_{50\% w/w}$ (min) in Buffer:Ethanol 60:40 |
| 7.13 | 0.08 | 0.57 |

The ratio ($R_{50}$) between $t_{50\% w/w}$ (40% w/w ethanol in buffer) and $t_{50\% w/w}$ (buffer) is 7.13.

Example 2

Basic Formulation With a Low Chain Polymeric Carrier, PEG 3350

A composition (batch no. 1569-034) according to the invention was prepared from the following ingredients:

| | % (w/w) |
|---|---|
| Matrix | |
| Acetaminophen | 50.0 |
| Hydrocodone | 0.5 |
| PEG3350S | 49.5 |
| Shell/coat | |
| Ethylcellulose | 87 |
| Cetostearyl alcohol | 12 |
| Titanium dioxide | 1 |

The dissolution profiles are shown in FIG. 1.

As seen in the figure, no delay in release rate was noticed when neither effervescent nor disintegrant were added to the formulation. In fact, the release in alcohol was faster compared to that in pure HCl-solution.

Example 3

Basic Formulation with a Low Chain Polymeric Carrier, PEG 6 000

A composition (batch no. 1564-036) according to the invention was prepared from the following ingredients:

|  | % (w/w) |
| --- | --- |
| Matrix | |
| Acetaminophen | 50.0 |
| Hydrocodone | 0.5 |
| PEG 6000 | 49.5 |
| Shell/coat | |
| Ethylcellulose | 87 |
| Cetostearyl alcohol | 12 |
| Titanium dioxide | 1 |

The dissolution profiles are shown in FIG. 2.

As seen in the figure, no delay in release rate was noticed when neither effervescent nor disintegrant were added to the formulation. In fact, the release in alcohol was faster compared to that in pure HCl solution.

Example 4

Basic Formulation With a High Chain Polymeric Carrier, PEG 17 000

A composition (batch no. 1564-044) according to the invention was prepared from the following ingredients:

|  | % (w/w) |
| --- | --- |
| Matrix | |
| Acetaminophen | 50.0 |
| Hydrocodone | 0.5 |
| PEG 17 000 | 49.5 |
| Shell/coat | |
| Ethylcellulose | 87 |
| Cetostearyl alcohol | 12 |
| Titanium dioxide | 1 |

The dissolution profiles are shown in FIG. 3.

As seen in the FIG., no delay in release rate was noticed when neither effervescent nor disintegrant were added to the formulation. In fact, the release in alcohol is faster compared to that in pure HCl-solution. Thereby it was seen, that the polymeric carrier does not influence the release displacement in alcohol compared to HCL solution.

Example 5

Influence on Release Profile when Effervescent is Added to the Formulation, Based on a Low Chain Polymeric Carrier PEG 3350

A composition (batch no. 1569-032) according to the invention was prepared from the following ingredients:

|  | % (w/w) |
| --- | --- |
| Matrix | |
| Acetaminophen | 50.0 |
| Hydrocodone | 0.5 |
| Citric acid | 2.0 |
| NaHCO$_3$ | 5.0 |
| PEG 3350S | 42.5 |
| Shell/coat | |
| Ethylcellulose | 87 |
| Cetostearyl alcohol | 12 |
| Titanium dioxide | 1 |

The dissolution profiles are shown in FIG. 4.

As seen in the figure, a delay in release rate of approximately 30 min. in alcohol compared to HCL solution was noticed when effervescent was added to the formulation.

Example 6

Influence on Release Profile when Effervescent is Added to the Formulation, Based on a Low Chain Polymeric Carrier PEG 6000

A composition (batch no. 1568-009) according to the invention was prepared from the following ingredients:

|  | % (w/w) |
| --- | --- |
| Matrix | |
| Acetaminophen | 50.0 |
| Hydrocodone | 0.5 |
| Citric acid | 2.0 |
| NaHCO$_3$ | 5.0 |
| PEG 6000 | 42.5 |
| Shell/coat | |
| Ethylcellulose | 87 |
| Cetostearyl alcohol | 12 |
| Titanium dioxide | 1 |

The dissolution profiles are shown in FIG. 5.

As seen in the figure, a delay in release rate of approximately 30 minutes in alcohol compared to HCl solution was noticed when effervescent was added to the formulation.

Example 7

Influence on Release Profile when Effervescent is Added to the Formulation, Based on a High Chain Polymeric Carrier PEG 17 000

A composition (batch no. 1564-058) according to the invention was prepared from the following ingredients:

|  | % (w/w) |
| --- | --- |
| Matrix | |
| Acetaminophen | 50.0 |
| Hydrocodone | 0.5 |
| Citric acid | 4.0 |
| NaHCO$_3$ | 10.0 |
| PEG 17 000 | 35.5 |
| Shell/coat | |
| Ethylcellulose | 87 |
| Cetostearyl alcohol | 12 |
| Titanium dioxide | 1 |

The dissolution profiles are shown in FIG. 6.

As seen in the figure, a delay in release rate of approximately 30 minutes in alcohol compared to HCl solution was noticed when effervescent was added to the formulation.

Example 8

Influence on Release Profile when Disintegrant is Added to the Formulation, Based on a Low Chain Polymeric Carrier PEG 6000

A composition (batch no. 1564-032) according to the invention was prepared from the following ingredients:

| | % (w/w) |
|---|---|
| Matrix Composition: | |
| Acetaminophen | 50.0 |
| Hydrocodone | 0.5 |
| PEG 6000 | 39.5 |
| Cross-caramellose Na | 10.0 |
| Shell/coat | |
| Ethylcellulose | 87 |
| Cetostearyl alcohol | 12 |
| Titanium dioxide | 1 |

The dissolution profiles are shown in FIG. 7.

As seen in the figure, the release in alcohol was faster compared to that in pure HCl-buffer.

Example 9

Influence on Release Profile when a Combination of Effervescent and Disintegrant is Added to the Formulation, Based on a High Chain Polymeric Carrier PEG 17 000

A composition (batch no. 1564-066) according to the invention was prepared from the following ingredients:

| | % (w/w) |
|---|---|
| Matrix | |
| Acetaminophen | 50.0 |
| Hydrocodone | 0.5 |
| Citric acid | 4.0 |
| NaHCO$_3$ | 10.0 |
| Cross-caramellose Na | 5.0 |
| PEG 17 000 | 30.5 |
| Shell/coat | |
| Ethylcellulose | 87 |
| Cetostearyl alcohol | 12 |
| Titanium dioxide | 1 |

The dissolution profiles are shown in FIG. 8.

As seen in the figure, a delay in release rate of approximately 35 minutes in alcohol compared to HCl solution was noticed.

Example 10

Influence on Release Profile when a Combination of Effervescent and Disintegrant is Added to the Formulation, Based on a Medium/High Chain Polymeric Carrier PEG 14 000

A composition (batch no. 1564-082) according to the invention was prepared from the following ingredients:

| | % (w/w) |
|---|---|
| Matrix | |
| Acetaminophen | 50.0 |
| Hydrocodone | 0.5 |
| Citric acid | 3.0 |
| NaHCO$_3$ | 7.5 |
| Cross-caramellose Na | 12.5 |
| PEG 14 000 | 26.5 |
| Shell/coat | |
| Ethylcellulose | 87 |
| Cetostearyl alcohol | 12 |
| Titanium dioxide | 1 |

The dissolution profiles are shown in FIG. 9.

As seen in the figure, a delay in release rate of approximately 40 minutes in alcohol compared to HCl solution was noticed.

Example 11

Influence on Release Profile when a Combination of Effervescent and Disintegrant is Added to the Formulation, Based on a Medium Chain Polymeric Carrier PEG 10 000

A composition (batch no. 1569-014) according to the invention was prepared from the following ingredients:

| | % (w/w) |
|---|---|
| Matrix Composition: | |
| Acetaminophen | 50.0 |
| Hydrocodone | 0.5 |
| Citric acid | 2.5 |
| NaHCO$_3$ | 6.25 |
| Cross-caramellose Na | 12.5 |
| PEG 10 000 | 28.25 |
| Shell/coat | |
| Ethylcellulose | 87 |
| Cetostearyl alcohol | 12 |
| Titanium dioxide | 1 |

The dissolution profiles are shown in FIG. 10.

As seen in the figure, a delay in release rate of approximately 60 minutes in alcohol compared to HCl solution was noticed.

Example 12

Influence on Release Profile when a Combination of Effervescent and Disintegrant is Added to the Formulation, Based on a Low/Medium Chain Polymeric Carrier PEG 6000

A composition (batch no. 1569-020) according to the invention was prepared from the following ingredients:

| | % (w/w) |
|---|---|
| Matrix | |
| Acetaminophen | 50.0 |
| Hydrocodone | 0.5 |

|  | % (w/w) |
| --- | --- |
| Citric acid | 2.0 |
| NaHCO₃ | 5.0 |
| Cross-caramellose Na | 12.5 |
| PEG 6 000 | 30 |
| Shell/coat | |
| Ethylcellulose | 87 |
| Cetostearyl alcohol | 12 |
| Titanium dioxide | 1 |

The dissolution profiles are shown in FIG. 11.

As seen in the figure, a delay in release rate of approximately 45 minutes in alcohol compared to HCl solution was noticed.

Example 13

Influence on Release Profile when a Combination of Effervescent and Disintegrant is Added to the Formulation, Based on a Low Chain Polymeric Carrier PEG 3350

A composition (batch no. 1569-016) according to the invention was prepared from the following ingredients:

|  | % (w/w) |
| --- | --- |
| Matrix | |
| Acetaminophen | 50.0 |
| Hydrocodone | 0.5 |
| Citric acid | 2 |
| NaHCO₃ | 5 |
| Cross-caramellose Na | 12.5 |
| PEG 3350 | 30 |
| Shell/coat | |
| Ethylcellulose | 87 |
| Cetostearyl alcohol | 12 |
| Titanium dioxide | 1 |

The dissolution profiles are shown in FIG. 12.

As seen in the figure, a delay in release rate of approximately 30 minutes in alcohol compared to HCl solution was noticed.

Example 14

Influence on Release Profile when the Effervescent Comprises Tartaric Acid and NaHCO₃ using a Low/Medium Chain Polymeric Carrier PEG 6 000

A composition (batch no. 1564-060) according to the invention was prepared from the following ingredients:

|  | % (w/w) |
| --- | --- |
| Matrix | |
| Acetaminophen | 50.0 |
| Hydrocodone | 0.5 |
| Tartaric acid | 2.0 |
| NaHCO₃ | 5.0 |
| PEG 6 000 | 42.5 |

|  | % (w/w) |
| --- | --- |
| Shell/coat | |
| Ethylcellulose | 87 |
| Cetostearyl alcohol | 12 |
| Titanium dioxide | 1 |

The dissolution profiles are shown in FIG. 13.

As seen in the figure, a small delay in release rate of approximately 20 minutes in alcohol compared to HCl solution was noticed when approximately the same amount of tartaric acid was used compared to citric acid.

Example 15

Influence on Release Profile when the Effervescent Comprises Tartaric Acid and NaHCO₃ Using a Low/Medium Chain Polymeric Carrier PEG 6 000

A composition (batch no. 1564-064) according to the invention was prepared from the following ingredients:

|  | % (w/w) |
| --- | --- |
| Matrix | |
| Acetaminophen | 50.0 |
| Hydrocodone | 0.5 |
| Tartaric acid | 4.0 |
| NaHCO₃ | 5.0 |
| PEG 6 000 | 40.5 |
| Shell/coat | |
| Ethylcellulose | 87 |
| Cetostearyl alcohol | 12 |
| Titanium dioxide | 1 |

The dissolution profiles are shown in FIG. 14.

As seen in the figure, a delay in release rate of approximately 30 minutes in alcohol compared to HCl solution was noticed. Comparing example 6 with example 14 and 15 demonstrates that twice as much tartaric acid is required to achieve a similar time delay in alcohol compared to the required amount of citric acid.

Example 16

Influence on Release Profile when the Effervescent Comprises Succinic Acid and NaHCO₃ Using a Low/Medium Chain Polymeric Carrier PEG 6 000

A composition (batch no. 1564-056) according to the invention was prepared from the following ingredients:

| Matrix | % (w/w) |
| --- | --- |
| Acetaminophen | 50.0 |
| Hydrocodone | 0.5 |
| Succinic acid | 2.0 |
| NaHCO₃ | 5.0 |
| PEG 6 000 | 42.5 |

The dissolution profiles are shown in FIG. 15.

As seen in the figure, a delay in release rate of approximately 30 minutes in alcohol compared to HCl solution was noticed.

Example 17

Influence on Release Profile when the Effervescent Comprises Malonic Acid and NaHCO₃ Using a Low/Medium Chain Polymeric Carrier PEG 6 000

A composition (batch no. 1569-036) according to the invention was prepared from the following ingredients:

|  | % (w/w) |
| --- | --- |
| Matrix |  |
| Acetaminophen | 50.0 |
| Hydrocodone | 0.5 |
| Malonic acid | 4.0 |
| NaHCO₃ | 5.0 |
| PEG 6 000 | 40.5 |
| Shell/coat |  |
| Ethylcellulose | 87 |
| Cetostearyl alcohol | 12 |
| Titanium dioxide | 1 |

The dissolution profiles are shown in FIG. 16.

As seen in the figure, a delay in release rate of approximately 20 minutes in alcohol compared to HCl solution was noticed.

Example 18

Influence on Release Profile when the Effervescent Comprises Benzoic Acid and NaHCO₃ Using a Low/Medium Chain Polymeric Carrier PEG 6 000

A composition (batch no. 1569-038) according to the invention was prepared from the following ingredients:

|  | % (w/w) |
| --- | --- |
| Matrix |  |
| Acetaminophen | 50.0 |
| Hydrocodone | 0.5 |
| Benzoic acid | 4.0 |
| NaHCO₃ | 5.0 |
| PEG 6 000 | 40.5 |
| Shell/coat |  |
| Ethylcellulose | 87 |
| Cetostearyl alcohol | 12 |
| Titanium dioxide | 1 |

The dissolution profiles are shown in FIG. 17.

As seen in the figure, a delay in release rate of approximately 25 minutes in alcohol compared to HCl solution was noticed.

Example 19

Influence on Release Profile when the Effervescent Comprises Oxalic Acid and NaHCO₃ Using a Low/Medium Chain Polymeric Carrier PEG 6 000

A composition (batch no. 1564-040) according to the invention was prepared from the following ingredients:

|  | % (w/w) |
| --- | --- |
| Matrix |  |
| Acetaminophen | 50.0 |
| Hydrocodone | 0.5 |
| Oxalic acid | 4.0 |
| NaHCO₃ | 5.0 |
| PEG 6 000 | 40.5 |
| Shell/coat |  |
| Ethylcellulose | 87 |
| Cetostearyl alcohol | 12 |
| Titanium dioxide | 1 |

The dissolution profiles are shown in FIG. 18.

As seen in the figure, a delay in release rate of approximately 50 minutes in alcohol compared to HCl solution was noticed.

Example 20

Influence on Release Profile when the Effervescent Comprises Malic Acid and NaHCO₃ Using a Low/Medium Chain Polymeric Carrier PEG 6 000

A composition (batch no. 1564-042) according to the invention was prepared from the following ingredients:

|  | % (w/w) |
| --- | --- |
| Matrix |  |
| Acetaminophen | 50.0 |
| Hydrocodone | 0.5 |
| Malic acid | 4.0 |
| NaHCO₃ | 5.0 |
| PEG 6 000 | 40.5 |
| Shell/coat |  |
| Ethylcellulose | 87 |
| Cetostearyl alcohol | 12 |
| Titanium dioxide | 1 |

The dissolution profiles are shown in FIG. 19.

As seen in the figure, a delay in release rate of approximately 20 minutes in alcohol compared to HCl solution was noticed.

Example 21

Influence on Release Profile when the Effervescent Comprises Glutaric Acid and NaHCO₃ Using a Low/Medium Chain Polymeric Carrier PEG 6 000

A composition (batch no. 1564-044) according to the invention was prepared from the following ingredients:

|  | % (w/w) |
| --- | --- |
| Matrix |  |
| Acetaminophen | 50.0 |
| Hydrocodone | 0.5 |
| Glutaric acid | 4.0 |
| NaHCO₃ | 5.0 |
| PEG 6 000 | 40.5 |

-continued

| | % (w/w) |
|---|---|
| Shell/coat | |
| Ethylcellulose | 87 |
| Cetostearyl alcohol | 12 |
| Titanium dioxide | 1 |

The dissolution profiles are shown in FIG. 20.

As seen in the figure, a delay in release rate of approximately 25 minutes in alcohol compared to HCl solution was noticed.

Example 22

Influence on Release Profile, when a Combination of Effervescent and Disintegrant is Added to the Formulation, Based on a Low/Medium Chain Polymeric Carrier PEG 6000

A composition (batch no. 1569-046) according to the invention was prepared from the following ingredients:

| | % (w/w) |
|---|---|
| Matrix | |
| Morphine sulphate pentahydrate | 5.0 |
| Citric acid | 2.5 |
| NaHCO$_3$ | 6.25 |
| Cross-caramellose Na | 12.5 |
| PEG 6000 | 73.75 |
| Shell/coat | |
| Ethylcellulose | 87 |
| Cetostearyl alcohol | 12 |
| Titanium dioxide | 1 |

The dissolution profiles are shown in FIG. 21.

As seen in the figure, a delay in release rate of approximately 75 minutes in alcohol compared to HCl solution was noticed.

Example 23

Influence on Release Profile, when a Combination of Effervescent and Disintegrant is Added to the Formulation, Based on a Low/Medium Chain Polymeric Carrier PEG 6000

A composition (batch no. 1569-048) according to the invention was prepared from the following ingredients:

| | % (w/w) |
|---|---|
| Matrix | |
| Morphine sulphate pentahydrate | 5.0 |
| Citric acid | 6.0 |
| NaHCO$_3$ | 15 |
| Cross-caramellose Na | 12.5 |
| PEG 6000 | 61.5 |
| Shell/coat | |
| Ethylcellulose | 87 |
| Cetostearyl alcohol | 12 |
| Titanium dioxide | 1 |

The dissolution profiles are shown in FIG. 22.

As seen in the figure, a delay in release rate of approximately 45 minutes in alcohol compared to HCl solution was noticed.

Example 24

Influence on Release Profile, when a Combination of Effervescent and Disintegrant is Added to the Formulation, Based on a High Chain Polymeric Carrier PEG 17 000

A composition (batch no. 1569-050) according to the invention was prepared from the following ingredients:

| | % (w/w) |
|---|---|
| Matrix | |
| Morphine sulphate pentahydrate | 5.0 |
| Citric acid | 2.5 |
| NaHCO$_3$ | 6.25 |
| Cross-caramellose Na | 12.5 |
| PEG 17 000 | 73.75 |
| Shell/coat | |
| Ethylcellulose | 87 |
| Cetostearyl alcohol | 12 |
| Titanium dioxide | 1 |

The dissolution profiles are shown in FIG. 23.

As seen in the figure, a delay in release rate of approximately 75 minutes in alcohol compared to HCl solution was noticed.

The invention claimed is:

1. An immediate release pharmaceutical composition, wherein the composition is resistant to alcohol-induced dose dumping, the composition comprising:
   a. one or more drug substances; and
   b. a polymer matrix resistant to alcohol-induced dose dumping,
   wherein the drug substance is dispersed within the polymer matrix, and wherein the polymer matrix consists essentially of
   (i) a polyglycol having a molecular weight of from 900 to about 17,000 Daltons;
   (ii) one or more effervescent agents; and
   (iii) one or more disintegrants.

2. The immediate release pharmaceutical composition according to claim 1, wherein the composition is resistant to abuse by intake of alcohol when the alcohol is ingested either:
   a. together with the composition, or
   b. within a period of up to 60 minutes before and up to 60 minutes after the intake of the composition.

3. The immediate release pharmaceutical composition of claim 1, wherein the composition is suitable for administration to a patient that ingests three or more alcoholic beverages daily.

4. The immediate release pharmaceutical composition of claim 3, wherein the composition is resistant to alcohol-induced dose dumping when a patient to whom the composition is administered ingests an alcoholic beverage either:
   a. together with the composition, or
   b. within a period of up to 60 minutes before and up to 60 minutes after ingesting the composition.

5. The immediate release pharmaceutical composition according to claim 1, wherein the one or more effervescent agents comprise a water soluble organic acid and a water soluble bicarbonate.

6. The immediate release pharmaceutical composition according to claim 1, wherein the polyglycol has a molecular weight selected from 1000, 1100, 1900, 2000, 2800, 2900, 3350, 4400, 5800, 6000, 8000, 8400, 10,000, 12,000, 14,600, and 17,000 Daltons.

7. The immediate release pharmaceutical composition according to claim 1, wherein the one or more drug substances is selected from the group consisting of anaesthetics, analgesics, opioids, antipyretics, antimigraine agents, anti-epileptics, anti-parkinson agents, dopaminergic agents, antipsychotics, anxiolytics, sedatives, antidepressants, psychostimulating agents used for ADHD and nootropics, and agents used in addictive disorders.

8. The immediate release pharmaceutical composition according to claim 7, wherein the one or more effervescent agents comprise a water soluble organic acid and a water soluble bicarbonate.

9. The immediate release pharmaceutical composition according to claim 7, wherein the polyglycol has a molecular weight selected from 1000, 1100, 1900, 2000, 2800, 2900, 3350, 4400, 5800, 6000, 8000, 8400, 10,000, 12,000, 14,600, or 17,000 Daltons.

10. The immediate release pharmaceutical composition according to claim 7, wherein the composition is resistant to alcohol-induced dose dumping when the alcohol is ingested either:

a. together with the composition, or
  b. within a period of up to 60 minutes before and up to 60 minutes after ingesting the composition.

11. The immediate release pharmaceutical composition according to claim 7, wherein the one or more drug substances is released from the composition in the stomach with a release profile that is dependent on the concentration of ethanol, such that an increased ethanol concentration results in a decreased rate of drug release.

12. The immediate release pharmaceutical composition according to claim 1, wherein the one or more disintegrants is selected from the group consisting of sodium starch glycolate, povidone, sodium alginate, alginic acid, calcium alginate, carboxymethylcellulose calcium, carboxymethylcellulose sodium, powdered cellulose, chitosan, croscarmellose sodium, crospovidone, cross-linked polyvinylpyrrolidone, hydroxypropyl starch, hydroxypropyl cellulose low-substituted, magnesium aluminium silicate, methylcellulose, microcrystalline cellulose, pregelatinized starch, docusae sodium, guar gum, and polacrilin potassium.

13. The immediate release pharmaceutical composition according to claim 1, wherein the concentration of the one or more disintegrants in the composition is in an amount selected from about 1% to about 60% by weight and about 5% to about 50% by weight.

* * * * *